US008674074B2

(12) United States Patent
Østergaard

(10) Patent No.: US 8,674,074 B2
(45) Date of Patent: Mar. 18, 2014

(54) COAGULATION FACTOR VII POLYPEPTIDES

(75) Inventor: Henrik Østergaard, Roskilde (DK)

(73) Assignee: Novo Nordisk Healthcare AG, Zurich (CH)

( * ) Notice: Subject to any disclaimer, the term of this patent is extended or adjusted under 35 U.S.C. 154(b) by 381 days.

(21) Appl. No.: 12/762,867

(22) Filed: Apr. 19, 2010

(65) Prior Publication Data

US 2010/0197597 A1 Aug. 5, 2010

Related U.S. Application Data

(63) Continuation of application No. 11/367,189, filed on Mar. 3, 2006, now abandoned, which is a continuation of application No. PCT/DK2004/000594, filed on Sep. 9, 2004.

(60) Provisional application No. 60/503,418, filed on Sep. 16, 2003.

(30) Foreign Application Priority Data

Sep. 9, 2003 (DK) .................................. 2003 01296

(51) Int. Cl.
*C07K 1/00* (2006.01)
(52) U.S. Cl.
USPC .................. 530/350; 530/300; 514/2; 514/12
(58) Field of Classification Search
None
See application file for complete search history.

(56) References Cited

U.S. PATENT DOCUMENTS

| | | | |
|---|---|---|---|
| 5,288,629 A | 2/1994 | Berkner | |
| 5,580,560 A | 12/1996 | Nicolaisen et al. | |
| 5,679,639 A * | 10/1997 | Griffin et al. ................. | 514/13.7 |
| 5,847,407 A | 12/1998 | Lucero et al. | |
| 5,968,751 A * | 10/1999 | Griffin et al. .................. | 435/7.1 |
| 5,994,296 A | 11/1999 | Ruf et al. | |
| 7,173,000 B2 | 2/2007 | Ruf et al. | |
| 7,416,860 B2 | 8/2008 | Persson et al. | |
| 2003/0040480 A1 | 2/2003 | Rojkjaer | |
| 2003/0044908 A1 | 3/2003 | Persson | |
| 2003/0054018 A1 | 3/2003 | Hedner | |
| 2003/0073638 A1 | 4/2003 | Kjalke | |
| 2003/0096338 A1 | 5/2003 | Pedersen et al. | |
| 2003/0130191 A1 | 7/2003 | Persson et al. | |
| 2003/0170863 A1 | 9/2003 | Persson et al. | |
| 2004/0033566 A1 | 2/2004 | Ruf et al. | |

FOREIGN PATENT DOCUMENTS

| | | |
|---|---|---|
| EP | 0200421 | 4/1985 |
| EP | 1593389 | 11/2005 |
| JP | 3500963 | 3/1991 |
| JP | 10/59866 A | 3/1998 |
| JP | 2001 061479 | 3/2001 |
| JP | 2003-521930 | 7/2003 |
| WO | WO 88/10295 | 12/1988 |
| WO | 91/11514 A1 | 8/1991 |
| WO | WO94/07515 | 4/1994 |
| WO | 94/27631 | 12/1994 |
| WO | WO96/12800 | 5/1996 |
| WO | WO97/20939 | 6/1997 |
| WO | 98/32446 A1 | 7/1998 |
| WO | WO98/31394 | 7/1998 |
| WO | WO 9858661 | 12/1998 |
| WO | 0028065 A1 | 5/2000 |
| WO | WO 01/58935 | 8/2001 |
| WO | WO 0158935 | 8/2001 |
| WO | WO01/75086 | 10/2001 |
| WO | 01/85199 A1 | 11/2001 |
| WO | WO01/82943 | 11/2001 |
| WO | WO01/83725 | 11/2001 |
| WO | WO 01/83725 | 11/2001 |
| WO | WO01/85198 | 11/2001 |
| WO | WO02/22776 | 3/2002 |
| WO | WO 02/22776 | 3/2002 |
| WO | WO 02/029045 | 4/2002 |
| WO | WO 02/38162 | 5/2002 |
| WO | WO02/38162 | 5/2002 |
| WO | WO 0238162 | 5/2002 |
| WO | WO02/062376 | 8/2002 |
| WO | WO 02/062377 | 8/2002 |
| WO | WO 02/077218 | 10/2002 |
| WO | WO02077218 | 10/2002 |
| WO | WO 02087605 | 11/2002 |
| WO | WO 03007983 | 1/2003 |
| WO | WO 03/027147 | 4/2003 |
| WO | WO 03039581 | 5/2003 |
| WO | WO 03039582 | 5/2003 |
| WO | WO 03039584 | 5/2003 |
| WO | WO 03039590 | 5/2003 |
| WO | 03/093465 A1 | 11/2003 |
| WO | WO2004/029090 | 4/2004 |
| WO | WO2004/033566 | 4/2004 |

(Continued)

OTHER PUBLICATIONS

Dickinson, C.D. et al., Proc Natl Acad Sci USA, vol. 93, pp. 14379-14384 (1996).
Persson, E. et al., Bio Chem, vol. 40, pp. 3251-3256 (2001).
O'Brein, D.P. et al., Bio Chem, vol. 33, pp. 14162-14169 (1994).
Sridhara, S. et al., Am J Hematol, vol. 53, pp. 66-71 (1996).
Neuenschwander, P. et al., Alteration of the Substrate and Inhibitor Specificities of Blood Coagulation Factor VIIa: Importance of Amino Acid Residue K192, Biochemistry, vol. 34, pp. 8701-8707 (1995).
Bernardi, F. et al., Mutation Pattern in Clinically Asymptomatic Coagulation Factor VII Deficiency, Human Mutation, vol. 8, pp. 108-115 (1996).
Chang, Yu-Jia et al., Engineered Recombinant Factor VII Q217 Variants with Altered Inhibitor Specificities, Biochemistry, vol. 38, pp. 10940-10948 (1999).

(Continued)

*Primary Examiner* — Hope Robinson
(74) *Attorney, Agent, or Firm* — Michael J. Brignati

(57) ABSTRACT

The present invention relates to novel coagulation Factor VII polypeptides, polynucleotide constructs encoding such polypeptides, as well as vectors and host cells comprising and expressing the polynucleotide, pharmaceutical compositions, uses and methods of treatment.

20 Claims, 4 Drawing Sheets

(56) References Cited

FOREIGN PATENT DOCUMENTS

| | | |
|---|---|---|
| WO | WO 2004/110469 | 12/2004 |
| WO | WO 2005/024006 | 3/2005 |
| WO | WO 2005/058283 | 6/2005 |
| WO | WO 2005/075635 | 8/2005 |
| WO | WO 2006/014253 | 2/2006 |
| WO | WO 2006/018204 | 2/2006 |

OTHER PUBLICATIONS

Leonard, B.J.N. et al., Calcium Dependency of Conformational Changes in the EGF-1 Region upon Activation, But not Active Site Inhibition, of Human FVII, Abstract 1473, Journal of the International Society of Thrombosis and Haemostasis, Supplmental, p. 466 (1999).

Mizoguchi, J. et al., Structural Element of Factor VIIa Required for Active Site Information, Abstract 1474, Journal of the International Society of Thrombosis and Haemostasis, Supplmental, p. 466 (1999).

Iakhiaev, A. et al., The Role of Catalytic Cleft and Exosite Residues of Factor VIIa for Complex Formation with Tissue Factor Pathway Inhibitor, Thrombosis and Haemostasis, vol. 85, pp. 458-463 (2001).

Jin, Jianping, Structure-Function Study of Blood Coagulation Factor VII by In Vitro Mutagenesis and Computer Simulation, UMI Dissertation Services, 2000.

Jin, J. et al., Four Loops of the Catalytic Domain of Factor VIIa Mediate the Effect of the First EGF-Like Domain Substitution on Factor VIIa Catalytic Activity, Journal of Molecular Biology, Abstract (2001).

Persson, E. et al., Substitution of Valine for Leucine 305 in Factor VIIa Increases the Intrinsic Enzymatic Activity, Journal of Biological Chemistry, vol. 278(31), pp. 29195-29199 (2001).

Petersen, L.C. et al., Binding of Zn2+ to a Ca2+ loop allosterically attenuates the activity of factor VIIa and reduces its affinity for tissue factor [In Process Citation], Protein Science, vol. 9, pp. 859-866 (2000).

Peyvandi, F. et al., Molecular Characterization and Three-Dimensional Structural Analysis of Mutations in 21 Unrelated Families with Inherited Factor VII Deficiency, Thrombosis and Haemostasis, vol. 84, pp. 250-257 (2000).

Peyvandi, F. et al., Two Naturally Occurring Mutations on FVII Gene (S363I-W364C) Altering Intrinsic Catalytic Activity, Thrombosis and Haemostasis, vol. 88, pp. 750-755 (2002).

Stenesh, J., Dictionary of Biochemistry and Molecular Biology, $2^{Nd}$ Edition, (1989).

Kumar, Anuradha and Daryl S. Fair, Specific molecular interaction sites on factor VII involved in factor X activation, Eur. J. Biochem., vol. 217(2), pp. 509-518 (1993).

Soejima, K. et al., Factor VIIa Modified in the 170 Loop Shows Enhanced Catalytic Activity but Does Not Change the Zymogen-like Property, Journal of Biological Chemistry, vol. 276(20), 17229-35 (2001).

Sommer, S.S., Assessing the underlying pattern of human germline mutations: lessons from the factor IX gene, FASEB Journal, vol. 6,(10), pp. 2767-2774 (1992).

Kimchi-Sarfaty et al., Science, vol. 315, pp. 526-528 (2007).

Bowie et al., Science, vol. 247, pp. 1306-1310 (1990).

Skolnick et al., TIBTECH, vol. 18, pp. 34-39 (2000).

Wells, Biochemistry, vol. 29, pp. 8509-8517 (1990).

Essex, D. et al., Successful Use of Recombinant Factor VIIa for Trauma-Associated Massive Hemorrhage, Blood, vol. 96(11Pat), p. 268A (2000).

Grounds, Mike, Recombinant factor VIIa and its use in severe bleeding in surgery and trauma: a review, Blood Reviews, vol. 17, pp. S11-S21 (2003).

Holcomb, J.B. et al., Use of Recombinant FVIIa for Intraperitoneal Coagulopathic Bleeding in a Septic Patient, Current Surgery, vol. 60(4), pp. 423-427 (2003).

Ingerslev, J. et al., Home treatment with recombinant activated factor VII: results from one centre, vol. 9(suppl), pp. S107-S110 (1998).

Kristensen, A.T. et al., Potential uses of recombinant human factor VIIa in veterinary medicine, The Veterinary Clinics of North America Small Animal Practice, vol. 33, pp. 1437-1451 (2003).

Kulkarni, R. et al., Recombinant factor VIIa use in paediatric traumatic liver injuries in children, JVF Congress of WHF Seville, abstract, (2002).

Kamphuisen, P.W. et al., Control of Life-Threatening Pulmonary Bleeding with Activated Recombinant Factor VII, The American Journal of Medicine, vol. 112, pp. 332-333 (2002).

Kenet, G. et al., Treatment of traumatic bleeding with recombinant factor VIIa, The Lancet, vol. 354, p. 1879 (1999).

Lynn, M. et al., Early Use of Recombinant Factor VIIa Improves Mean Arterial Pressure and May Potentially Decrease Mortality in Experimental Hemorrhagic Shock: A Pilot Study, The Journal of Trauma, vol. 52, pp. 703-707 (2002).

Lynn, M. et al., Updates in the management of severe coagulopathy in trauma patients, Intensive Care Medicine, vol. 28, pp. 241-247 (2002).

Martinowitz, U. et al., Recombinant Activated Factor VII for Adjunctive Hemorrhage Control in Trauma and Surgey: The Isreali Compassionate Registry, Thrombosis and Haemostasis, suppl.,(2001).

Martinowitz, U. et al., Intravenous rFVIIa Administered for Hemorrhage Control in Hypothermic Coagulopathic Swine with Grade V Liver Injuries, The Journal of Trauma, vol. 50, pp. 721-729 (2001).

Martinowitz, U. et al., New Approach for the Management of Catastrophic Bleeds in Trauma and Surgery: Enhancement of Coagulation at the Site of Injury by Recombinant Activated Factor VII, Blood, vol. 98, pp. 827A-828A (2001).

Martinowitz, U. et al., Recombinant Activated Factor VII for Adjunctive Hemorrhage Control in Trauma, The Journal of Trauma, vol. 51(3), pp. 431-439 (2001).

Martinowitz, U. et al., Possible role of recombinant activated factor VII in the control of hemorrhage associated with massive trauma, Canadian Journal of Anesthesia, vol. 49(suppl. 2), pp. 15-20 (2002).

Meng, Z.H. et al., The Effect of temperature and pH on the Activity of Factor VIIa: Implications for the Efficacy of High-Dose Factor VIIa in Hypothermic and Acidotic Patients, The Journal of Trauma, vol. 55, pp. 886-891 (2003).

Morenski, J.D. et al., Recombinant activated VII for cerebral injury-induced coagulopathy in pediatric patients, Journal of Neurosurgery, vol. 98, pp. 611-616 (2003).

Chiu, J. et al., Transfusion-sparing hemostatic agents, Transfusion Medicine, vol. 9, pp. 544-550 (2002).

Arvieux, C. et al., Damage control laparotomy for haemorragic abdominal trauma, Annales De Chirugie, vol. 128, pp. 150-158 (2003).

Hardy, J-F., Managing uncontrolled hemorrhage in trauma and surgery: anovel and promising approach, Canadian Journal of Anesthesia, vol. 49(suppl), pp. 84-86 (2002).

Armand, R. et al., Treating Coagulopathy in Trauma Patients, Transfusion Medicine Reviews, vol. 17(3), pp. 223-231 (2003).

Dejgaard, A., Update on Novo Nordisk's clinical trial programme on NovoSeven®, Blood Coagulation and Fibrinolysis, vol. 14(suppl), pp. 39-41 (2003).

Holcomb, J., Discussion, The Journal of Trauma, vol. 51(3), pp. 438-439 (2001).

Erhardtsen, E., Ongoing NovoSeven® Trials, Intensive Care Medicine, vol. 28, pp. 248-255 (2002).

Eikelboom, J.W. et al., Recombinant activated factor VII for the treatment of life-threatening haemorrhage, Blood Coagulation and Fibrinolysis, vol. 14, pp. 713-717 (2003).

Alcorn, K. et al., Single Institution Experience of Recombinant Activated Factor VII (Novo-Seven) in the Management of Intractable Bleeding in Surgical and Trauma Patients, Blood, vol. 100(11), p. 3840 (2002).

Argall, J., Factor VIIa for intractable blood loss in trauma, Emergency Medical Journal, vol. 19, pp. 556-557 (Nov. 2002).

Aggarwal, A. et al., Use of recombinant Activated Factor VII (rFVIIa) in the Management of Intractable Bleeding in Srugical and Trauma Patients, Blood, vol. 98(11), p. 66B (2001).

(56) References Cited

OTHER PUBLICATIONS

Aldouri, M., The Use of Recombinant Factor VIIa in Controlling Surgical Bleeding in Non-Haemophiliac Patients, Pathophysiology of Haemostasis and Thrombosis, vol. 32(Suppl1), pp. 141-146 (2002).
Dutton, R. et al., Recombinant Factor VIIa for Controlling of Hemorrhage: Early Experience in Critically Ill Trauma Patients, Jorunal of Clinical Anesthesia, vol. 15, pp. 184-188 (2003).
Eikelboom, J. et al., Recombinant Activated Factor VIIa for Massive Hemorrhage in Non-Hemophiliac Patients: The Australian Experience, Blood, vol. 100(11), p. 2800 (2002).
Becton, D. et al., Treatment of Bleeding with rFVIIa (NovoSeven®) in Four Diverse Cases, Blood, vol. 98(11), p. 263a (2001).
Sapsford, W., A role for recombinant activated factor VII in trauma, Trauma, vol. 4, pp. 117-123 (2002).
Martinowitz, U. et al., Meeting Abstract, 43$^{rd}$ Annual Meeting of the American Society of Hematology, Part 1, Dec. 7-11, 2001.
Essex, D. et al., 42$^{nd}$ Annual Meeting of the American Society of Hematology, Dec. 1-5, 2000.
Aggarwal, A. et al., 43$^{rd}$ Annual Metting of the Society of Hematology, Part 2, Dec. 7-11, 2001.
Murkin, J.M. et al., A novel hemostatic agent: the potential role of recombinant activated factor VII (rFVIIa) in anesthetic practice, Canadian Journal of Anesthesia, vol. 49(10)(suppl.), pp. S21-S26 (2002).
O'Neill, P.A. et al., Successful Use of recombinant Activated Factor VII for Trauma-Associated Hemorrhage in a Patient without Preexisting Coagulopathy, The Journal of Trauma, vol. 52(2), pp. 400-405 (2002).
Park, P. et al., Recombinant Activated Factor VII for the Rapid Correction of Coagulopathy in Nonhemophilic Neurosurgical Patients, Neurosurgery, vol. 53(1), pp. 34-39 (2003).
Petrini, P. et al., Treatment of acute bleeds with recombinant activated factor VII during immune tolerance therapy, Blood Coagulation and Fibrinolysis, vol. 9(suppl), pp. S143-S146 (1998).
Robbins, D. et al., Successful treatment of High Titer Inhibitors in Mild Hemophilia A with Avoidance of Factor VIII and Immunosuppressive Therapy, American Journal of Hematology, vol. 68, pp. 184-188 (2001).
Schreiber, M.A. et al., The Effect of Recombinant Factor VIIa on Coagulopathic Pigs with Grade V Liver Injuries, The Journal of Trauma, vol. 53(2), pp. 252-259 (2002).
Schuster, R. et al., Treatment of Bleeding in Severe Hemorrhagic Pancreatitis with recombinant Factor VIIa, The American Surgeon, vol. 69 (11), pp. 1017-1018 (2003).
Siegel, L.J. et al., Cerebral Sinus Thrombosis in a Trauma Patient after Recombinant Activated Factor VII Infusion, Anesthesiology, vol. 11(2), pp. 441-443 (2004).
Susmann, G. et al., Early intensive care unit intervention for trauma care: what alters the outcome?, Current Opinion in Critical Care, vol. 8(6), pp. 587-592 (2002).
Aitken, M.G., Recombinant factor VIIa, Emergency Medicine Australasia, vol. 16, pp. 446-455 (2004).
Bianchi, A. et al., Treatment of bleeding with recombinant factor VIIa in a patient with extensive burns, Thrombosis and Haemostasis 2004 91 1: 203-204.
Horton, J.W., Free Radicals and lipid peroxidation mediated injury in burn trauma: the role of antioxidant therapy, Toxicology, vol. 189, pp. 75-88 (2003).
Borgognone, A. et al., Ruolo Dell'Antitrombina Terza E Del Fattore Settimo Nella Prognosi E Nella Terapia Della Malattia Da Ustione, Riv Ital Di Chi Plastica, vol. 21(4), pp. 459-464 (1989).
Office Action of Jun. 15, 2007 for U.S. Appl. No. 11/497,721, filed Aug. 2, 2006 Inventors: Axelsen et al.
Office Action of Mar. 19, 2008 for U.S. Appl. No. 11/497,721, filed Aug. 2, 2006 Inventors: Axelsen et al.
Boffard, K.D., et al., Letters to the Editor, The Journal of Trauma, vol. 60(1), pp. 243-244 (2006).
Webert, K.E., et al., Letters to the Editor, The Journal of Trauma, vol. 60(1), pp. 242-243 (2006).
Office Action of May 13, 2009 for U.S. Appl. No. 11/111,663, filed Sep. 24, 2003 Inventors: Persson et al.
Seffernick et al., J. Bacteriology, vol. 183, pp. 2405-2410 (2001).
Dickinson et al., Journal of Biological Chemistry, 1997, vol. 272, No. 32, pp. 19875-19879.
Scopes et al., European Journal of Biochemistry, 1998, vol. 251, pp. 382-388.
Levy et al., Archives of Biochemistry and Biophysics, 1996, vol. 326, pp. 145-151.
Database EMBL (Online) Aug. 30, 1996, "MUS Musculus Coagulation Factor VII Gene, Complete CDS", XP002660666.
Petersen, L.C et al., European Journal of Biochemistry, "Thermal Effects on an Enzymatically Latent Conformation of Coagulation Factor VIIa", 1999, vol. 261, No. 1, pp. 124-129.
Broze, Jr., George J. et al., Journal of Biological Chemistry, "Purification and Properties of Human Coagulation Factor VII", 1980, vol. 255, No. 4, pp. 1242-1247.
Ruf et al., "Importance of Factor VIIa GLA-Domain Residue ARG-36 for Recognition of the Macromolecular Substrate Factor X GLA-Domain", Biochemistry, 1999, vol. 38, pp. 1957-1966.
Iwanaga, S et al, Thrombosis and Haemostasis, "Structural Element of Factor VIIa Required for Active Site Formation", 1999, vol. 466, No. Suppl., pp. Abst 1474.
Kao et al, Biochemistry, "The Effect of O-Fucosylation on the First EGF-Like Domain From Human Blood Coagulation Factor VII", 1999, vol. 38, No. 22, pp. 7097-7110.
Kemball-Cook et al., "Coagulation Factor VII GLN100 Forward Arrow ARG", Journal of Biological Chemistry, 1998, vol. 273, pp. 8516-8521.
Kemball-Cook et al., Journal of Structural Biology, "Crystal Structure of Active Site-Inhibited Human Coagulation Factor VIIa (DES-GLA)1", 1999, vol. 127, No. 3, pp. 213-223.
Yoshitake, Biochemistry, "Nucleotide Sequence of the Gene for Human Factor IX", 1985, vol. 24, No. -, pp. 3736-3750.
Muranyi et al, Biochemistry, "Solution Structure of the N-Terminal EGF-Like Domain From Human Factor VII", 1998, vol. 37, pp. 10605-10615.
O'Hara et al. I, Proceedings of the National Academy of Sciences of the USA, "Nucleotide Sequence of the Gene Coding for Human Factor VII, a Vitamin K-Dependent Protein Participating in Blood Coagulation", 1987, vol. 84, pp. 5158-5162.
Zhang et al, "Structure of Extracellular Tissue Factor Complexed With Factor VIIa Inhibited With a BPTI Mutant", Journal of Molecular Biology, 1999, vol. 285, pp. 2089-2104.
Pike et al. Proceedings of the National Academy of Sciences of the USA, "Structure of Human Factor VIIa and Its Implications for the Triggering of Blood Coagulation", 1999, vol. 96, pp. 8925-8930.
Banner et al, Nature, "The Crystal Structure of the Complex of Blood Coagulation Factor VIIa With Soluble Tissue Factor", 1996, vol. 380, pp. 41-46.
Bharadwaj et al, "Factor VII Central—A Novel Mutation in the Catalytic Domain That Reduces Tissue Factor Binding, Impairs Activtion by Factor XA, and Abolishes Amidolytic and Coagulant Activity", Journal of Biological Chemistry, 1996, vol. 271, No. 48, pp. 30685-30691.
De Grouchy et al. I, "Regional Mapping of Clotting Factors VII and X to 13Q34. Expression of Factor VII Through Chromosome 8", Human Genetics, 1984, vol. 66, pp. 230-233.
Østerud et al., "Activation of Factor IX by the Reaction Product of Tissue Factor and Factor VII: Additional Pathway for Initiating Blood Coagulation", Proceedings of the National Academy of Sciences of the USA, 1977, vol. 74, pp. 5260-5264.
Hedner, "Novoseven as a Universal Haemostatic Agent", Blood Coagulation and Fibrinolysis 2000, vol. 11, No. 1, pp. S107-2111.
Guo et al., "Protein Tolerance to Random Amino Acid Change", PNAS, 2004, vol. 101, No. 25, pp. 9205-9210.
Lisman et al., "Enhanced in Vitro Procoagulant and Antifibrinolytic Potential of Superactive Variants of Recombinant Factor VIIa in Severe Haemophilia A", Journal of Thrombosis and Haemostasis, 2003, vol. 1, No. 10, pp. 2175-2178.
U.S. Appl. No. 60/184,036, filed Feb. 22, 2000, Maxygen, Inc.

\* cited by examiner

SEQ ID NO: 1 (The amino acid sequence of native human coagulation Factor VII):

Ala-Asn-Ala-Phe-Leu-GLA-GLA-Leu-Arg-Pro-Gly-Ser-Leu-GLA-Arg-GLA-Cys-Lys-
                    5              10              15

GLA-GLA-Gln-Cys-Ser-Phe-GLA-GLA-Ala-Arg-GLA-Ile-Phe-Lys-Asp-Ala-GLA-Arg-
        20              25              30              35

Thr-Lys-Leu-Phe-Trp-Ile-Ser-Tyr-Ser-Asp-Gly-Asp-Gln-Cys-Ala-Ser-Ser-Pro-
            40              45              50

Cys-Gln-Asn-Gly-Gly-Ser-Cys-Lys-Asp-Gln-Leu-Gln-Ser-Tyr-Ile-Cys-Phe-Cys-
    55              60              65              70

Leu-Pro-Ala-Phe-Glu-Gly-Arg-Asn-Cys-Glu-Thr-His-Lys-Asp-Asp-Gln-Leu-Ile-
            75              80              85
90

Cys-Val-Asn-Glu-Asn-Gly-Gly-Cys-Glu-Gln-Tyr-Cys-Ser-Asp-His-Thr-Gly-Thr-
                95              100             105

Lys-Arg-Ser-Cys-Arg-Cys-His-Glu-Gly-Tyr-Ser-Leu-Leu-Ala-Asp-Gly-Val-Ser-
    110             115             120             125

Cys-Thr-Pro-Thr-Val-Glu-Tyr-Pro-Cys-Gly-Lys-Ile-Pro-Ile-Leu-Glu-Lys-Arg-
            130             135             140

Fig. 2

```
Gly-   Asn-Ala-Ser-Lys-Pro-Gln-Gly-Arg-Ile-Val-Gly-Gly-Lys-Val-Cys-Pro-Lys-
            145                 150                 155                 160

Gly-   Glu-Cys-Pro-Trp-Gln-Val-Leu-Leu-Leu-Val-Asn-Gly-Ala-Gln-Leu-Cys-Gly-
                   165                 170                 175
180

Ile-   Thr-Leu-Ile-Asn-Thr-Ile-Trp-Val-Val-Ser-Ala-Ala-His-Cys-Phe-Asp-Lys-
                   185                 190                 195

His-   Lys-Asn-Trp-Arg-Asn-Leu-Ile-Ala-Val-Leu-Gly-Glu-His-Asp-Leu-Ser-Glu-
            200                 205                 210                 215

Tyr-   Asp-Gly-Asp-Glu-Gln-Ser-Arg-Arg-Val-Ala-Gln-Val-Ile-Ile-Pro-Ser-Thr-
                   220                 225                 230

Val-   Val-Pro-Gly-Thr-Thr-Asn-His-Asp-Ile-Ala-Leu-Leu-Arg-Leu-His-Gln-Pro-
            235                 240                 245                 250

Glu-   Val-Leu-Thr-Asp-His-Val-Val-Pro-Leu-Cys-Leu-Pro-Glu-Arg-Thr-Phe-Ser-
                   255                 260                 265
270

Leu-   Arg-Thr-Leu-Ala-Phe-Val-Arg-Phe-Ser-Leu-Val-Ser-Gly-Trp-Gly-Gln-Leu-
                   275                 280                 285
```

Fig. 2 (cont.)

```
        Asp-Arg-Gly-Ala-Thr-Ala-Leu-Glu-Leu-Met-Val-Leu-Asn-Val-Pro-Arg-Leu-
Met-
            290                 295                 300                 305

Thr-Gln-Asp-Cys-Leu-Gln-Gln-Ser-Arg-Lys-Val-Gly-Asp-Ser-Pro-Asn-Ile-
Thr-
                    310                 315                 320

Glu-Tyr-Met-Phe-Cys-Ala-Gly-Tyr-Ser-Asp-Gly-Ser-Lys-Asp-Ser-Cys-Lys-
Gly-
        325                 330                 335                 340

Asp-Ser-Gly-Gly-Pro-His-Ala-Thr-His-Tyr-Arg-Gly-Thr-Trp-Tyr-Leu-Thr-
Gly-
                    345                 350                 355
360

Ile-Val-Ser-Trp-Gly-Gln-Gly-Cys-Ala-Thr-Val-Gly-His-Phe-Gly-Val-Tyr-
Thr-
                    365                 370                 375

Arg-Val-Ser-Gln-Tyr-Ile-Glu-Trp-Leu-Gln-Lys-Leu-Met-Arg-Ser-Glu-Pro-
Arg-
            380                 385                 390                 395

Pro-Gly-Val-Leu-Leu-Arg-Ala-Pro-Phe-Pro
                400                 405 406
```

Fig. 2 (con.t)

SEQUENCE LISTING

```
<160> NUMBER OF SEQ ID NOS: 1

<210> SEQ ID NO 1
<211> LENGTH: 406
<212> TYPE: PRT
<213> ORGANISM: Homo sapiens
<220> FEATURE:
<221> NAME/KEY: MISC_FEATURE
<222> LOCATION: (1)..(406)
<223> OTHER INFORMATION: Xaa= 4-carboxyglutamic acid
      (gamma-carboxyglutamate)

<400> SEQUENCE: 1

Ala Asn Ala Phe Leu Xaa Xaa Leu Arg Pro Gly Ser Leu Xaa Arg Xaa
1               5                   10                  15

Cys Lys Xaa Xaa Gln Cys Ser Phe Xaa Xaa Ala Arg Xaa Ile Phe Lys
            20                  25                  30

Asp Ala Xaa Arg Thr Lys Leu Phe Trp Ile Ser Tyr Ser Asp Gly Asp
        35                  40                  45

Gln Cys Ala Ser Ser Pro Cys Gln Asn Gly Gly Ser Cys Lys Asp Gln
    50                  55                  60

Leu Gln Ser Tyr Ile Cys Phe Cys Leu Pro Ala Phe Glu Gly Arg Asn
65                  70                  75                  80

Cys Glu Thr His Lys Asp Asp Gln Leu Ile Cys Val Asn Glu Asn Gly
                85                  90                  95

Gly Cys Glu Gln Tyr Cys Ser Asp His Thr Gly Thr Lys Arg Ser Cys
            100                 105                 110

Arg Cys His Glu Gly Tyr Ser Leu Leu Ala Asp Gly Val Ser Cys Thr
        115                 120                 125

Pro Thr Val Glu Tyr Pro Cys Gly Lys Ile Pro Ile Leu Glu Lys Arg
    130                 135                 140

Asn Ala Ser Lys Pro Gln Gly Arg Ile Val Gly Gly Lys Val Cys Pro
145                 150                 155                 160
```

-continued

```
Lys Gly Glu Cys Pro Trp Gln Val Leu Leu Leu Val Asn Gly Ala Gln
            165                 170                 175

Leu Cys Gly Gly Thr Leu Ile Asn Thr Ile Trp Val Val Ser Ala Ala
            180                 185                 190

His Cys Phe Asp Lys Ile Lys Asn Trp Arg Asn Leu Ile Ala Val Leu
            195                 200                 205

Gly Glu His Asp Leu Ser Glu His Asp Gly Asp Glu Gln Ser Arg Arg
            210                 215                 220

Val Ala Gln Val Ile Ile Pro Ser Thr Tyr Val Pro Gly Thr Thr Asn
225                     230                 235                 240

His Asp Ile Ala Leu Leu Arg Leu His Gln Pro Val Val Leu Thr Asp
                245                 250                 255

His Val Val Pro Leu Cys Leu Pro Glu Arg Thr Phe Ser Glu Arg Thr
                260                 265                 270

Leu Ala Phe Val Arg Phe Ser Leu Val Ser Gly Trp Gly Gln Leu Leu
                275                 280                 285

Asp Arg Gly Ala Thr Ala Leu Glu Leu Met Val Leu Asn Val Pro Arg
        290                 295                 300

Leu Met Thr Gln Asp Cys Leu Gln Gln Ser Arg Lys Val Gly Asp Ser
305                 310                 315                 320

Pro Asn Ile Thr Glu Tyr Met Phe Cys Ala Gly Tyr Ser Asp Gly Ser
                325                 330                 335

Lys Asp Ser Cys Lys Gly Asp Ser Gly Gly Pro His Ala Thr His Tyr
                340                 345                 350

Arg Gly Thr Trp Tyr Leu Thr Gly Ile Val Ser Trp Gly Gln Gly Cys
            355                 360                 365

Ala Thr Val Gly His Phe Gly Val Tyr Thr Arg Val Ser Gln Tyr Ile
            370                 375                 380

Glu Trp Leu Gln Lys Leu Met Arg Ser Glu Pro Arg Pro Gly Val Leu
385                 390                 395                 400

Leu Arg Ala Pro Phe Pro
                405
```

COAGULATION FACTOR VII POLYPEPTIDES

CROSS-REFERENCE TO RELATED APPLICATIONS

This application is a Continuation of U.S. application Ser. No. 11/367,189 filed Mar. 3, 2006, now abandoned, which is a Continuation of International Patent Application PCT/DK2004/000594 (published as WO 2005/024006), filed Sep. 9, 2004, which claimed priority of Danish Patent Application PA 2003 01296, filed Sep. 9, 2003; this application further claims priority under 35 U.S.C. §119 of U.S. Provisional Application 60/503,418, filed Sep. 16, 2003.

FIELD OF THE INVENTION

The present invention relates to novel human coagulation Factor VII polypeptides, as well as polynucleotide constructs encoding such polypeptides, vectors and host cells comprising and expressing the polynucleotide, pharmaceutical compositions comprising Factor VII polypeptides, uses and methods of treatment.

INCORPORATION-BY-REFERENCE OF THE SEQUENCE LISTING

In accordance with 37 C.F.R. §1.52(e)(5), Applicants enclose herewith the Sequence Listing for the above-captioned application entitled "SEQUENCE LISTING", created on Apr. 16, 2010. The Sequence Listing is made up of 4 kilobytes, and the information contained in the attached "SEQUENCE LISTING" is identical to the information in the specification as originally filed. No new matter is added.

BACKGROUND OF THE INVENTION

Blood coagulation is a process consisting of a complex interaction of various blood components (or factors) that eventually gives rise to a fibrin clot. Generally, the blood components, which participate in what has been referred to as the coagulation "cascade", are enzymatically inactive proteins (proenzymes or zymogens) that are converted to proteolytic enzymes by the action of an activator (which itself is an activated clotting factor). Coagulation factors that have undergone such a conversion are generally referred to as "active factors", and are designated by the addition of the letter "a" to the name of the coagulation factor (e.g. Factor VIIa).

Initiation of the haemostatic process is mediated by the formation of a complex between tissue factor, exposed as a result of injury to the vessel wall, and Factor VIIa. This complex then converts Factors IX and X to their active forms. Factor Xa converts limited amounts of prothrombin to thrombin on the tissue factor-bearing cell. Thrombin activates platelets and Factors V and VIII into Factors Va and VIIIa, both cofactors in the further process leading to the full thrombin burst. This process includes generation of Factor Xa by Factor IXa (in complex with factor VIIIa) and occurs on the surface of activated platelets. Thrombin finally converts fibrinogen to fibrin resulting in formation of a fibrin clot.

Factor VII is a trace plasma glycoprotein that circulates in blood as a single-chain zymogen. The zymogen is catalytically inactive. Single-chain Factor VII may be converted to two-chain Factor VIIa by Factor Xa, Factor XIIa, Factor IXa, Factor VIIa or thrombin in vitro. Factor Xa is believed to be the major physiological activator of Factor VII. The conversion of zymogen Factor VII into the activated two-chain molecule occurs by cleavage of an internal $Arg_{152}$-$Ile_{153}$ peptide bond.

It is often desirable to stimulate the coagulation cascade in a subject. Factor VIIa has been used to control bleeding disorders that have several causes such as clotting factor deficiencies (e.g. haemophilia A and B or deficiency of coagulation Factors XI or VII) or clotting factor inhibitors. Factor VIIa has also been used to control excessive bleeding occurring in subjects with a normally functioning blood clotting cascade (no clotting factor deficiencies or inhibitors against any of the coagulation factors). Such bleeding may, for example, be caused by a defective platelet function, thrombocytopenia or von Willebrand's disease. Bleeding is also a major problem in connection with surgery and other forms of tissue damage.

European Patent No. 200,421 (ZymoGenetics) relates to the nucleotide sequence encoding human Factor VII and the recombinant expression of Factor VII in mammalian cells.

Dickinson et al. (*Proc. Natl. Acad. Sci. USA* 93, 14379-14384, 1996) discloses Factor VII polypeptides wherein certain amino acids have been individually replaced by Ala. Iwanaga et al. (*Thromb. Haemost.* (supplement august 1999), 466, abstract 1474) relates to Factor VIIa variants wherein residues 316-320 are deleted or residues 311-322 are replaced with the corresponding residues from trypsin.

There is still a need in the art for improved Factor VII polypeptides having procoagulant activity. In particular, there is a need for Factor VII polypeptides with increased TF independent activity.

SUMMARY OF THE INVENTION

The present invention relates to Factor VII polypeptides with increased TF independent activity, such as novel coagulation Factor VII polypeptides with the same or increased activity compared to wild type Factor VIIa and with a Tissue Factor binding affinity lower than recombinant wild type human Factor VIIa.

In a first aspect, the present invention relates to a Factor VII polypeptide with a Tissue Factor binding affinity lower than recombinant wild type human Factor VIIa and substantially the same activity or increased activity compared to recombinant wild type human Factor VIIa with the proviso that the Factor VII polypeptide is not I69A-FVII.

In a second aspect, the invention relates to a composition comprising a Factor VII polypeptide with a Tissue Factor binding affinity lower than recombinant wild type human Factor VIIa and substantially the same activity or increased activity compared to recombinant wild type human Factor VIIa with the proviso that the Factor VII polypeptide is not I69A-FVII.

In a third aspect, the invention relates to a pharmaceutical composition comprising a Factor VII polypeptide with a Tissue Factor binding affinity lower than recombinant wild type human Factor VIIa and substantially the same activity or increased activity compared to recombinant wild type human Factor VIIa; and optionally, a pharmaceutically acceptable carrier.

In a further aspect, the invention relates to a polynucleotide construct encoding a Factor VII polypeptide with a Tissue Factor binding affinity lower than recombinant wild type human Factor VIIa and substantially the same activity or increased activity compared to recombinant wild type human Factor VIIa with the proviso that the Factor VII polypeptide is not I69A-FVII.

In a further aspect, the invention relates to a eukaryotic host cell comprising a polynucleotide construct encoding a Factor VII polypeptide with a Tissue Factor binding affinity lower than recombinant wild type human Factor VIIa and substantially the same activity or increased activity compared to recombinant wild type human Factor VIIa with the proviso that the Factor VII polypeptide is not I69A-FVII.

In a further aspect, the invention relates to a method for producing a Factor VII polypeptide with a Tissue Factor binding affinity lower than recombinant wild type human Factor VIIa and substantially the same activity or increased activity compared to recombinant wild type human Factor VIIa with the proviso that the Factor VII polypeptide is not I69A-FVII, the method comprising cultivating a eukaryotic host cell comprising a polynucleotide construct encoding the Factor VII polypeptide in an appropriate growth medium under conditions allowing protein synthesis from said polynucleotide construct and recovering said Factor VII polypeptide from the culture medium.

In a further aspect, the invention relates to a use of a Factor VII polypeptide with a Tissue Factor binding affinity lower than recombinant wild type human Factor VIIa and substantially the same activity or increased activity compared to recombinant wild type human Factor VIIa; for the preparation of a medicament for the treatment of bleeding episodes or for the enhancement of the normal haemostatic system.

In a further aspect, the invention relates to a method for the treatment of bleeding episodes or bleeding disorders in a subject or for the enhancement of the normal haemostatic system, the method comprising administering to a subject in need thereof a therapeutically or prophylactically effective amount of a Factor VII polypeptide with a Tissue Factor binding affinity lower than recombinant wild type human Factor VIIa and substantially the same activity or increased activity compared to recombinant wild type human Factor VIIa.

In a further aspect, the invention relates to a Factor VII polypeptide with a Tissue Factor binding affinity lower than recombinant wild type human Factor VIIa and substantially the same activity or increased activity compared to recombinant wild type human Factor VIIa, wherein said Factor VII polypeptide is selected from:
  i) a Factor VII polypeptide comprising one or more amino acid substitution selected from $K18X_1$, $R36X_2$, $S43X_3$, $K62X_4$, $Q64X_5$, $L65X_6$, $I69X_7$, $F71X_8$, $L73X_9$, $P74X_{10}$, $E77X_{11}$, $G78X_{12}$, $R79X_{13}$, $K85X_{14}$, $Q88X_{15}$, $N93X_{16}$, $F275X_{17}$, $R277X_{18}$, $M306X_{19}$, $T307X_{20}$, $Q308X_{21}$, $D309X_{22}$, or $R379X_{23}$ corresponding to amino acids at positions of SEQ ID NO: 1, which different amino acid decreases the Tissue Factor binding affinity,
  wherein
  $X_1$ is E, D, A, or F;
  $X_2$ is E, D, K, A, F, or N;
  $X_3$ is E, D, K, R, A, or F;
  $X_4$ is D, A, or F;
  $X_5$ is E, D, K, R, A, F, or N;
  $X_6$ is E, D, K, R, A, or F;
  $X_7$ is C, D, E, F, G, H, K, L, M, N, P, Q, R, S, T, V, W, or Y;
  $X_8$ is A, G, H, I, K, L, M, P, R, S, T, V, or W;
  $X_9$ is A, D, E, F, G, H, I, K, M, N, P, Q, R, S, T, V, W, or Y;
  $X_{10}$ is A, D, E, F, G, H, I, K, L, M, N, Q, R, S, T, V, W, or Y;
  $X_{11}$ is A, F, G, H, I, K, L, M, N, P, Q, R, S, T, V, W, or Y;
  $X_{12}$ is A, D, E, F, H, I, K, L, M, N, P, Q, R, S, T, V, W, or Y;
  $X_{13}$ is A, D, E, F, G, H, I, K, L, M, N, P, Q, S, T, V, W, or Y;
  $X_{14}$ is A, D, E, F, G, I, L, M, P, S, T, V, W, or Y;
  $X_{15}$ is A, D, E, F, G, H, I, K, L, M, N, P, R, S, T, V, W, or Y;
  $X_{16}$ is A, D, E, F, G, H, I, K, L, M, P, Q, R, S, T, V, W, or Y;
  $X_{17}$ is A, D, E, G, I, K, L, M, N, P, Q, R, S, T, V, W, or Y;
  $X_{18}$ is A, D, E, F, G, H, I, K, L, M, P, Q, S, T, V, W, or Y;
  $X_{19}$ is A, E, F, G, H, I, K, L, P, Q, R, S, T, V, W, or Y;
  $X_{20}$ is A, D, E, F, G, H, I, K, L, M, N, P, Q, R, S, V, W, or Y;
  $X_{21}$ is A, D, E, F, G, H, I, K, L, M, N, P, R, S, T, V, W, or Y;
  $X_{22}$ is A, F, G, H, I, K, L, M, N, P, Q, R, V, W, or Y; and
  $X_{23}$ is A, D, E, F, G, H, I, K, L, M, P, Q, S, T, V, W, or Y;
  and/or
  ii) a Factor VII polypeptide, wherein one or more amino acid corresponding to amino acids at positions selected from K18, R36, K62, Q64, L65, I69, F71, L73, P74, E77, G78, R79, K85, Q88, N93, F275, R277, M306, Q308, D309, or R379 of SEQ ID NO: 1 have been substituted with a cysteine amino acid residue, which cysteine amino acid residue decreases the Tissue Factor binding affinity, and which cysteine amino acid residue is optionally conjugated with a chemical group, which chemical group increases the molecular weight of said Factor VII polypeptide;
  and/or
  iii) a Factor VII polypeptide comprising one or more N-glycosylation site N-Xaa-S/T introduced by amino acid substitutions corresponding to amino acids starting at positions selected from R36, Q64, I69, F71, P74, E77, G78, Q88, N93, F275, M306, T307, or D309 of SEQ ID NO: 1, wherein Xaa is any amino acid except P, which introduced N-glycosylation site decreases the Tissue Factor binding affinity.

In a further aspect, the invention relates to a composition comprising a Factor VII polypeptide with a Tissue Factor binding affinity lower than recombinant wild type human Factor VIIa and substantially the same activity or increased activity compared to recombinant wild type human Factor VIIa, wherein said Factor VII polypeptide is selected from:
  i) a Factor VII polypeptide comprising one or more amino acid substitution selected from $K18X_1$, $R36X_2$, $S43X_3$, $K62X_4$, $Q64X_5$, $L65X_6$, $I69X_7$, $F71X_8$, $L73X_9$, $P74X_{10}$, $E77X_{11}$, $G78X_{12}$, $R79X_{13}$, $K85X_{14}$, $Q88X_{15}$, $N93X_{16}$, $F275X_{17}$, $R277X_{18}$, $M306X_{19}$, $T307X_{20}$, $Q308X_{21}$, $D309X_{22}$, or $R379X_{23}$ corresponding to amino acids at positions of SEQ ID NO: 1, which different amino acid decreases the Tissue Factor binding affinity,
  wherein
  $X_1$ is E, D, A, or F;
  $X_2$ is E, D, K, A, F, or N;
  $X_3$ is E, D, K, R, A, or F;
  $X_4$ is D, A, or F;
  $X_5$ is E, D, K, R, A, F, or N;
  $X_6$ is E, D, K, R, A, or F;
  $X_7$ is C, D, E, F, G, H, K, L, M, N, P, Q, R, S, T, V, W, or Y;
  $X_8$ is A, G, H, I, K, L, M, P, R, S, T, V, or W,
  $X_9$ is A, D, E, F, G, H, I, K, M, N, P, Q, R, S, T, V, W, or Y;
  $X_{10}$ is A, D, E, F, G, H, I, K, L, M, N, Q, R, S, T, V, W, or Y;
  $X_{11}$ is A, F, G, H, I, K, L, M, N, P, Q, R, S, T, V, W, or Y;
  $X_{12}$ is A, D, E, F, H, I, K, L, M, N, P, Q, R, S, T, V, W, or Y;
  $X_{13}$ is A, D, E, F, G, H, I, K, L, M, N, P, Q, S, T, V, W, or Y;
  $X_{14}$ is A, D, E, F, G, I, L, M, P, S, T, V, W, or Y;
  $X_{15}$ is A, D, E, F, G, H, I, K, L, M, N, P, R, S, T, V, W, or Y;
  $X_{16}$ is A, D, E, F, G, H, I, K, L, M, P, Q, R, S, T, V, W, or Y;
  $X_{17}$ is A, D, E, G, I, K, L, M, N, P, Q, R, S, T, V, W, or Y;
  $X_{18}$ is A, D, E, F, G, H, I, K, L, M, P, Q, S, T, V, W, or Y;
  $X_{19}$ is A, E, F, G, H, I, K, L, P, Q, R, S, T, V, W, or Y;
  $X_{20}$ is A, D, E, F, G, H, I, K, L, M, N, P, Q, R, S, V, W, or Y;
  $X_{21}$ is A, D, E, F, G, H, I, K, L, M, N, P, R, S, T, V, W, or Y;
  $X_{22}$ is A, F, G, H, I, K, L, M, N, P, Q, R, V, W, or Y; and
  $X_{23}$ is A, D, E, F, G, H, I, K, L, M, P, Q, S, T, V, W, or Y;
  and/or
  ii) a Factor VII polypeptide, wherein one or more amino acid corresponding to amino acids at positions selected from K18, R36, K62, Q64, L65, I69, F71, L73, P74, E77, G78, R79, K85, Q88, N93, F275, R277, M306, Q308, D309, or R379 of SEQ ID NO: 1 have been substituted with a cysteine amino acid residue, which cysteine amino acid residue decreases the Tissue Factor binding affinity, and which cysteine amino acid residue is optionally conjugated with a chemical group, which chemical group increases the molecular weight of said Factor VII polypeptide;

and/or iii) a Factor VII polypeptide comprising one or more N-glycosylation site N-Xaa-S/T introduced by amino acid substitutions corresponding to amino acids starting at positions selected from R36, Q64, I69, F71, P74, E77, G78, Q88, N93, F275, M306, T307, or D309 of SEQ ID NO: 1, wherein Xaa is any amino acid except P, which introduced N-glycosylation site decreases the Tissue Factor binding affinity.

In a further aspect, the invention relates to a pharmaceutical composition comprising a Factor VII polypeptide with a Tissue Factor binding affinity lower than recombinant wild type human Factor VIIa and substantially the same activity or increased activity compared to recombinant wild type human Factor VIIa, wherein said Factor VII polypeptide is selected from:

i) a Factor VII polypeptide comprising one or more amino acid substitution selected from $K18X_1$, $R36X_2$, $S43X_3$, $K62X_4$, $Q64X_5$, $L65X_6$, $I69X_7$, $F71X_8$, $L73X_9$, $P74X_{10}$, $E77X_{11}$, $G78X_{12}$, $R79X_{13}$, $K85X_{14}$, $Q88X_{15}$, $N93X_{16}$, $F275X_{17}$, $R277X_{18}$, $M306X_{19}$, $T307X_{20}$, $Q308X_{21}$, $D309X_{22}$, or $R379X_{23}$ corresponding to amino acids at positions of SEQ ID NO: 1, which different amino acid decreases the Tissue Factor binding affinity, wherein $X_1$ is E, D, A, or F;
$X_2$ is E, D, K, A, F, or N;
$X_3$ is E, D, K, R, A, or F;
$X_4$ is D, A, or F;
$X_5$ is E, D, K, R, A, F, or N;
$X_6$ is E, D, K, R, A, or F;
$X_7$ is C, D, E, F, G, H, K, L, M, N, P, Q, R, S, T, V, W, or Y;
$X_8$ is A, G, H, I, K, L, M, P, R, S, T, V, or W;
$X_9$ is A, D, E, F, G, H, I, K, M, N, P, Q, R, S, T, V, W, or Y;
$X_{10}$ is A, D, E, F, G, H, I, K, L, M, N, Q, R, S, T, V, W, or Y;
$X_{11}$ is A, F, G, H, I, K, L, M, N, P, Q, R, S, T, V, W, or Y;
$X_{12}$ is A, D, E, F, H, I, K, L, M, N, P, Q, R, S, T, V, W, or Y;
$X_{13}$ is A, D, E, F, G, H, I, K, L, M, N, P, Q, S, T, V, W, or Y;
$X_{14}$ is A, D, E, F, G, I, L, M, P, S, T, V, W, or Y;
$X_{15}$ is A, D, E, F, G, H, I, K, L, M, N, P, R, S, T, V, W, or Y;
$X_{16}$ is A, D, E, F, G, H, I, K, L, M, P, Q, R, S, T, V, W, or Y;
$X_{17}$ is A, D, E, G, I, K, L, M, N, P, Q, R, S, T, V, W, or Y;
$X_{18}$ is A, D, E, F, G, H, I, K, L, M, P, Q, S, T, V, W, or Y;
$X_{19}$ is A, E, F, G, H, I, K, L, P, Q, R, S, T, V, W, or Y;
$X_{20}$ is A, D, E, F, G, H, I, K, L, M, N, P, Q, R, S, V, W, or Y;
$X_{21}$ is A, D, E, F, G, H, I, K, L, M, N, P, R, S, T, V, W, or Y;
$X_{22}$ is A, F, G, H, I, K, L, M, N, P, Q, R, V, W, or Y; and
$X_{23}$ is A, D, E, F, G, H, I, K, L, M, P, Q, S, T, V, W, or Y;

and/or ii) a Factor VII polypeptide, wherein one or more amino acid corresponding to amino acids at positions selected from K18, R36, K62, Q64, L65, I69, F71, L73, P74, E77, G78, R79, K85, Q88, N93, F275, R277, M306, Q308, D309, or R379 of SEQ ID NO: 1 have been substituted with a cysteine amino acid residue, which cysteine amino acid residue decreases the Tissue Factor binding affinity, and which cysteine amino acid residue is optionally conjugated with a chemical group, which chemical group increases the molecular weight of said Factor VII polypeptide;

and/or iii) a Factor VII polypeptide comprising one or more N-glycosylation site N-Xaa-S/T introduced by amino acid substitutions corresponding to amino acids starting at positions selected from R36, Q64, I69, F71, P74, E77, G78, Q88, N93, F275, M306, T307, or D309 of SEQ ID NO: 1, wherein Xaa is any amino acid except P, which introduced N-glycosylation site decreases the Tissue Factor binding affinity;

and optionally, a pharmaceutically acceptable carrier.

In a further aspect, the invention relates to a use of a Factor VII polypeptide with a Tissue Factor binding affinity lower than recombinant wild type human Factor VIIa and substantially the same activity or increased activity compared to recombinant wild type human Factor VIIa, wherein said Factor VII polypeptide is selected from:

i) a Factor VII polypeptide comprising one or more amino acid substitution selected from $K18X_1$, $R36X_2$, $543X_3$, $K62X_4$, $Q64X_5$, $L65X_6$, $I69X_7$, $F71X_8$, $L73X_9$, $P74X_{10}$, $E77X_{11}$, $G78X_{12}$, $R79X_{13}$, $K85X_{14}$, $Q88X_{15}$, $N93X_{16}$, $F275X_{17}$, $R277X_{18}$, $M306X_{19}$, $T307X_{20}$, $Q308X_{21}$, $D309X_{22}$, or $R379X_{23}$ corresponding to amino acids at positions of SEQ ID NO: 1, which different amino acid decreases the Tissue Factor binding affinity, wherein $X_1$ is E, D, A, or F;
$X_2$ is E, D, K, A, F, or N;
$X_3$ is E, D, K, R, A, or F;
$X_4$ is D, A, or F;
$X_5$ is E, D, K, R, A, F, or N;
$X_6$ is E, D, K, R, A, or F;
$X_7$ is C, D, E, F, G, H, K, L, M, N, P, Q, R, S, T, V, W, or Y;
$X_8$ is A, G, H, I, K, L, M, P, R, S, T, V, or W;
$X_9$ is A, D, E, F, G, H, I, K, M, N, P, Q, R, S, T, V, W, or Y;
$X_{10}$ is A, D, E, F, G, H, I, K, L, M, N, Q, R, S, T, V, W, or Y;
$X_{11}$ is A, F, G, H, I, K, L, M, N, P, Q, R, S, T, V, W, or Y;
$X_{12}$ is A, D, E, F, H, I, K, L, M, N, P, Q, R, S, T, V, W, or Y;
$X_{13}$ is A, D, E, F, G, H, I, K, L, M, N, P, Q, S, T, V, W, or Y;
$X_{14}$ is A, D, E, F, G, I, L, M, P, S, T, V, W, or Y;
$X_{15}$ is A, D, E, F, G, H, I, K, L, M, N, P, R, S, T, V, W, or Y;
$X_{16}$ is A, D, E, F, G, H, I, K, L, M, P, Q, R, S, T, V, W, or Y;
$X_{17}$ is A, D, E, G, I, K, L, M, N, P, Q, R, S, T, V, W, or Y;
$X_{18}$ is A, D, E, F, G, H, I, K, L, M, P, Q, S, T, V, W, or Y;
$X_{19}$ is A, E, F, G, H, I, K, L, P, Q, R, S, T, V, W, or Y;
$X_{20}$ is A, D, E, F, G, H, I, K, L, M, N, P, Q, R, S, V, W, or Y;
$X_{21}$ is A, D, E, F, G, H, I, K, L, M, N, P, R, S, T, V, W, or Y;
$X_{22}$ is A, F, G, H, I, K, L, M, N, P, Q, R, V, W, or Y; and
$X_{23}$ is A, D, E, F, G, H, I, K, L, M, P, Q, S, T, V, W, or Y;

and/or ii) a Factor VII polypeptide, wherein one or more amino acid corresponding to amino acids at positions selected from K18, R36, K62, Q64, L65, I69, F71, L73, P74, E77, G78, R79, K85, Q88, N93, F275, R277, M306, Q308, D309, or R379 of SEQ ID NO: 1 have been substituted with a cysteine amino acid residue, which cysteine amino acid residue decreases the Tissue Factor binding affinity, and which cysteine amino acid residue is optionally conjugated with a chemical group, which chemical group increases the molecular weight of said Factor VII polypeptide;

and/or iii) a Factor VII polypeptide comprising one or more N-glycosylation site N-Xaa-S/T introduced by amino acid substitutions corresponding to amino acids starting at positions selected from R36, Q64, I69, F71, P74, E77, G78, Q88, N93, F275, M306, T307, or D309 of SEQ ID NO: 1, wherein Xaa is any amino acid except P, which introduced N-glycosylation site decreases the Tissue Factor binding affinity;

for the preparation of a medicament for the treatment of bleeding episodes or for the enhancement of the normal haemostatic system.

In a further aspect, the invention relates to a method for the treatment of bleeding episodes or bleeding disorders in a subject or for the enhancement of the normal haemostatic system, the method comprising administering to a subject in need thereof a therapeutically or prophylactically effective amount of a Factor VII polypeptide with a Tissue Factor binding affinity lower than recombinant wild type human Factor VIIa and substantially the same activity or increased activity compared to recombinant wild type human Factor VIIa, wherein said Factor VII polypeptide is selected from:

i) a Factor VII polypeptide comprising one or more amino acid substitution selected from $K18X_1$, $R36X_2$, $S43X_3$, $K62X_4$, $Q64X_5$, $L65X_6$, $I69X_7$, $F71X_8$, $L73X_9$, $P74X_{10}$, $E77X_{11}$, $G78X_{12}$, $R79X_{13}$, $K85X_{14}$, $Q88X_{15}$, $N93X_{16}$, $F275X_{17}$, $R277X_{18}$, $M306X_{19}$, $T307X_{20}$, $Q308X_{21}$, $D309X_{22}$, or $R379X_{23}$ corresponding to amino acids at positions of SEQ ID NO: 1, which different amino acid decreases the Tissue Factor binding affinity, wherein $X_1$ is E, D, A, or F;
$X_2$ is E, D, K, A, F, or N;
$X_3$ is E, D, K, R, A, or F;
$X_4$ is D, A, or F;
$X_5$ is E, D, K, R, A, F, or N;
$X_6$ is E, D, K, R, A, or F;
$X_7$ is C, D, E, F, G, H, K, L, M, N, P, Q, R, S, T, V, W, or Y;
$X_8$ is A, G, H, I, K, L, M, P, R, S, T, V, or W;
$X_9$ is A, D, E, F, G, H, I, K, M, N, P, Q, R, S, T, V, W, or Y;
$X_{10}$ is A, D, E, F, G, H, I, K, L, M, N, Q, R, S, T, V, W, or Y;
$X_{11}$ is A, F, G, H, I, K, L, M, N, P, Q, R, S, T, V, W, or Y;
$X_{12}$ is A, D, E, F, H, I, K, L, M, N, P, Q, R, S, T, V, W, or Y;
$X_{13}$ is A, D, E, F, G, H, I, K, L, M, N, P, Q, S, T, V, W, or Y;
$X_{14}$ is A, D, E, F, G, I, L, M, P, S, T, V, W, or Y;
$X_{15}$ is A, D, E, F, G, H, I, K, L, M, N, P, R, S, T, V, W, or Y;
$X_{16}$ is A, D, E, F, G, H, I, K, L, M, P, Q, R, S, T, V, W, or Y;
$X_{17}$ is A, D, E, G, I, K, L, M, N, P, Q, R, S, T, V, W, or Y;
$X_{18}$ is A, D, E, F, G, H, I, K, L, M, P, Q, S, T, V, W, or Y;
$X_{19}$ is A, E, F, G, H, I, K, L, P, Q, R, S, T, V, W, or Y;
$X_{20}$ is A, D, E, F, G, H, I, K, L, M, N, P, Q, R, S, V, W, or Y;
$X_{21}$ is A, D, E, F, G, H, I, K, L, M, N, P, R, S, T, V, W, or Y;
$X_{22}$ is A, F, G, H, I, K, L, M, N, P, Q, R, V, W, or Y; and
$X_{23}$ is A, D, E, F, G, H, I, K, L, M, P, Q, S, T, V, W, or Y;

and/or ii) a Factor VII polypeptide, wherein one or more amino acid corresponding to amino acids at positions selected from K18, R36, K62, Q64, L65, I69, F71, L73, P74, E77, G78, R79, K85, Q88, N93, F275, R277, M306, Q308, D309, or R379 of SEQ ID NO: 1 have been substituted with a cysteine amino acid residue, which cysteine amino acid residue decreases the Tissue Factor binding affinity, and which cysteine amino acid residue is optionally conjugated with a chemical group, which chemical group increases the molecular weight of said Factor VII polypeptide;

and/or iii) a Factor VII polypeptide comprising one or more N-glycosylation site N-Xaa-S/T introduced by amino acid substitutions corresponding to amino acids starting at positions selected from R36, Q64, I69, F71, P74, E77, G78, Q88, N93, F275, M306, T307, or D309 of SEQ ID NO: 1, wherein Xaa is any amino acid except P, which introduced N-glycosylation site decreases the Tissue Factor binding affinity.

In a further aspect the present invention relates to a composition comprising wild type human FVIIa and a Factor VII polypeptide with a Tissue Factor binding affinity lower than recombinant wild type human Factor VIIa and substantially the same activity or increased activity compared to recombinant wild type human Factor VIIa.

In a further aspect the present invention relates to a method for the treatment of bleeding episodes in a subject or for the enhancement of the normal haemostatic system, the method comprising administering to a subject in need thereof a therapeutically or prophylactically effective amount of:

a) composition comprising wild type human FVIIa and a Factor VII polypeptide with a Tissue Factor binding affinity lower than recombinant wild type human Factor VIIa and substantially the same activity or increased activity compared to recombinant wild type human Factor VIIa; or b) a first composition comprising wild type human FVIIa and a second composition comprising a Factor VII polypeptide with a Tissue Factor binding affinity lower than recombinant wild type human Factor VIIa and substantially the same activity or increased activity compared to recombinant wild type human Factor VIIa.

In a further aspect the present invention relates to a process for preparing a composition comprising wild type human FVIIa and a Factor VII polypeptide with a Tissue Factor binding affinity lower than recombinant wild type human Factor VIIa and substantially the same activity or increased activity compared to recombinant wild type human Factor VIIa, wherein the process comprises the step of: mixing wild type human FVIIa with a Factor VII polypeptide with a Tissue Factor binding affinity lower than recombinant wild type human Factor VIIa and substantially the same activity or increased activity compared to recombinant wild type human Factor VIIa in an aqueous medium.

In a further aspect the present invention relates to a use of a composition comprising wild type human FVIIa and a Factor VII polypeptide with a Tissue Factor binding affinity lower than recombinant wild type human Factor VIIa and substantially the same activity or increased activity compared to recombinant wild type human Factor VIIa, for the preparation of a medicament for the treatment of bleeding episodes in a subject or for the enhancement of the normal haemostatic system.

BRIEF DESCRIPTION OF THE DRAWINGS

FIG. 2 The full amino acid sequence of native (wild type) human coagulation Factor VII (SEQ ID NO:1).

DETAILED DESCRIPTION OF THE INVENTION

Figure 1:
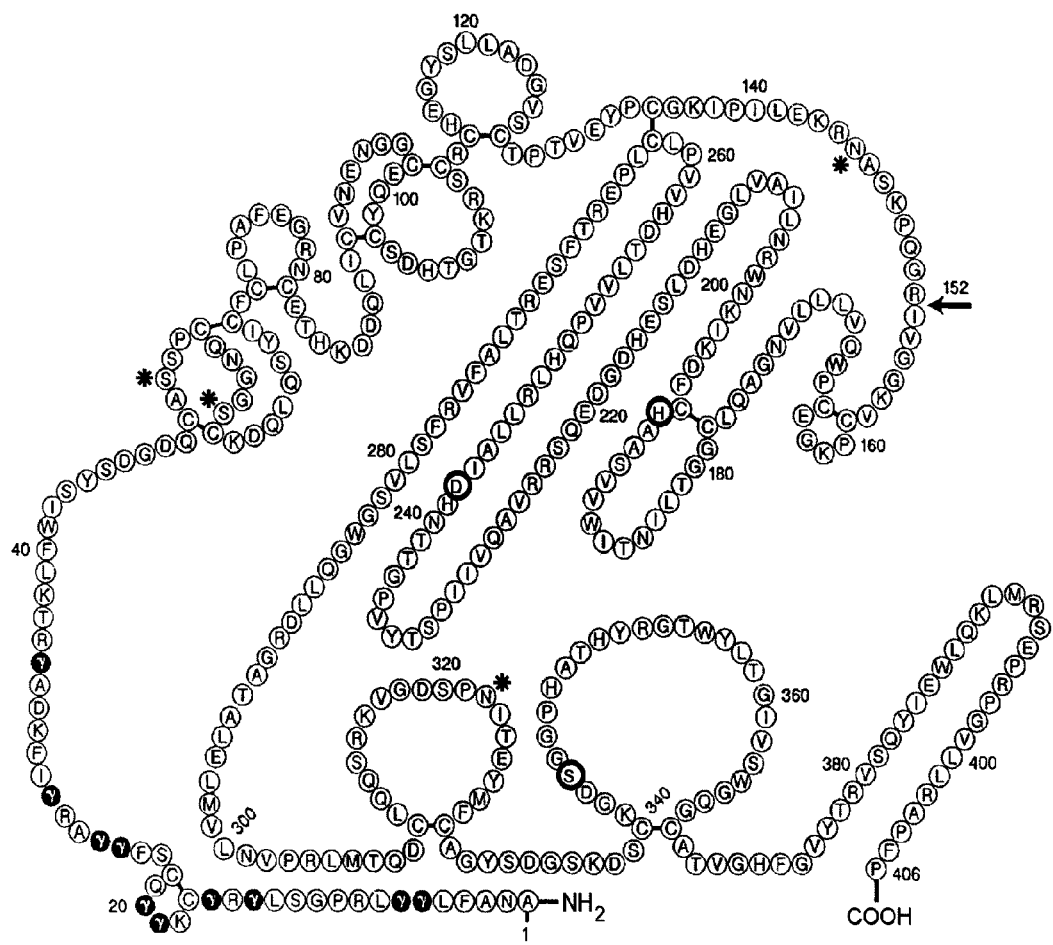
FIG. 1 The structure of correctly processed human coagulation Factor VII, amino acids 1 to 406, with gamma carboxylated Glu-residues (γ) and glycosylation (*). The arrow at amino acid residue 152 shows the site where single-chain Factor VII is cleaved to be converted to activated two-chain Factor VII (FVIIa).

The present invention relates to novel coagulation Factor VII polypeptides with substantially the same or increased activity compared to wild type Factor VIIa and with a Tissue Factor binding affinity lower than recombinant wild type human Factor VIIa. Increasing evidence suggests that therapeutic treatment with recombinant wild type human coagulation Factor VII works by a TF independent mechanism involving binding of FVII directly to activated thrombocytes and a generation of activated Factor Xa and eventually fibrin locally at the place of tissue damage. The Factor VII polypeptides of the present invention provide an alternative to traditional TF binding Factor VII polypeptides. Factor VII polypeptides that do not bind to TF may be an advantage in the therapeutic treatment of bleedings, when the exposure of TF is high, e.g. plaque rupture or sepsis. As used herein, Factor VII activity refers to its ability to promote blood clotting, which may be assessed, e.g., by measuring hydrolytic or proteolytic activity or by measuring thrombin formation.

As used herein, the terms "Factor VII polypeptide" or "FVII polypeptide" mean wild-type human Factor VII/VIIa (i.e., a polypeptide having the amino acid sequence disclosed in U.S. Pat. No. 4,784,950), as well as variants of Factor VII exhibiting substantially the same or improved biological activity relative to wild-type Factor VII, Factor VII-related polypeptides as well as Factor VII derivatives and Factor VII conjugates. Unless otherwise indicated, the term "Factor VII" is intended to encompass Factor VII polypeptides in their uncleaved (zymogen) form, as well as those that have been proteolytically processed to yield their respective bioactive forms, which may be designated Factor VIIa. Typically, Factor VII is cleaved between residues 152 and 153 to yield Factor VIIa. Such variants of Factor VII may exhibit different properties relative to human Factor VII, including stability, phospholipid binding, altered specific activity, and the like.

As used herein, "Factor VII-related polypeptides" encompasses polypeptides, including variants, in which the Factor VIIa biological activity has been substantially modified or reduced relative to the activity of wild-type Factor VIIa. These polypeptides include, without limitation, Factor VII or Factor VIIa into which specific amino acid sequence alterations have been introduced that modify or disrupt the bioactivity of the polypeptide.

The term "Factor VII derivative" as used herein, is intended to designate wild-type Factor VII, variants of Factor VII exhibiting substantially the same or improved biological activity relative to wild-type Factor VII and Factor VII-related polypeptides, in which one or more of the amino acids of the parent peptide have been chemically and/or enzymatically modified, e.g. by alkylation, glycosylation, PEGylation, acylation, ester formation or amide formation or the like. This includes but is not limited to PEGylated human Factor VIIa, cysteine-PEGylated human Factor VIIa and variants thereof.

The optional conjugation of a cysteine amino acid residue with the chemical group includes but are not limited to covalent attachment of polyethylene glycol (PEG), monomethoxy-polyethylene glycol, dextran, poly-(N-vinyl pyrrolidone) polyethylene glycol, propylene glycol homopolymers, a polypropylene oxide/ethylene oxide copolymer, polypropylene glycol, polyoxyethylated polyols (e.g., glycerol) and polyvinyl alcohol, colominic acids or other carbohydrate based polymers, polymers of amino acids, and biotin derivatives. In one embodiment of the present invention, the chemical group is a biocompatible, non-toxic, non-immunogenic and water-soluble polymer. Preferably the chemical group is water-soluble in all proportions.

Methods for attaching PEG groups to cysteine residues are described in Roberts, M. J. et al, Advanced Drug Delivery Reviews 54 (2002) 459-476.

An "N-glycosylation site" has the sequence N-Xaa-S/T, wherein Xaa is any amino acid residue except proline, N is asparagine and S/T is either serine or threonine, such as serine or threonine, such as threonine.

Specific examples of activated PEG polymers particularly preferred for coupling to cysteine residues, include the following linear PEGs: vinylsulfone-PEG (VS-PEG), such as vinylsulfone-mPEG (VS-mPEG); maleimide-PEG (MAL-PEG), such as maleimide-mPEG (MAL-mPEG) and orthopyridyl-disulfide-PEG (OPSS-PEG), such as orthopyridyl-disulfide-mPEG (OPSS-MPEG). Typically, such PEG or mPEG polymers will have a size of about 2 kDa, such as about 5 kDa, such as about 10 kD, such as about 12 kDa or such as about 20 kDa.

The skilled person will be aware that the activation method and/or conjugation chemistry to be used depends on the functional groups of the polymer (e.g. being amine, hydroxyl, carboxyl, aldehyde, sulfydryl, succinimidyl, maleimide, vinysulfone or haloacetate).

For conjugated with a chemical group to a cysteine residue (e.g. PEGylation) the FVII polypeptide is usually treated with a reducing agent, such as dithiothreitol (DDT), β-mercaptoethanol, or glutathione (γ-glutamylcysteinylglycine) prior to PEGylation, such as described in Higashi, S. Matsumoto, N., Iwanaga, S. (1997) J. Biol. Chem., 272(41), 25724-25730. The reducing agent is subsequently removed by any conventional method, such as by desalting. Conjugation of PEG to a cysteine residue typically takes place in a suitable buffer at pH 6-9 at temperatures varying from 4° C. to 25° C. for periods up to 16 hours.

In one embodiment of the present invention, an introduced cysteine residue is conjugated by mixed disulfide bond-formation with a chemical group selected from the list consisting of glutathione (gamma-glutamylcysteinylglycine), gamma-glutamylcysteine and cysteine present in the host cell or in the culture medium during production of the FVII polypeptide.

In one embodiment of the invention the chemical group is selected from the group consisting of: dendrimer, polyalkylene oxide (PAO), polyalkylene glycol (PAG), polyethylene glycol (PEG), polypropylene glycol (PPG), branched PEGs, polyvinyl alcohol (PVA), poly-carboxylate, poly-vinylpyrolidone, polyethylene-co-maleic acid anhydride, polystyrene-co-maleic acid anhydride, dextran, carboxymethyl-dextran; serum protein binding-ligands, such as compounds which bind to albumin, such as fatty acids, C5-C24 fatty acid, aliphatic diacid (e.g. C5-C24), a structure (e.g. sialic acid derivatives or mimetics) which inhibits the glycans from binding to receptors (e.g. asialoglycoprotein receptor and mannose receptor), a small organic molecule containing moieties that under physiological conditions alters charge properties, such as carboxylic acids or amines, or neutral substituents that prevent glycan specific recognition such as smaller alkyl substituents (e.g., C1-C5 alkyl), a low molecular organic charged radical (e.g. C1-C25), which may contain one or more carboxylic acids, amines sulfonic, phosphonic acids, or combination thereof; a low molecular neutral hydrophilic molecule (e.g. C1-C25), such as cyclodextrin, or a polyethylene chain which may optionally branched; polyethyleneglycol with a average molecular weight of 2-40 KDa; a well defined precission polymer such as a dendrimer with an excact molecular mass ranging from 700 to 20.000 Da, such as between 700-10.000 Da; and a substantially non-immunogenic polypeptide such as albumin or an antibody or part of an antibody optionally containing a Fc-domain.

The term "PEGylated human Factor VIIa" means human Factor VIIa, having a PEG molecule conjugated to a human Factor VIIa polypeptide. It is to be understood, that the PEG molecule may be attached to any part of the Factor VIIa polypeptide including any amino acid residue or carbohydrate moiety of the Factor VIIa polypeptide. The term "cysteine-PEGylated human Factor VIIa" means Factor VIIa having a PEG molecule conjugated to a sulfhydryl group of a cysteine introduced in human Factor VIIa.

The biological activity of Factor VIIa in blood clotting derives from its ability to (i) bind to tissue factor (TF) and (ii) catalyze the proteolytic cleavage of Factor IX or Factor X to produce activated Factor IX or X (Factor IXa or Xa, respectively). For purposes of the invention, Factor VIIa biological activity may be quantified by measuring the ability of a preparation to promote blood clotting using Factor VII-deficient plasma and thromboplastin, as described, e.g., in U.S. Pat.

No. 5,997,864. In this assay, biological activity is expressed as the reduction in clotting time relative to a control sample and is converted to "Factor VII units" by comparison with a pooled human serum standard containing 1 unit/ml Factor VII activity. Alternatively, Factor VIIa biological activity may be quantified by (i) measuring the ability of Factor VIIa to produce of Factor Xa in a system comprising TF embedded in a lipid membrane and Factor X. (Persson et al., J. Biol. Chem. 272:19919-19924, 1997); (ii) measuring Factor X hydrolysis in an aqueous system; (iii) measuring its physical binding to TF using an instrument based on surface plasmon resonance (Persson, FEBS Letts. 413:359-363, 1997) and (iv) measuring hydrolysis of a synthetic substrate.

The terms "variant" or "variants", as used herein, is intended to designate Factor VII having the sequence of SEQ ID NO:1, wherein one or more amino acids of the parent protein have been substituted by another amino acid and/or wherein one or more amino acids of the parent protein have been deleted and/or wherein one or more amino acids have been inserted in protein and/or wherein one or more amino acids have been added to the parent protein. Such addition can take place either at the N-terminal end or at the C-terminal end of the parent protein or both. The "variant" or "variants" within this definition still have FVII activity in its activated form. In one embodiment a variant is 70% identical with the sequence of SEQ ID NO:1. In one embodiment a variant is 80% identical with the sequence of SEQ ID NO:1. In another embodiment a variant is 90% identical with the sequence of SEQ ID NO:1. In a further embodiment a variant is 95% identical with the sequence of SEQ ID NO:1.

Non-limiting examples of Factor VII variants having substantially the same biological activity as wild-type Factor VII include S52A-FVIIa, S60A-FVIIa (Lino et al., Arch. Biochem. Biophys. 352: 182-192, 1998); FVIIa variants exhibiting increased proteolytic stability as disclosed in U.S. Pat. No. 5,580,560; Factor VIIa that has been proteolytically cleaved between residues 290 and 291 or between residues 315 and 316 (Mollerup et al., Biotechnol. Bioeng. 48:501-505, 1995); oxidized forms of Factor VIIa (Kornfelt et al., Arch. Biochem. Biophys. 363:43-54, 1999); FVII variants as disclosed in PCT/DK02/00189; and FVII variants exhibiting increased proteolytic stability as disclosed in WO 02/38162 (Scripps Research Institute); FVII variants having a modified Gla-domain and exhibiting an enhanced membrane binding as disclosed in WO 99/20767 (University of Minnesota) and WO 00/66753 (University of Minnesota); and FVII variants as disclosed in WO 01/58935 (Maxygen ApS), WO 03/93465 (Maxygen ApS) and WO 04/029091 (Maxygen ApS).

Non-limiting examples of FVII variants having increased biological activity compared to wild-type FVIIa include FVII variants as disclosed in WO 01/83725, WO 02/22776, WO 02/077218, PCT/DK02/00635, Danish patent application PA 2002 01423, Danish patent application PA 2001 01627; WO 02/38162 (Scripps Research Institute); and FVIIa variants with enhanced activity as disclosed in JP 2001061479 (Chemo-Sero-Therapeutic Res Inst.). Non-limiting examples of Factor VII variants having substantially reduced or modified biological activity relative to wild-type Factor VII include R152E-FVIIa (Wildgoose et al., Biochem 29:3413-3420, 1990), S344A-FVIIa (Kazama et al., J. Biol. Chem. 270:66-72, 1995), FFR-FVIIa (Hoist et al., Eur. J. Vasc. Endovasc. Surg. 15:515-520, 1998), and Factor VIIa lacking the Gla domain, (Nicolaisen et al., FEBS Letts. 317:245-249, 1993). Examples of variants of factor VII, factor VII or factor VII-related polypeptides include, without limitation, wild-type Factor VII, L305V-FVII, L305V/M306D/D309S-FVII, L305I-FVII, L305T-FVII, F374P-FVII, V158T/M298Q-FVII, V158D/E296V/M298Q-FVII, K337A-FVII, M298Q-FVII, V158D/M298Q-FVII, L305V/K337A-FVII, V158D/E296V/M298Q/L305V-FVII, V158D/E296V/M298Q/K337A-FVII, V158D/E296V/M298Q/L305V/K337A-FVII, K157A-FVII, E296V-FVII, E296V/M298Q-FVII, V158D/E296V-FVII, V158D/M298K-FVII, and S336G-FVII, L305V/K337A-FVII, L305V/V158D-FVII, L305V/E296V-FVII, L305V/M298Q-FVII, L305V/V158T-FVII, L305V/K337A/V158T-FVII, L305V/K337A/M298Q-FVII, L305V/K337A/E296V-FVII, L305V/K337A/V158D-FVII, L305V/V158D/M298Q-FVII, L305V/V158D/E296V-FVII, L305V/V158T/M298Q-FVII, L305V/V158T/E296V-FVII, L305V/E296V/M298Q-FVII, L305V/V158D/E296V/M298Q-FVII, L305V/V158T/E296V/M298Q-FVII, L305V/V158T/K337A/M298Q-FVII, L305V/V158T/E296V/K337A-FVII, L305V/V158D/K337A/M298Q-FVII, L305V/V158D/E296V/K337A-FVII, L305V/V158D/E296V/M298Q/K337A-FVII, L305V/V158T/E296V/M298Q/K337A-FVII, S314E/K316H-FVII, S314E/K316Q-FVII, S314E/L305V-FVII, S314E/K337A-FVII, S314E/V158D-FVII, S314E/E296V-FVII, S314E/M298Q-FVII, S314E/V158T-FVII, K316H/L305V-FVII, K316H/K337A-FVII, K316H/V158D-FVII, K316H/E296V-FVII, K316H/M298Q-FVII, K316H/V158T-FVII, K316Q/L305V-FVII, K316Q/K337A-FVII, K316Q/V158D-FVII, K316Q/E296V-FVII, K316Q/M298Q-FVII, K316Q/V158T-FVII, S314E/L305V/K337A-FVII, S314E/L305V/V158D-FVII, S314E/L305V/E296V-FVII, S314E/L305V/M298Q-FVII, S314E/L305V/V158T-FVII, S314E/L305V/K337A/V158T-FVII, S314E/L305V/K337A/M298Q-FVII, S314E/L305V/K337A/E296V-FVII, S314E/L305V/K337A/V158D-FVII, S314E/L305V/V158D/M298Q-FVII, S314E/L305V/V158D/E296V-FVII, S314E/L305V/V158T/M298Q-FVII, S314E/L305V/V158T/E296V-FVII, S314E/L305V/E296V/M298Q-FVII, S314E/L305V/V158D/E296V/M298Q-FVII, S314E/L305V/V158T/E296V/M298Q-FVII, S314E/L305V/V158T/K337A/M298Q-FVII, S314E/L305V/V158T/E296V/K337A-FVII, S314E/L305V/V158D/K337A/M298Q-FVII, S314E/L305V/V158D/E296V/K337A-FVII, S314E/L305V/V158D/E296V/M298Q/K337A-FVII, S314E/L305V/V158T/E296V/M298Q/K337A-FVII, K316H/L305V/K337A-FVII, K316H/L305V/V158D-FVII, K316H/L305V/E296V-FVII, K316H/L305V/M298Q-FVII, K316H/L305V/V158T-FVII, K316H/L305V/K337A/V158T-FVII, K316H/L305V/K337A/M298Q-FVII, K316H/L305V/K337A/E296V-FVII, K316H/L305V/K337A/V158D-FVII, K316H/L305V/V158D/M298Q-FVII, K316H/L305V/V158D/E296V-FVII, K316H/L305V/V158T/M298Q-FVII, K316H/L305V/V158T/E296V-FVII, K316H/L305V/E296V/M298Q-FVII, K316H/L305V/V158D/E296V/M298Q-FVII, K316H/L305V/V158T/E296V/M298Q-FVII, K316H/L305V/V158T/K337A/M298Q-FVII, K316H/L305V/V158T/E296V/K337A-FVII, K316H/L305V/V158D/K337A/M298Q-FVII, K316H/L305V/V158D/E296V/K337A-FVII, K316H/L305V/V158D/E296V/M298Q/K337A-FVII, K316H/L305V/V158T/E296V/M298Q/K337A-FVII, K316Q/L305V/K337A-FVII, K316Q/L305V/V158D-FVII, K316Q/L305V/E296V-FVII, K316Q/L305V/M298Q-FVII, K316Q/L305V/V158T-FVII, K316Q/L305V/K337A/V158T-FVII, K316Q/L305V/K337A/M298Q-FVII, K316Q/L305V/K337A/E296V-FVII, K316Q/L305V/K337A/V158D-FVII, K316Q/L305V/V158D/M298Q-FVII, K316Q/L305V/V158D/E296V-FVII, K316Q/L305V/V158T/M298Q-FVII, K316Q/L305V/V158T/E296V-FVII, K316Q/L305V/E296V/M298Q-FVII, K316Q/L305V/V158D/E296V/M298Q-FVII, K316Q/L305V/V158T/E296V/M298Q-FVII, K316Q/

L305V/V158T/K337A/M298Q-FVII, K316Q/L305V/V158T/E296V/K337A-FVII, K316Q/L305V/V158D/K337A/M298Q-FVII, K316Q/L305V/V158D/E296V/K337A-FVII, K316Q/L305V/V158D/E296V/M298Q/K337A-FVII, K316Q/L305V/V158T/E296V/M298Q/K337A-FVII, F374Y/K337A-FVII, F374Y/V158D-FVII, F374Y/E296V-FVII, F374Y/M298Q-FVII, F374Y/V158T-FVII, F374Y/S314E-FVII, F374Y/L305V-FVII, F374Y/L305V/K337A-FVII, F374Y/L305V/V158D-FVII, F374Y/L305V/E296V-FVII, F374Y/L305V/M298Q-FVII, F374Y/L305V/V158T-FVII, F374Y/L305V/S314E-FVII, F374Y/K337A/S314E-FVII, F374Y/K337A/V158T-FVII, F374Y/K337A/M298Q-FVII, F374Y/K337A/E296V-FVII, F374Y/K337A/V158D-FVII, F374Y/V158D/S314E-FVII, F374Y/V158D/M298Q-FVII, F374Y/V158D/E296V-FVII, F374Y/V158T/S314E-FVII, F374Y/V158T/M298Q-FVII, F374Y/V158T/E296V-FVII, F374Y/E296V/S314E-FVII, F374Y/S314E/M298Q-FVII, F374Y/E296V/M298Q-FVII, F374Y/L305V/K337A/V158D-FVII, F374Y/L305V/K337A/E296V-FVII, F374Y/L305V/K337A/M298Q-FVII, F374Y/L305V/K337A/V158T-FVII, F374Y/L305V/K337A/S314E-FVII, F374Y/L305V/V158D/E296V-FVII, F374Y/L305V/V158D/M298Q-FVII, F374Y/L305V/V158D/S314E-FVII, F374Y/L305V/E296V/M298Q-FVII, F374Y/L305V/E296V/V158T-FVII, F374Y/L305V/E296V/S314E-FVII, F374Y/L305V/M298Q/V158T-FVII, F374Y/L305V/M298Q/S314E-FVII, F374Y/L305V/V158T/S314E-FVII, F374Y/K337A/S314E/V158T-FVII, F374Y/K337A/S314E/M298Q-FVII, F374Y/K337A/S314E/E296V-FVII, F374Y/K337A/S314E/V158D-FVII, F374Y/K337A/V158T/M298Q-FVII, F374Y/K337A/V158T/E296V-FVII, F374Y/K337A/M298Q/E296V-FVII, F374Y/K337A/M298Q/V158D-FVII, F374Y/K337A/E296V/V158D-FVII, F374Y/V158D/S314E/M298Q-FVII, F374Y/V158D/S314E/E296V-FVII, F374Y/V158D/M298Q/E296V-FVII, F374Y/V158T/S314E/E296V-FVII, F374Y/V158T/S314E/M298Q-FVII, F374Y/V158T/M298Q/E296V-FVII, F374Y/E296V/S314E/M298Q-FVII, F374Y/L305V/M298Q/K337A/S314E-FVII, F374Y/L305V/E296V/K337A/S314E-FVII, F374Y/E296V/M298Q/K337A/S314E-FVII, F374Y/L305V/E296V/M298Q/K337A-FVII, F374Y/L305V/E296V/M298Q/S314E-FVII, F374Y/V158D/E296V/M298Q/K337A-FVII, F374Y/V158D/E296V/M298Q/S314E-FVII, F374Y/L305V/V158D/K337A/S314E-FVII, F374Y/V158D/M298Q/K337A/S314E-FVII, F374Y/V158D/E296V/K337A/S314E-FVII, F374Y/L305V/V158D/E296V/M298Q-FVII, F374Y/L305V/V158D/M298Q/K337A-FVII, F374Y/L305V/V158D/E296V/K337A-FVII, F374Y/L305V/V158D/M298Q/S314E-FVII, F374Y/L305V/V158D/E296V/S314E-FVII, F374Y/V158T/E296V/M298Q/K337A-FVII, F374Y/V158T/E296V/M298Q/S314E-FVII, F374Y/L305V/V158T/K337A/S314E-FVII, F374Y/V158T/M298Q/K337A/S314E-FVII, F374Y/V158T/E296V/K337A/S314E-FVII, F374Y/L305V/V158T/E296V/M298Q-FVII, F374Y/L305V/V158T/M298Q/K337A-FVII, F374Y/L305V/V158T/E296V/K337A-FVII, F374Y/L305V/V158T/M298Q/S314E-FVII, F374Y/L305V/V158T/E296V/S314E-FVII, F374Y/E296V/M298Q/K337A/V158T-FVII, F374Y/V158D/E296V/M298Q/K337A/S314E-FVII, F374Y/L305V/V158D/E296V/M298Q/S314E-FVII, F374Y/L305V/E296V/M298Q/V158T/S314E-FVII, F374Y/K337A/V158T/S314E-FVII, F374Y/L305V/V158D/E296V/K337A/S314E-FVII, F374Y/L305V/V158D/M298Q/K337A/S314E-FVII, F374Y/L305V/V158D/E296V/M298Q/K337A-FVII, F374Y/L305V/E296V/M298Q/K337A/S314E-FVII, F374Y/L305V/V158T/E296V/M298Q/K337A-FVII, F374Y/L305V/V158T/E296V/K337A/S314E-FVII, F374Y/L305V/V158T/E296V/M298Q/S314E-FVII, F374Y/L305V/V158T/M298Q/K337A/S314E-FVII, F374Y/V158T/E296V/M298Q/K337A/S314E-FVII, F374Y/L305V/V158T/E296V/M298Q/K337A/S314E-FVII, S52A-Factor VII, S60A-Factor VII; R152E-Factor VII, S344A-Factor VII, Factor VIIa lacking the Gla domain; and P11Q/K33E-FVII, T106N-FVII, K143N/N145T-FVII, V253N-FVII, R290N/A292T-FVII, G291N-FVII, R315N/V317T-FVII, K143N/N145T/R315N/V317T-FVII; and FVII having substitutions, additions or deletions in the amino acid sequence from 233Thr to 240Asn, FVII having substitutions, additions or deletions in the amino acid sequence from 304Arg to 329Cys.

The terminology for amino acid substitutions used is as follows. The first letter represents the amino acid naturally present at a position of human wild type FVII. The following number represents the position in human wild type FVII. The second letter represent the different amino acid substituting for (replacing) the natural amino acid. An example is M298Q, where a methionine at position 298 of human wild type FVII is replaced by a glutamine. In another example, V158T/M298Q, the valine in position 158 of human wild type FVII is replaced by a threonine and the methionine in position 298 of human wild type FVII is replaced by a Glutamine in the same Factor VII polypeptide.

In a further embodiment of the invention, the factor VII polypeptide is a polypeptide, wherein the ratio between the activity of the Factor VII polypeptide and the activity of the wild type human Factor VIIa is at least about 1.25. In one embodiment the ratio between the activity of the Factor VII polypeptide and the activity of the wild type human Factor VIIa is at least about 2.0. In a further embodiment the ratio between the activity of the Factor VII polypeptide and the activity of the wild type human Factor VIIa is at least about 4.0.

In a further embodiment of the invention, the factor VII polypeptide is a polypeptide, wherein the ratio between the activity of the Factor VII polypeptide and the activity of the wild type human Factor VIIa is at least about 1.25 when tested in a Factor VIIa activity assay. In one embodiment the ratio between the activity of the Factor VII polypeptide and the activity of the wild type human Factor VIIa is at least about 2.0 when tested in a Factor VIIa activity assay. In a further embodiment the ratio between the activity of the Factor VII polypeptide and the activity of the wild type human Factor VIIa is at least about 4.0 when tested in a Factor VIIa activity assay. The Factor VIIa activity may be measured by the assays described under "assays".

In a further embodiment of the invention, the factor VII polypeptide is a polypeptide, wherein the ratio between the activity of the Factor VII polypeptide and the activity of the wild type human Factor VIIa is at least about 1.25 when tested in the "In Vitro Hydrolysis Assay". In one embodiment the ratio between the activity of the Factor VII polypeptide and the activity of the wild type human Factor VIIa is at least about 2.0 when tested in the "In Vitro Hydrolysis Assay". In a further embodiment the ratio between the activity of the Factor VII polypeptide and the activity of the wild type human Factor VIIa is at least about 4.0 when tested in the "In Vitro Hydrolysis Assay".

In a further embodiment of the invention, the factor VII polypeptide is a polypeptide, wherein the ratio between the activity of the Factor VII polypeptide and the activity of the wild type human Factor VIIa is at least about 1.25 when tested in the "In Vitro Proteolysis Assay". In one embodiment the ratio between the activity of the Factor VII polypeptide and the activity of the wild type human Factor VIIa is at least about 2.0 when tested in the "In Vitro Proteolysis Assay". In a further embodiment the ratio between the activity of the Factor VII polypeptide and the activity of the wild type human Factor VIIa is at least about 4.0 when tested in the "In Vitro Proteolysis Assay". In a further embodiment the ratio between the activity of the Factor VII polypeptide and the activity of the wild type human Factor VIIa is at least about 8.0 when tested in the "In Vitro Proteolysis Assay".

The present invention is also suitable for Factor VII/VIIa variants with increased activity compared to wild type. Factor VII/VIIa variants with increased activity may be found by testing in suitable assays described in the following. These assays can be performed as a simple preliminary in vitro test. Thus, the section "assays" discloses a simple test (entitled "In Vitro Hydrolysis Assay") for the activity of Factor VIIa variants of the invention. Based thereon, Factor VIIa variants which are of particular interest are such variants where the ratio between the activity of the variant and the activity of wild type Factor VII is above 1.0, e.g. at least about 1.25, preferably at least about 2.0, such as at least about 3.0 or, even more preferred, at least about 4.0 when tested in the "In Vitro Hydrolysis Assay".

The activity of the variants can also be measured using a physiological substrate such as factor X ("In Vitro Proteolysis Assay") (see under "assays"), suitably at a concentration of 100-1000 nM, where the factor Xa generated is measured after the addition of a suitable chromogenic substrate (e.g. S-2765). In addition, the activity assay may be run at physiological temperature.

The ability of the Factor VIIa variants to generate thrombin can also be measured in an assay comprising all relevant coagulation factors and inhibitors at physiological concentrations (minus factor VIII when mimicking hemophilia A conditions) and activated platelets (as described on p. 543 in Monroe et al. (1997) Brit. J. Haematol. 99, 542-547 which is hereby incorporated as reference).

The term "identity" as known in the art, refers to a relationship between the sequences of two or more polypeptide molecules or two or more nucleic acid molecules, as determined by comparing the sequences. In the art, "identity" also means the degree of sequence relatedness between nucleic acid molecules or between polypeptides, as the case may be, as determined by the number of matches between strings of two or more nucleotide residues or two or more amino acid residues. "Identity" measures the percent of identical matches between the smaller of two or more sequences with gap alignments (if any) addressed by a particular mathematical model or computer program (i.e., "algorithms").

The term "similarity" is a related concept, but in contrast to "identity", refers to a sequence relationship that includes both identical matches and conservative substitution matches. If two polypeptide sequences have, for example, {fraction ($10/20$)} identical amino acids, and the remainder are all non-conservative substitutions, then the percent identity and similarity would both be 50%. If, in the same example, there are 5 more positions where there are conservative substitutions, then the percent identity remains 50%, but the percent similarity would be 75% ({fraction ($15/20$)}). Therefore, in cases where there are conservative substitutions, the degree of similarity between two polypeptides will be higher than the percent identity between those two polypeptides.

The term "isolated polypeptide" refers to a polypeptide of the present invention that (1) has been separated from at least about 50 percent of polynucleotides, lipids, carbohydrates or other materials (i.e., contaminants) with which it is naturally associated, (2) is not covalently linked to all or a portion of a polypeptide to which the "isolated polypeptide" is linked in nature, (3) is operably linked covalently to a polypeptide to which it is not covalently linked in nature, or (4) does not occur in nature. Preferably, the isolated polypeptide is substantially free from any other contaminating polypeptides or other contaminants that are found in its natural environment which would interfere with its therapeutic, diagnostic, prophylactic or research use.

Conservative modifications to the amino acid sequence of SEQ ID NO:1 (and the corresponding modifications to the encoding nucleotides) outside the positions for substitutions claimed will produce FVII polypeptides having functional and chemical characteristics similar to those of naturally occurring FVII polypeptide. In contrast, substantial modifications in the functional and/or chemical characteristics of FVII polypeptides may be accomplished by selecting substitutions in the amino acid sequence of SEQ ID NO:1 that differ significantly in their effect on maintaining (a) the structure of the molecular backbone in the area of the substitution, for example, as a sheet or helical conformation, (b) the charge or hydrophobicity of the molecule at the target site, or (c) the bulk of the side chain.

For example, a "conservative amino acid substitution" may involve a substitution of a native amino acid residue with a non-native residue such that there is little or no effect on the polarity or charge of the amino acid residue at that position. Furthermore, any native residue in the polypeptide may also be substituted with almandine, as has been previously described for "alanine scanning mutagenesis" (see, for example, MacLennan et al., 1998, Acta Physiol. Scand. Suppl. 643:55-67; Sasaki et al., 1998, Adv. Biophys. 35:1-24, which discuss alanine scanning mutagenesis).

Identity and similarity of related polypeptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math., 48:1073 (1988).

Preferred methods to determine identity and/or similarity are designed to give the largest match between the sequences tested. Methods to determine identity and similarity are described in publicly available computer programs. Preferred computer program methods to determine identity and similarity between two sequences include, but are not limited to, the GCG program package, including GAP (Devereux et al., Nucl. Acid. Res., 12:387 (1984); Genetics Computer Group, University of Wisconsin, Madison, Wis.), BLASTP, BLASTN, and FASTA (Altschul et al., J. Mol. Biol., 215:403-410 (1990)). The BLASTX program is publicly available from the National Center for Biotechnology Information (NCBI) and other sources (BLAST Manual, Altschul et al. NCB/NLM/NIH Bethesda, Md. 20894; Altschul et al., supra). The well known Smith Waterman algorithm may also be used to determine identity.

Certain alignment schemes for aligning two amino acid sequences may result in the matching of only a short region of the two sequences, and this small aligned region may have very high sequence identity even though there is no significant relationship between the two full length sequences. Accordingly, in a preferred embodiment, the selected alignment method (GAP program) will result in an alignment that spans at least 50 contiguous amino acids of the target polypeptide.

For example, using the computer algorithm GAP (Genetics Computer Group, University of Wisconsin, Madison, Wis.), two polypeptides for which the percent sequence identity is to be determined are aligned for optimal matching of their respective amino acids (the "matched span", as determined by the algorithm). A gap opening penalty (which is calculated as 3.times. the average diagonal; the "average diagonal" is the average of the diagonal of the comparison matrix being used; the "diagonal" is the score or number assigned to each perfect amino acid match by the particular comparison matrix) and a gap extension penalty (which is usually {fraction (1/10)} times the gap opening penalty), as well as a comparison matrix such as PAM 250 or BLOSUM 62 are used in conjunction with the algorithm. A standard comparison matrix (see Dayhoff et al., Atlas of Protein Sequence and Structure, vol. 5, supp. 3 (1978) for the PAM 250 comparison matrix; Henikoff et al., Proc. Natl. Acad. Sci. USA, 89:10915-10919 (1992) for the BLOSUM 62 comparison matrix) is also used by the algorithm.

Preferred parameters for a polypeptide sequence comparison include the following:

Algorithm: Needleman et al., J. Mol. Biol, 48:443-453 (1970); Comparison matrix: BLOSUM 62 from Henikoff et al., Proc. Natl. Acad. Sci. USA, 89:10915-10919 (1992); Gap Penalty: 12, Gap Length Penalty: 4, Threshold of Similarity: 0.

The GAP program is useful with the above parameters. The aforementioned parameters are the default parameters for polypeptide comparisons (along with no penalty for end gaps) using the GAP algorithm.

Preferred parameters for nucleic acid molecule sequence comparisons include the following: Algorithm: Needleman et al., J. Mol. Biol., 48:443-453 (1970); Comparison matrix: matches=+10, mismatch=0, Gap Penalty: 50, Gap Length Penalty: 3.

The GAP program is also useful with the above parameters. The aforementioned parameters are the default parameters for nucleic acid molecule comparisons.

Other exemplary algorithms, gap opening penalties, gap extension penalties, comparison matrices, thresholds of similarity, etc. may be used, including those set forth in the Program Manual, Wisconsin Package, Version 9, September, 1997. The particular choices to be made will be apparent to those of skill in the art and will depend on the specific comparison to be made, such as DNA to DNA, protein to protein, protein to DNA; and additionally, whether the comparison is between given pairs of sequences (in which case GAP or BestFit are generally preferred) or between one sequence and a large database of sequences (in which case FASTA or BLASTA are preferred).

The term "Tissue Factor binding affinity", as used herein, means the strength of the binding of a FVII polypeptide to human Tissue Factor. The affinity of a FVII polypeptide is measured by the dissociation constant $K_d$, defined as [FVII]×[TF]/[FVII–TF] where [FVII–TF] is the molar concentration of the FVII/TF complex, [FVII] is the molar concentration of the unbound FVII polypeptide and [TF] is the molar concentration of the unbound human Tissue Factor. The affinity constant $K_a$ is defined by $1/K_d$.

The phrase "substantially the same activity or increased activity compared to recombinant wild type human Factor VIIa", as used herein, means an activity more than 50% of the activity of recombinant wild type human Factor VIIa. In one embodiment the activity is more than 60% of the activity of recombinant wild type human Factor VIIa. In one embodiment the activity is more than 70% of the activity of recombinant wild type human Factor VIIa. In one embodiment the activity is more than 80% of the activity of recombinant wild type human Factor VIIa. In another embodiment the activity is more than 90% of the activity of recombinant wild type human Factor VIIa. In a further embodiment the activity is more than 100% of the activity of recombinant wild type human Factor VIIa. In a further embodiment the activity is more than 120% of the activity of recombinant wild type human Factor VIIa. In a further embodiment the activity is more than 200% of the activity of recombinant wild type human Factor VIIa. In a further embodiment the activity is more than 400% of the activity of recombinant wild type human Factor Vila.

The term "activity" as used herein means the ability of a Factor VII polypeptide to convert its substrate Factor X to the active Factor Xa. The activity of a Factor VII polypeptide may be measured with the "In Vitro Proteolysis Assay".

The phrase "a Tissue Factor binding affinity lower than recombinant wild type human Factor VIIa", as used herein, means an binding affinity lower than that of recombinant wild type human Factor VIIa as measured in a TF binding affinity assay, such as the Biosensor assay as described in Example 5. In one embodiment the Tissue Factor binding affinity is less than 90% of the Tissue Factor binding affinity of recombinant wild type human Factor VIIa. In one embodiment the Tissue Factor binding affinity is less than 80% of the Tissue Factor binding affinity of recombinant wild type human Factor VIIa. In one embodiment the Tissue Factor binding affinity is less than 70% of the Tissue Factor binding affinity of recombinant wild type human Factor VIIa. In one embodiment the Tissue Factor binding affinity is less than 60% of the Tissue Factor binding affinity of recombinant wild type human Factor VIIa. In one embodiment the Tissue Factor binding affinity is less than 50% of the Tissue Factor binding affinity of recombinant wild type human Factor VIIa. In one embodiment the Tissue Factor binding affinity is less than 40% of the Tissue Factor binding affinity of recombinant wild type human Factor VIIa. In one embodiment the Tissue Factor binding affinity is less than 30% of the Tissue Factor binding affinity of recombinant wild type human Factor VIIa. In one embodiment the Tissue Factor binding affinity is less than 20% of the Tissue Factor binding affinity of recombinant wild type human Factor VIIa. In one embodiment the Tissue Factor binding affinity is less than 10% of the Tissue Factor binding affinity of recombinant wild type human Factor VIIa. In one embodiment the Tissue Factor binding affinity is less than 5% of the Tissue Factor binding affinity of recombinant wild type human Factor VIIa. In one embodiment the Tissue Factor binding affinity is less than 1% of the Tissue Factor binding affinity of recombinant wild type human Factor VIIa. In one embodiment the Tissue Factor binding affinity is less than 0.1% of the Tissue Factor binding affinity of recombinant wild type human Factor VIIa. In one embodiment the Tissue Factor binding affinity is less than 0.01% of the Tissue Factor binding affinity of recombinant wild type human Factor VIIa. In one embodiment the Tissue Factor binding affinity is less than 0.001% of the Tissue Factor binding affinity of recombinant wild type human Factor VIIa.

The term "polyethylene glycol" or "PEG" means a polyethylene glycol compound or a derivative thereof, with or without coupling agents, coupling or activating moieties (e.g., with thiol, triflate, tresylate, azirdine, oxirane, or preferably with a maleimide moiety). Compounds such as maleimido monomethoxy PEG are exemplary of activated PEG compounds of the invention.

In one embodiment of the invention, the Factor VII polypeptides are Factor VII polypeptides, wherein one or more amino acid corresponding to amino acids at positions selected from K18, R36, S43, K62, Q64, L65, I69, F71, L73, P74, E77, G78, R79, K85, Q88, N93, F275, R277, M306, T307, Q308, D309, or R379 of SEQ ID NO: 1 have been substituted with a different amino acid, which different amino acid decreases the Tissue Factor binding affinity.

The term "a different amino acid" as used herein means one or more amino acids that are different from that amino acid naturally present at that position. This includes but is not limited to amino acids that can be encoded by a polynucleotide. Preferably the different amino acid is in natural L-form and can be encoded by a polynucleotide. A specific example being L-Glutamic acid (L-Glu).

In a further embodiment, the Factor VII polypeptides of the invention are Factor VII polypeptides, wherein the amino acid corresponding to the amino acid at a position K18 of SEQ ID NO: 1 has been substituted with a different amino acid. In one embodiment this different amino acid at a position K18 of SEQ ID NO: 1 is selected from the list consisting of E, D, A, and F.

In a further embodiment, the Factor VII polypeptides of the invention are Factor VII polypeptides, wherein the amino acid corresponding to the amino acid at a position R36 of SEQ ID NO: 1 has been substituted with a different amino acid. In one embodiment this different amino acid at a position R36 of SEQ ID NO: 1 is selected from the list consisting of E, D, A, and F.

In a further embodiment, the Factor VII polypeptides of the invention are Factor VII polypeptides, wherein the amino acid corresponding to the amino acid at a position S43 of SEQ ID NO: 1 has been substituted with a different amino acid. In one embodiment this different amino acid at a position S43 of SEQ ID NO: 1 is selected from the list consisting of E, D, K, R, A, F, and N. In one embodiment this different amino acid is selected from the list consisting of E, D, K, R, A, and F. In one embodiment this different amino acid is an N.

In a further embodiment, the Factor VII polypeptides of the invention are Factor VII polypeptides, wherein the amino acid corresponding to the amino acid at a position K62 of SEQ ID NO: 1 has been substituted with a different amino acid. In one embodiment this different amino acid at a position K62 of SEQ ID NO: 1 is selected from the list consisting of E, D, A, and F. In one embodiment this different amino acid is selected from the list consisting of D, A, and F.

In a further embodiment, the Factor VII polypeptides of the invention are Factor VII polypeptides, wherein the amino acid corresponding to the amino acid at a position Q64 of SEQ ID NO: 1 has been substituted with a different amino acid. In one embodiment this different amino acid at a position Q64 of SEQ ID NO: 1 is selected from the list consisting of E, D, K, R, A, and F.

In a further embodiment, the Factor VII polypeptides of the invention are Factor VII polypeptides, wherein the amino acid corresponding to the amino acid at a position L65 of SEQ ID NO: 1 has been substituted with a different amino acid. In one embodiment this different amino acid at a position L65 of SEQ ID NO: 1 is selected from the list consisting of E, D, K, R, A, and F.

In a further embodiment, the Factor VII polypeptides of the invention are Factor VII polypeptides, wherein the amino acid corresponding to the amino acid at a position I69 of SEQ ID NO: 1 has been substituted with a different amino acid. In one embodiment this different amino acid at a position I69 of SEQ ID NO: 1 is selected from the list consisting of E, D, K, R, A, and F. In one embodiment this different amino acid is selected from the list consisting of E, D, K, R, and F.

In a further embodiment, the Factor VII polypeptides of the invention are Factor VII polypeptides, wherein the amino acid corresponding to the amino acid at a position F71 of SEQ ID NO: 1 has been substituted with a different amino acid. In one embodiment this different amino acid at a position F71 of SEQ ID NO: 1 is selected from the list consisting of E, D, K, R, and A. In one embodiment this different amino acid is selected from the list consisting of K, R, and A.

In a further embodiment, the Factor VII polypeptides of the invention are Factor VII polypeptides, wherein the amino acid corresponding to the amino acid at a position L73 of SEQ ID NO: 1 has been substituted with a different amino acid. In one embodiment this different amino acid at a position L73 of SEQ ID NO: 1 is selected from the list consisting of E, D, K, R, A, and F.

In a further embodiment, the Factor VII polypeptides of the invention are Factor VII polypeptides, wherein the amino acid corresponding to the amino acid at a position P74 of SEQ ID NO: 1 has been substituted with a different amino acid. In one embodiment this different amino acid at a position P74 of SEQ ID NO: 1 is selected from the list consisting of E, D, K, R, A, and F.

In a further embodiment, the Factor VII polypeptides of the invention are Factor VII polypeptides, wherein the amino acid corresponding to the amino acid at a position E77 of SEQ ID NO: 1 has been substituted with a different amino acid. In one embodiment this different amino acid at a position E77 of SEQ ID NO: 1 is selected from the list consisting of K, R, and A.

In a further embodiment, the Factor VII polypeptides of the invention are Factor VII polypeptides, wherein the amino acid corresponding to the amino acid at a position G78 of SEQ ID NO: 1 has been substituted with a different amino acid. In one embodiment this different amino acid at a position G78 of SEQ ID NO: 1 is selected from the list consisting of E, D, K, R, A, and F.

In a further embodiment, the Factor VII polypeptides of the invention are Factor VII polypeptides, wherein the amino acid corresponding to the amino acid at a position R79 of SEQ ID NO: 1 has been substituted with a different amino acid. In one embodiment this different amino acid at a position R79 of SEQ ID NO: 1 is selected from the list consisting of E, D, and A.

In a further embodiment, the Factor VII polypeptides of the invention are Factor VII polypeptides, wherein the amino acid corresponding to the amino acid at a position K85 of SEQ ID NO: 1 has been substituted with a different amino acid. In one embodiment this different amino acid at a position K85 of SEQ ID NO: 1 is selected from the list consisting of E, D, and A.

In a further embodiment, the Factor VII polypeptides of the invention are Factor VII polypeptides, wherein the amino acid corresponding to the amino acid at a position Q88 of SEQ ID NO: 1 has been substituted with a different amino acid. In one embodiment this different amino acid at a position Q88 of SEQ ID NO: 1 is selected from the list consisting of E, D, K, R, A, and F.

In a further embodiment, the Factor VII polypeptides of the invention are Factor VII polypeptides, wherein the amino acid corresponding to the amino acid at a position N93 of SEQ ID NO: 1 has been substituted with a different amino acid. In one embodiment this different amino acid at a position N93 of SEQ ID NO: 1 is selected from the list consisting of E, D, K, R, A, and F.

In a further embodiment, the Factor VII polypeptides of the invention are Factor VII polypeptides, wherein the amino acid corresponding to the amino acid at a position F275 of SEQ ID NO: 1 has been substituted with a different amino acid. In one embodiment this different amino acid at a position F275 of SEQ ID NO: 1 is selected from the list consisting of E, D, K, R, and A.

In a further embodiment, the Factor VII polypeptides of the invention are Factor VII polypeptides, wherein the amino acid corresponding to the amino acid at a position R277 of SEQ ID NO: 1 has been substituted with a different amino acid. In one embodiment this different amino acid at a position R277 of SEQ ID NO: 1 is selected from the list consisting of E, D, A, and F.

In a further embodiment, the Factor VII polypeptides of the invention are Factor VII polypeptides, wherein the amino acid corresponding to the amino acid at a position T307 of SEQ ID NO: 1 has been substituted with a different amino acid. In one embodiment this different amino acid at a position T307 of SEQ ID NO: 1 is selected from the list consisting of E, D, K, R, A, F, and N.

In a further embodiment, the Factor VII polypeptides of the invention are Factor VII polypeptides, wherein the amino acid corresponding to the amino acid at a position Q308 of SEQ ID NO: 1 has been substituted with a different amino acid. In one embodiment this different amino acid at a position Q308 of SEQ ID NO: 1 is selected from the list consisting of E, D, K, R, A, F, and N.

In a further embodiment, the Factor VII polypeptides of the invention are Factor VII polypeptides, wherein the amino acid corresponding to the amino acid at a position R379 of SEQ ID NO: 1 has been substituted with a different amino acid. In one embodiment this different amino acid at a position R379 of SEQ ID NO: 1 is selected from the list consisting of E, D, A, and F.

In a further embodiment, the Factor VII polypeptides of the invention are Factor VII polypeptides, wherein the amino acid corresponding to the amino acid at a position M306 of SEQ ID NO: 1 has been substituted with a different amino acid. In one embodiment this different amino acid at a position M306 of SEQ ID NO: 1 is selected from the list consisting of E, D, K, R, A, and F. In one embodiment this different amino acid is selected from the list consisting of E, K, R, A, and F.

In a further embodiment, the Factor VII polypeptides of the invention are Factor VII polypeptides, wherein the amino acid corresponding to the amino acid at a position D309 of SEQ ID NO: 1 has been substituted with a different amino acid. In one embodiment this different amino acid at a position D309 of SEQ ID NO: 1 is selected from the list consisting of K, R, and A.

In a further embodiment, the Factor VII polypeptide of the invention is a Factor VII polypeptide selected from the list consisting of S43N-FVII, K62E-FVII, Q64E-FVII, I69F-FVII, K62E/I69A-FVII, Q64E/I69A-FVII, K62E/Q64E/I69A-FVII, K62E/I69F-FVII, Q64E/I69F-FVII, and K62E/Q64E/I69F-FVII.

In a further embodiment, the Factor VII polypeptides of the invention are Factor VII polypeptides further comprising amino acid substitutions selected from the list consisting of L305V, L305V/M306D/D309S, L305I, L305T, F374P, V158T/M298Q, V158D/E296V/M298Q, K337A, M298Q, V158D/M298Q, L305V/K337A, V158D/E296V/M298Q/L305V, V158D/E296V/M298Q/K337A, V158D/E296V/M298Q/L305V/K337A, K157A, E296V, E296V/M298Q, V158D/E296V, V158D/M298K, and S336G, L305V/K337A, L305V/V158D, L305V/E296V, L305V/M298Q, L305V/V158T, L305V/K337A/V158T, L305V/K337A/M298Q, L305V/K337A/E296V, L305V/K337A/V158D, L305V/V158D/M298Q, L305V/V158D/E296V, L305V/V158T/M298Q, L305V/V158T/E296V, L305V/E296V/M298Q, L305V/V158T/E296V/M298Q, L305V/V158T/K337A/M298Q, L305V/V158T/E296V/K337A, L305V/V158D/K337A/M298Q, L305V/V158D/E296V/K337A, L305V/V158D/E296V/M298Q/K337A, L305V/V158T/E296V/M298Q/K337A, S314E/K316H, S314E/K316Q, S314E/L305V, S314E/K337A, S314E/V158D, S314E/E296V, S314E/M298Q, S314E/V158T, K316H/L305V, K316H/K337A, K316H/V158D, K316H/E296V, K316H/M298Q, K316H/V158T, K316Q/L305V, K316Q/K337A, K316Q/V158D, K316Q/E296V, K316Q/M298Q, K316Q/V158T, S314E/L305V/K337A, S314E/L305V/V158D, S314E/L305V/E296V, S314E/L305V/M 298Q, S314E/L305V/V158T, S314E/L305V/K337A/V158T, S314E/L305V/K337A/M 298Q, S314E/L305V/K337A/E296V, S314E/L305V/K337A/V158D, S314E/L305V/V158D/M298Q, S314E/L305V/V158D/E296V, S314E/L305V/V158T/M298Q, S314E/L305V/V158T/E296V, S314E/L305V/E296V/M298Q, S314E/L305V/V158D/E296V/M298Q, S314E/L305V/V158T/E296V/M298Q, S314E/L305V/V158T/K337A/M298Q, S314E/L305V/V158T/E296V/K337A, S314E/L305V/V158D/K337A/M298Q, S314E/L305V/V158D/E296V/K337A, S314E/L305V/V158D/E296V/M298Q/K337A, S314E/L305V/V158T/E296V/M298Q/K337A, K316H/L305V/K337A, K316H/L305V/V158D, K316H/L305V/E296V, K316H/L305V/M 298Q, K316H/L305V/V158T, K316H/L305V/K337A/V158T, K316H/L305V/K337A/M298Q, K316H/L305V/K337A/E296V, K316H/L305V/K337A/V158D, K316H/L305V/V158D/M298Q, K316H/L305V/V158D/E296V, K316H/L305V/V158T/M298Q, K316H/L305V/V158T/E296V, K316H/L305V/E296V/M298Q, K316H/L305V/V158D/E296V/M298Q, K316H/L305V/V158T/E296V/M298Q, K316H/L305V/V158T/K337A/M298Q, K316H/L305V/V158T/E296V/K337A, K316H/L305V/V158D/K337A/M 298Q, K316H/L305V/V158D/E296V/K337A, K316H/L305V/V158D/E296V/M298Q/K337A, K316H/L305V/V158T/E296V/M298Q/K337A, K316Q/L305V/K337A, K316Q/L305V/V158D, K316Q/L305V/E296V, K316Q/L305V/M298Q, K316Q/L305V/V158T, K316Q/L305V/K337A/V158T, K316Q/L305V/K337A/M 298Q, K316Q/L305V/K337A/E296V, K316Q/L305V/K337A/V158D, K316Q/L305V/V158D/M298Q, K316Q/L305V/V158D/E296V, K316Q/L305V/V158T/M298Q, K316Q/L305V/V158T/E296V, K316Q/L305V/E296V/M298Q, K316Q/L305V/V158D/E296V/M298Q, K316Q/L305V/V158T/E296V/M298Q, K316Q/L305V/V158T/K337A/M 298Q, K316Q/L305V/V158T/E296V/K337A, K316Q/L305V/V158D/K337A/M298Q, K316Q/L305V/V158D/E296V/K337A, K316Q/L305V/V158D/E296V/M298Q/K337A, K316Q/L305V/V158T/E296V/M298Q/K337A, F374Y/K337A, F374Y/V158D, F374Y/E296V, F374Y/M298Q, F374Y/V158T, F374Y/S314E, F374Y/L305V, F374Y/L305V/K337A, F374Y/L305V/V158D, F374Y/L305V/E296V, F374Y/L305V/M298Q, F374Y/L305V/V158T, F374Y/L305V/S314E, F374Y/K337A/S314E, F374Y/K337A/V158T, F374Y/K337A/M298Q, F374Y/K337A/E296V, F374Y/K337A/V158D, F374Y/V158D/S314E, F374Y/V158D/M298Q, F374Y/V158D/E296V, F374Y/V158T/S314E, F374Y/V158T/M298Q, F374Y/V158T/E296V, F374Y/E296V/S314E, F374Y/S314E/M298Q, F374Y/E296V/M298Q, F374Y/L305V/K337A/V158D, F374Y/L305V/K337A/E296V, F374Y/L305V/K337A/M298Q, F374Y/L305V/K337A/V158T, F374Y/L305V/K337A/S314E, F374Y/L305V/V158D/E296V, F374Y/L305V/V158D/M298Q, F374Y/L305V/V158D/S314E, F374Y/L305V/E296V/M298Q, F374Y/L305V/E296V/V158T, F374Y/L305V/E296V/S314E, F374Y/L305V/M298Q/V158T, F374Y/L305V/M298Q/S314E, F374Y/L305V/V158T/S314E, F374Y/K337A/S314E/V158T, F374Y/K337A/S314E/M298Q, F374Y/K337A/S314E/E296V, F374Y/K337A/S314E/V158D, F374Y/K337A/V158T/M298Q, F374Y/K337A/V158T/E296V, F374Y/K337A/M298Q/E296V, F374Y/K337A/M298Q/V158D, F374Y/K337A/E296V/V158D, F374Y/V158D/S314E/M298Q, F374Y/V158D/S314E/E296V, F374Y/V158D/M298Q/E296V, F374Y/V158T/S314E/E296V, F374Y/V158T/S314E/M298Q, F374Y/V158T/M298Q/E296V, F374Y/E296V/S314E/M298Q, F374Y/L305V/M298Q/K337A/S314E, F374Y/L305V/E296V/K337A/S314E, F374Y/E296V/M298Q/K337A/S314E, F374Y/L305V/E296V/M298Q/K337A, F374Y/L305V/E296V/M298Q/S314E, F374Y/V158D/E296V/M298Q/K337A, F374Y/V158D/E296V/M298Q/S314E, F374Y/L305V/V158D/K337A/S314E, F374Y/V158D/M298Q/K337A/S314E, F374Y/V158D/E296V/K337A/S314E, F374Y/L305V/V158D/E296V/M298Q, F374Y/L305V/V158D/M298Q/K337A, F374Y/L305V/V158D/E296V/K337A, F374Y/L305V/V158D/M298Q/S314E, F374Y/L305V/V158D/E296V/S314E, F374Y/V158T/E296V/M298Q/K337A, F374Y/V158T/E296V/M298Q/S314E, F374Y/L305V/V158T/K337A/S314E, F374Y/V158T/M298Q/K337A/S314E, F374Y/V158T/E296V/K337A/S314E, F374Y/L305V/V158T/E296V/M298Q, F374Y/L305V/V158T/M298Q/K337A, F374Y/L305V/V158T/E296V/K337A, F374Y/L305V/V158T/M298Q/S314E, F374Y/L305V/V158T/E296V/S314E, F374Y/E296V/M298Q/K337A/V158T/S314E, F374Y/V158D/E296V/M298Q/K337A/S314E, F374Y/L305V/V158D/E296V/M298Q/S314E, F374Y/L305V/E296V/M298Q/V158T/S314E, F374Y/L305V/E296V/M298Q/K337A/V158T, F374Y/L305V/E296V/K337A/V158T/S314E, F374Y/L305V/M298Q/K337A/V158T/S314E, F374Y/L305V/V158D/E296V/M298Q/K337A, F374Y/L305V/V158D/E296V/K337A/S314E, F374Y/L305V/V158D/M298Q/K337A/S314E, F374Y/L305V/E296V/M298Q/K337A/S314E, F374Y/L305V/V158D/E296V/M298Q/K337A/S314E, S52A, S60A; R152E, S344A, P11Q/K33E, T106N, K143N/N145T, V253N, R290N/A292T, G291N, R315N/V317T, and K143N/N145T/R315N/V317T; or having substitutions, additions or deletions in the amino acid sequence from 233Thr to 240Asn, or having substitutions, additions or deletions in the amino acid sequence from 304Arg to 329Cys.

In a further embodiment, the Factor VII polypeptides of the invention are Factor VII polypeptides, wherein the dissociation constant $K_d$ of said Factor VII polypeptide is higher than 5 nM, such as higher than 7 nM, such as higher than 10 nM, such as higher than 20 nM, such as higher than 30 nM, such as higher than 50 nM, such as higher than 100 nM, such as higher than 200 nM, such as higher than 300 nM, such as higher than 400 nM, such as higher than 500 nM, such as higher than 1 µM.

In a further embodiment, the Factor VII polypeptides of the invention comprises one or more amino acid substitution selected from K18$X_1$, R36$X_2$, S43$X_3$, K62$X_4$, Q64$X_5$, L65$X_6$, I69$X_7$, F71$X_8$, L73$X_9$, P74$X_{10}$, E77$X_{11}$, G78$X_{12}$, R79$X_{13}$, K85$X_{14}$, Q88$X_{15}$, N93$X_{16}$, F275$X_{17}$, R277$X_{18}$, M306$X_{19}$, T307$X_{20}$, Q308$X_{21}$, D309$X_{22}$, or R379$X_{23}$ corresponding to amino acids at positions of SEQ ID NO: 1, which different amino acid decreases the Tissue Factor binding affinity, wherein $X_1$ is E, D, A, or F;
$X_2$ is E, D, K, A, F, or N;
$X_3$ is E, D, K, R, A, or F;
$X_4$ is D, A, or F;
$X_5$ is E, D, K, R, A, F, or N;
$X_6$ is E, D, K, R, A, or F;
$X_7$ is C, D, E, F, G, H, K, L, M, N, P, Q, R, S, T, V, W, or Y;
$X_8$ is A, G, H, I, K, L, M, P, R, S, T, V, or W;
$X_9$ is A, D, E, F, G, H, I, K, M, N, P, Q, R, S, T, V, W, or Y;
$X_{10}$ is A, D, E, F, G, H, I, K, L, M, N, Q, R, S, T, V, W, or Y;
$X_{11}$ is A, F, G, H, I, K, L, M, N, P, Q, R, S, T, V, W, or Y;
$X_{12}$ is A, D, E, F, H, I, K, L, M, N, P, Q, R, S, T, V, W, or Y;
$X_{13}$ is A, D, E, F, G, H, I, K, L, M, N, P, Q, S, T, V, W, or Y;
$X_{14}$ is A, D, E, F, G, I, L, M, P, S, T, V, W, or Y;
$X_{15}$ is A, D, E, F, G, H, I, K, L, M, N, P, R, S, T, V, W, or Y;
$X_{16}$ is A, D, E, F, G, H, I, K, L, M, P, Q, R, S, T, V, W, or Y;
$X_{17}$ is A, D, E, G, I, K, L, M, N, P, Q, R, S, T, V, W, or Y;
$X_{18}$ is A, D, E, F, G, H, I, K, L, M, P, Q, S, T, V, W, or Y;
$X_{19}$ is A, E, F, G, H, I, K, L, P, Q, R, S, T, V, W, or Y;
$X_{20}$ is A, D, E, F, G, H, I, K, L, M, N, P, Q, R, S, V, W, or Y;
$X_{21}$ is A, D, E, F, G, H, I, K, L, M, N, P, R, S, T, V, W, or Y;
$X_{22}$ is A, F, G, H, I, K, L, M, N, P, Q, R, V, W, or Y; and
$X_{23}$ is A, D, E, F, G, H, I, K, L, M, P, Q, S, T, V, W, or Y.

In a further embodiment, the Factor VII polypeptides of the invention is a Factor VII polypeptide, wherein one or more amino acid corresponding to amino acids at positions selected from K18, R36, K62, Q64, L65, I69, F71, L73, P74, E77, G78, R79, K85, Q88, N93, F275, R277, M306, Q308, D309, or R379 of SEQ ID NO: 1 have been substituted with a cysteine amino acid residue, which cysteine amino acid residue decreases the Tissue Factor binding affinity, and which cysteine amino acid residue is optionally conjugated with a chemical group, which chemical group increases the molecular weight of said Factor VII polypeptide. In one embodiment K18 of SEQ ID NO: 1 has been substituted with a cysteine amino acid residue. In one embodiment R36 of SEQ ID NO: 1 has been substituted with a cysteine amino acid residue. In one embodiment K62 of SEQ ID NO: 1 has been substituted with a cysteine amino acid residue. In one embodiment Q64 of SEQ ID NO: 1 has been substituted with a cysteine amino acid residue. In one embodiment L65 of SEQ ID NO: 1 has been substituted with a cysteine amino acid residue. In one embodiment I69 of SEQ ID NO: 1 has been substituted with a cysteine amino acid residue. In one embodiment F71 of SEQ ID NO: 1 has been substituted with a cysteine amino acid residue. In one embodiment L73 of SEQ ID NO: 1 has been substituted with a cysteine amino acid residue. In one embodiment P74 of SEQ ID NO: 1 has been substituted with a cysteine amino acid residue. In one embodiment E77 of SEQ ID NO: 1 has been substituted with a cysteine amino acid residue. In one embodiment G78 of SEQ ID NO: 1 has been substituted with a cysteine amino acid residue. In one embodiment R79 of SEQ ID NO: 1 has been substituted with a cysteine amino acid residue. In one embodiment K85 of SEQ ID NO: 1 has been substituted with a cysteine amino acid residue. In one embodiment Q88 of SEQ ID NO: 1 has been substituted with a cysteine amino acid residue. In one embodiment N93 of SEQ ID NO: 1 has been substituted with a cysteine amino acid residue. In one embodiment F275 of SEQ ID NO: 1 has been substituted with a cysteine amino acid residue. In one embodiment R277 of SEQ ID NO: 1 has been substituted with a cysteine amino acid residue. In one embodiment M306 of SEQ ID NO: 1 has been substituted with a cysteine amino acid residue. In one embodiment Q308 of SEQ ID NO: 1 has been substituted with a cysteine amino acid residue. In one embodiment D309 of SEQ ID NO: 1 has been substituted with a cysteine amino acid residue. In one embodiment R379 of SEQ ID NO: 1 has been substituted with a cysteine amino acid residue.

In a further embodiment, the Factor VII polypeptides of the invention is a Factor VII polypeptide comprising one or more N-glycosylation site N-Xaa-S/T introduced by amino acid substitutions corresponding to amino acids starting at positions selected from R36, Q64, I69, F71, P74, E77, G78, Q88, N93, F275, M306, T307, or D309 of SEQ ID NO: 1, wherein Xaa is any amino acid except P, which introduced N-glycosylation site decreases the Tissue Factor binding affinity. In one embodiment an N-glycosylation site N-Xaa-S/T is introduced at a position starting at R36 of SEQ ID NO: 1. In one embodiment an N-glycosylation site N-Xaa-S/T is introduced at a position starting at R36 of SEQ ID NO: 1. In one embodiment an N-glycosylation site N-Xaa-S/T is introduced at a position starting at Q64 of SEQ ID NO: 1.

In one embodiment an N-glycosylation site N-Xaa-S/T is introduced at a position starting at I69 of SEQ ID NO: 1. In one embodiment an N-glycosylation site N-Xaa-S/T is introduced at a position starting at F71 of SEQ ID NO: 1. In one embodiment an N-glycosylation site N-Xaa-S/T is introduced at a position starting at P74 of SEQ ID NO: 1. In one embodiment an N-glycosylation site N-Xaa-S/T is introduced at a position starting at E77 of SEQ ID NO: 1.

In one embodiment an N-glycosylation site N-Xaa-S/T is introduced at a position starting at G78 of SEQ ID NO: 1. In one embodiment an N-glycosylation site N-Xaa-S/T is introduced at a position starting at Q88 of SEQ ID NO: 1. In one embodiment an N-glycosylation site N-Xaa-S/T is introduced at a position starting at N93 of SEQ ID NO: 1. In one embodiment an N-glycosylation site N-Xaa-S/T is introduced at a position starting at F275 of SEQ ID NO: 1.

In one embodiment an N-glycosylation site N-Xaa-S/T is introduced at a position starting at M306 of SEQ ID NO: 1. In one embodiment an N-glycosylation site N-Xaa-S/T is introduced at a position starting at T307 of SEQ ID NO: 1. In one embodiment an N-glycosylation site N-Xaa-S/T is introduced at a position starting at D309 of SEQ ID NO: 1.

In a further embodiment, the Factor VII polypeptides of the invention is a Factor VII polypeptide, wherein the amino acid corresponding to the amino acid at a position K18 of SEQ ID NO: 1 has been substituted with an amino acid selected from the list consisting of E, D, A, and F.

In a further embodiment, the Factor VII polypeptides of the invention is a Factor VII polypeptide, wherein the amino acid corresponding to the amino acid at a position R36 of SEQ ID NO: 1 has been substituted with an amino acid selected from the list consisting of E, D, K, A, F, and N.

In a further embodiment, the Factor VII polypeptides of the invention is a Factor VII polypeptide, wherein the amino acid corresponding to the amino acid at a position S43 of SEQ ID NO: 1 has been substituted with an amino acid selected from the list consisting of E, D, K, R, A, and F.

In a further embodiment, the Factor VII polypeptides of the invention is a Factor VII polypeptide, wherein the amino acid corresponding to the amino acid at a position K62 of SEQ ID NO: 1 has been substituted with an amino acid selected from the list consisting of D, A, and F.

In a further embodiment, the Factor VII polypeptides of the invention is a Factor VII polypeptide, wherein the amino acid corresponding to the amino acid at a position Q64 of SEQ ID NO: 1 has been substituted with an amino acid selected from the list consisting of E, D, K, R, A, F, and N.

In a further embodiment, the Factor VII polypeptides of the invention is a Factor VII polypeptide, wherein the amino acid corresponding to the amino acid at a position L65 of SEQ ID NO: 1 has been substituted with an amino acid selected from the list consisting of E, D, K, R, A, and F.

In a further embodiment, the Factor VII polypeptides of the invention is a Factor VII polypeptide, wherein the amino acid corresponding to the amino acid at a position I69 of SEQ ID NO: 1 has been substituted with an amino acid selected from the list consisting of C, D, E, F, G, H, K, L, M, N, P, Q, R, S, T, V, W, and Y.

In a further embodiment, the Factor VII polypeptides of the invention is a Factor VII polypeptide, wherein the amino acid corresponding to the amino acid at a position F71 of SEQ ID NO: 1 has been substituted with an amino acid selected from the list consisting of A, G, H, I, K, L, M, P, R, S, T, V, and W.

In a further embodiment, the Factor VII polypeptides of the invention is a Factor VII polypeptide, wherein the amino acid corresponding to the amino acid at a position L73 of SEQ ID NO: 1 has been substituted with an amino acid selected from the list consisting of A, D, E, F, G, H, I, K, M, N, P, Q, R, S, T, V, W, and Y.

In a further embodiment, the Factor VII polypeptides of the invention is a Factor VII polypeptide, wherein the amino acid corresponding to the amino acid at a position P74 of SEQ ID NO: 1 has been substituted with an amino acid selected from the list consisting of A, D, E, F, G, H, I, K, L, M, N, Q, R, S, T, V, W, and Y.

In a further embodiment, the Factor VII polypeptides of the invention is a Factor VII polypeptide, wherein the amino acid corresponding to the amino acid at a position E77 of SEQ ID NO: 1 has been substituted with an amino acid selected from the list consisting of A, F, G, H, I, K, L, M, N, P, Q, R, S, T, V, W, and Y.

In a further embodiment, the Factor VII polypeptides of the invention is a Factor VII polypeptide, wherein the amino acid corresponding to the amino acid at a position G78 of SEQ ID NO: 1 has been substituted with an amino acid selected from the list consisting of A, D, E, F, H, I, K, L, M, N, P, Q, R, S, T, V, W, and Y.

In a further embodiment, the Factor VII polypeptides of the invention is a Factor VII polypeptide, wherein the amino acid corresponding to the amino acid at a position R79 of SEQ ID NO: 1 has been substituted with an amino acid selected from the list consisting of A, D, E, F, G, H, I, K, L, M, N, P, Q, S, T, V, W, and Y.

In a further embodiment, the Factor VII polypeptides of the invention is a Factor VII polypeptide, wherein the amino acid corresponding to the amino acid at a position K85 of SEQ ID NO: 1 has been substituted with an amino acid selected from the list consisting of A, D, E, F, G, I, L, M, P, S, T, V, W, and Y.

In a further embodiment, the Factor VII polypeptides of the invention is a Factor VII polypeptide, wherein the amino acid corresponding to the amino acid at a position Q88 of SEQ ID NO: 1 has been substituted with an amino acid selected from the list consisting of A, D, E, F, G, H, I, K, L, M, N, P, R, S, T, V, W, and Y.

In a further embodiment, the Factor VII polypeptides of the invention is a Factor VII polypeptide, wherein the amino acid corresponding to the amino acid at a position N93 of SEQ ID NO: 1 has been substituted with an amino acid selected from the list consisting of A, D, E, F, G, H, I, K, L, M, P, Q, R, S, T, V, W, and Y.

In a further embodiment, the Factor VII polypeptides of the invention is a Factor VII polypeptide, wherein the amino acid corresponding to the amino acid at a position F275 of SEQ ID NO: 1 has been substituted with an amino acid selected from the list consisting of A, D, E, G, I, K, L, M, N, P, Q, R, S, T, V, W, and Y.

In a further embodiment, the Factor VII polypeptides of the invention is a Factor VII polypeptide, wherein the amino acid corresponding to the amino acid at a position R277 of SEQ ID NO: 1 has been substituted with an amino acid selected from the list consisting of A, D, E, F, G, H, I, K, L, M, P, Q, S, T, V, W, and Y.

In a further embodiment, the Factor VII polypeptides of the invention is a Factor VII polypeptide, wherein the amino acid corresponding to the amino acid at a position M306 of SEQ ID NO: 1 has been substituted with an amino acid selected from the list consisting of A, E, F, G, H, I, K, L, P, Q, R, S, T, V, W, and Y.

In a further embodiment, the Factor VII polypeptides of the invention is a Factor VII polypeptide, wherein the amino acid corresponding to the amino acid at a position T307 of SEQ ID NO: 1 has been substituted with an amino acid selected from the list consisting of A, D, E, F, G, H, I, K, L, M, N, P, Q, R, S, V, W, and Y.

In a further embodiment, the Factor VII polypeptides of the invention is a Factor VII polypeptide, wherein the amino acid corresponding to the amino acid at a position Q308 of SEQ ID NO: 1 has been substituted with an amino acid selected from the list consisting of A, D, E, F, G, H, I, K, L, M, N, P, R, S, T, V, W, and Y.

In a further embodiment, the Factor VII polypeptides of the invention is a Factor VII polypeptide, wherein the amino acid corresponding to the amino acid at a position D309 of SEQ ID NO: 1 has been substituted with an amino acid selected from the list consisting of A, F, G, H, I, K, L, M, N, P, Q, R, V, W, and Y.

In a further embodiment, the Factor VII polypeptides of the invention is a Factor VII polypeptide, wherein the amino acid corresponding to the amino acid at a position R379 of SEQ ID NO: 1 has been substituted with an amino acid selected from the list consisting of A, D, E, F, G, H, I, K, L, M, P, Q, S, T, V, W, or Y.

In a further embodiment, the Factor VII polypeptides of the invention is a Factor VII polypeptide, which is selected from the list consisting of FVII-(S43N), FVII-(K62E), FVII-(Q64E), FVII-(I69F), FVII-(K62E/I69A), FVII-(Q64E/I69A), FVII-(Q62E/Q64E/I69A), FVII-(K62E/I69F), FVII-(Q64E/I69F), FVII-(K62E/Q64E/I69F), FVII-(S43C), FVII-(I69C), FVII-(Q64C), FVII-(M306C), FVII-(R277C), FVII-(I69N/F71T), FVII-(F71N/L73T), FVII-(R277N), and FVII-(D309N/L311T).

In one embodiment the polynucleotide construct of the invention is a vector.

The term "a polynucleotide" denotes a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. The length of a polynucleotide molecule is given herein in terms of nucleotides (abbreviated "nt") or base pairs (abbreviated "bp"). The term "nucleotides" is used for both single- and double-stranded molecules where the context permits. When the term is applied to double-stranded molecules it is used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired. Such unpaired ends will in general not exceed 20 nt in length.

The term "vector", as used herein, means any nucleic acid entity capable of the amplification in a host cell. Thus, the vector may be an autonomously replicating vector, i.e. a vector, which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated. The choice of vector will often depend on the host cell into which it is to be introduced. Vectors include, but are not limited to plasmid vectors, phage vectors, viruses or cosmid vectors. Vectors usually contain a replication origin and at least one selectable gene, i.e., a gene which encodes a product which is readily detectable or the presence of which is essential for cell growth.

In one embodiment, the eukaryotic host cell of the invention is of mammalian origin.

In a further embodiment, the eukaryotic host cell of the invention is selected from the group consisting of CHO cells, BHK cells or HEK cells.

The term "a eukaryotic host cell", as used herein, represent any cell, including hybrid cells, in which heterologous DNA can be expressed. Typical host cells includes, but are not limited to insect cells, yeast cells, mammalian cells, including human cells, such as BHK, CHO, HEK, and COS cells. In practicing the present invention, the host cells being cultivated are preferably mammalian cells, more preferably an established mammalian cell line, including, without limitation, CHO (e.g., ATCC CCL 61), COS-1 (e.g., ATCC CRL 1650), baby hamster kidney (BHK) and HEK293 (e.g., ATCC CRL 1573; Graham et al., *J. Gen. Virol.* 36:59-72, 1977) cell lines.

A preferred BHK cell line is the tk⁻ ts13 BHK cell line (Waechter and Baserga, *Proc. Natl. Acad. Sci. USA* 79:1106-1110, 1982), hereinafter referred to as BHK 570 cells. The BHK 570 cell line is available from the American Type Culture Collection, P.O. Box 1549, Manassas, Va. 20108, under ATCC accession number CRL 10314. A tk⁻ ts13 BHK cell line is also available from the ATCC under accession number CRL 1632.

Other suitable cell lines include, without limitation, Rat Hep I (Rat hepatoma; ATCC CRL 1600), Rat Hep II (Rat hepatoma; ATCC CRL 1548), TCMK (ATCC CCL 139), Human lung (ATCC HB 8065), NCTC 1469 (ATCC CCL 9.1) and DUKX cells (Urlaub and Chasin, *Proc. Natl. Acad. Sci. USA* 77:4216-4220, 1980). Also useful are 3T3 cells, Namalwa cells, myelomas and fusions of myelomas with other cells. In one embodiment the eucaryotic host cell is of mammalian origin. In a further embodiment the eucaryotic host cell is selected from the group consisting of CHO cells, BHK cells or HEK cells.

The term "treatment", as used herein, means the administration of an effective amount of a therapeutically active compound of the invention with the purpose of preventing any symptoms or disease state to develop or with the purpose of curing or easing such symptoms or disease states already developed. The term "treatment" is thus meant to include prophylactic treatment.

The term "enhancement of the normal haemostatic system" means an enhancement of the ability to generate thrombin.

As used herein the term "bleeding disorders" reflects any defect, congenital, acquired or induced, of cellular or molecular origin that is manifested in bleedings. Examples are clotting factor deficiencies (e.g. haemophilia A and B or deficiency of coagulation Factors XI or VII), clotting factor inhibitors, defective platelet function, thrombocytopenia or von Willebrand's disease.

The term "bleeding episodes" is meant to include uncontrolled and excessive bleeding which is a major problem both in connection with surgery and other forms of tissue damage. Uncontrolled and excessive bleeding may occur in subjects having a normal coagulation system and subjects having coagulation or bleeding disorders. Clotting factor deficiencies (haemophilia A and B, deficiency of coagulation factors XI or VII) or clotting factor inhibitors may be the cause of bleeding disorders. Excessive bleedings also occur in subjects with a normally functioning blood clotting cascade (no clotting factor deficiencies or -inhibitors against any of the coagulation factors) and may be caused by a defective platelet function, thrombocytopenia or von Willebrand's disease. In such cases, the bleedings may be similar to those bleedings caused by haemophilia because the haemostatic system, as in haemophilia, lacks or has abnormal essential clotting "compounds" (such as platelets or von Willebrand factor protein) that causes major bleedings. In subjects who experience extensive tissue damage in association with surgery or vast trauma, the normal haemostatic mechanism may be overwhelmed by the demand of immediate haemostasis and they may develop bleeding in spite of a normal haemostatic mechanism. Achieving satisfactory haemostasis also is a problem when bleedings occur in organs such as the brain, inner ear region and eyes with limited possibility for surgical haemostasis. The same problem may arise in the process of taking biopsies from various organs (liver, lung, tumour tissue, gastrointestinal tract) as well as in laparoscopic surgery. Common for all these situations is the difficulty to provide haemostasis by surgical techniques (sutures, clips, etc.) which also is the case when bleeding is diffuse (haemorrhagic gastritis and profuse uterine bleeding). Acute and profuse bleedings may also occur in subjects on anticoagulant therapy in whom a defective haemostasis has been induced by the therapy given. Such subjects may need surgical interventions in case the anticoagulant effect has to be counteracted rapidly. Radical retropubic prostatectomy is a commonly performed procedure for subjects with localized prostate cancer. The operation is frequently complicated by significant and sometimes massive blood loss. The considerable blood loss during prostatectomy is mainly related to the complicated anatomical situation, with various densely vascularized sites that are not easily accessible for surgical haemostasis, and which may result in diffuse bleeding from a large area. Another situation that may cause problems in the case of unsatisfactory haemostasis is when subjects with a normal haemostatic mechanism are given anticoagulant therapy to prevent thromboembolic disease. Such therapy may include heparin, other forms of proteoglycans, warfarin or other forms of vitamin K-antagonists as well as aspirin and other platelet aggregation inhibitors.

In one embodiment of the invention, the bleeding is associated with haemophilia A or B. In another embodiment, the bleeding is associated with haemophilia with aquired inhibitors. In another embodiment, the bleeding is associated with thrombocytopenia. In another embodiment, the bleeding is associated with von Willebrand's disease. In another embodiment, the bleeding is associated with severe tissue damage. In another embodiment, the bleeding is associated with severe trauma. In another embodiment, the bleeding is associated with surgery. In another embodiment, the bleeding is associated with laparoscopic surgery. In another embodiment, the bleeding is associated with haemorrhagic gastritis. In another embodiment, the bleeding is profuse uterine bleeding. In another embodiment, the bleeding is occurring in organs with a limited possibility for mechanical haemostasis. In another embodiment, the bleeding is occurring in the brain, inner ear region or eyes. In another embodiment, the bleeding is associated with the process of taking biopsies. In another embodiment, the bleeding is associated with anticoagulant therapy.

The term "subject" as used herein is intended to mean any animal, in particular mammals, such as humans, and may, where appropriate, be used interchangeably with the term "patient".

The terminology for amino acid substitutions used herein is as follows. The first letter represent the amino acid naturally present at a position of SEQ ID NO: 1. The following number represent the position in SEQ ID NO: 1. The second letter represent the different amino acid substituting for the natural amino acid. An example is S43N, where a serine at position 43 of SEQ ID NO: 1 is replaced by an Asparagine. In another example, K62E/I69A, the lysine in position 62 of SEQ ID NO: 1 is replaced by a glutamic acid and the isoleucine in position 69 of SEQ ID NO: 1 is replaced by an alanine in the same Factor VII polypeptide. I69A-FVII thus means human wild type FVII, wherein a isoleucine in position 69 of SEQ ID NO: 1 has been replaced by an alanine.

In one aspect the present invention relates to a composition comprising wild type human FVIIa and a Factor VII polypeptide with a Tissue Factor binding affinity lower than recombinant wild type human Factor VIIa and substantially the same activity or increased activity compared to recombinant wild type human Factor VIIa.

In a further aspect the present invention relates to a method for the treatment of bleeding episodes in a subject or for the enhancement of the normal haemostatic system, the method comprising administering to a subject in need thereof a therapeutically or prophylactically effective amount of:

a) composition comprising wild type human FVIIa and a Factor VII polypeptide with a Tissue Factor binding affinity lower than recombinant wild type human Factor VIIa and substantially the same activity or increased activity compared to recombinant wild type human Factor Vila; or b) a first composition comprising wild type human FVIIa and a second composition comprising a Factor VII polypeptide with a Tissue Factor binding affinity lower than recombinant wild type human Factor VIIa and substantially the same activity or increased activity compared to recombinant wild type human Factor VIIa.

In a further aspect the present invention relates to a process for preparing a composition comprising wild type human FVIIa and a Factor VII polypeptide with a Tissue Factor binding affinity lower than recombinant wild type human Factor VIIa and substantially the same activity or increased activity compared to recombinant wild type human Factor VIIa, wherein the process comprises the step of: mixing wild type human FVIIa with a Factor VII polypeptide with a Tissue Factor binding affinity lower than recombinant wild type human Factor VIIa and substantially the same activity or increased activity compared to recombinant wild type human Factor VIIa in an aqueous medium.

In a further aspect the present invention relates to a use of a composition comprising wild type human FVIIa and a Factor VII polypeptide with a Tissue Factor binding affinity lower than recombinant wild type human Factor VIIa and substantially the same activity or increased activity compared to recombinant wild type human Factor VIIa, for the preparation of a medicament for the treatment of bleeding episodes in a subject or for the enhancement of the normal haemostatic system.

In a further aspect the present invention relates to the use of a Factor VII polypeptide with a Tissue Factor binding affinity lower than recombinant wild type human Factor VIIa and substantially the same activity or increased activity compared to recombinant wild type human Factor VIIa; in the therapeutic treatment of bleedings, where the exposure of TF is high, such as indications where there is a risk of plaque rupture, plaque disruption after percutaneous trans-luminal coronary angioplasty (PTCA) procedures, sepsis, or other bleeding complications, where inflammatory conditions where increased quantities of tissue factor is seen. In one embodiment the bleedings, where the exposure of TF is high is a coagulation disorder, such as disseminated intravascular coagulation (DIC).

The present invention also encompasses methods and compositions that provide combination therapies in which the Factor VII polypeptide with a Tissue Factor binding affinity lower than recombinant wild type human Factor VIIa and substantially the same activity or increased activity compared to recombinant wild type human Factor VIIa is administered with another procoagulant compound, antifibrinolytic compound or regulator of anticoagulant compounds. Suitable compounds include, without limitation, FVIII (such as Refacto® (Genetics Institute), Kogenate FS® (Bayer), Monoclate-P® (Aventis Behring)), Factor XIII (see, e.g., WO 01/85198); inhibitors of tissue factor pathway inhibitor (TFPI inhibitors) (see, e.g., WO 01/85199); Factor IX (see, e.g., WO 02/062376); thrombin activatable fibrinolysis inhibitor (TAFI) (see, e.g., PCT/DK02/00734; PAI-1 (see, e.g., PCT/DK02/00735; Factor V (see, e.g., PCT/DK02/00736); protein C inhibitors (see, e.g., PCT/DK02/00737); thrombomodulin (see, e.g., PCT/DK02/00738); protein S inhibitors (see, e.g., PCT/DK02/00739); tissue plasminogen activator inhibitors (see, e.g., PCT/DK02/00740); alpha2-antiplasmin (see, e.g., PCT/DK02/00741); aprotinin (see, e.g., PCT/DK02/00742); tranexamic acid (see, e.g., PCT/DK02/00751); epsilon-aminocaproic acid (see, e.g., PCT/DK02/00752); prothrombin, thrombin, Factor VII, Factor X, Factor XI and fibrinogen, artificial oxygen carriers (such as POLYHEME®, Northfield lab), colloids (such as Hextend, BioTime, Inc), Desmopressin (such as DDAVP® Tablets (desmopressin acetate) Adventis Pharmaceuticals), activated prothrombin complex concentrates (i.e., Bebulin, Proplex-T, Profiline, Autoplex, FEIBA), Clopidogrel, Ticlopidine, Glycoprotein IIB/IIIA antagonists (Abciximab), LMWH, Warfarin. Streptokinase, Tissue plasminogen activator (tPA)/tPA mutants.

In one embodiment the Factor VII polypeptide with a Tissue Factor binding affinity lower than recombinant wild type human Factor VIIa and substantially the same activity or increased activity compared to recombinant wild type human Factor VIIa is as disclosed in any of international patent applications WO 99/20767, WO 00/66753, WO 01/58935, WO 03/93465 and WO 04/029091, each of which is hereby incorporated by reference in its entirety.

In the present specification, amino acids are represented using abbreviations, as indicated in table 1, approved by IUPAC-IUB Commission on Biochemical Nomenclature (CBN). Amino acid and the like having isomers represented by name or the following abbreviations are in natural L-form unless otherwise indicated. Further, the left and right ends of an amino acid sequence of a peptide are, respectively, the N- and C-termini unless otherwise specified.

TABLE 1

Abbreviations for amino acids:

| Amino acid | Tree-letter code | One-letter code |
|---|---|---|
| Glycine | Gly | G |
| Proline | Pro | P |
| Alanine | Ala | A |
| Valine | Val | V |
| Leucine | Leu | L |
| Isoleucine | Ile | I |
| Methionine | Met | M |
| Cysteine | Cys | C |
| Phenylalanine | Phe | F |
| Tyrosine | Tyr | Y |
| Tryptophan | Trp | W |
| Histidine | His | H |
| Lysine | Lys | K |
| Arginine | Arg | R |
| Glutamine | Gln | Q |
| Asparagine | Asn | N |
| Glutamic Acid | Glu | E |
| Aspartic Acid | Asp | D |
| Serine | Ser | S |
| Threonine | Thr | T |

The invention also relates to a method of preparing human Factor VII polypeptides as mentioned above. The human Factor VII polypeptides are preferably produced by recombinant DNA techniques. To this end, DNA sequences encoding human Factor VII may be isolated by preparing a genomic or cDNA library and screening for DNA sequences coding for all or part of the protein by hybridization using synthetic oligonucleotide probes in accordance with standard techniques (cf. Sambrook et al., *Molecular Cloning: A Laboratory Manual*, Cold Spring Harbor Laboratory, Cold Spring Harbor, N.Y., 1989). For the present purpose, the DNA sequence encoding the protein is preferably of human origin, i.e. derived from a human genomic DNA or cDNA library.

The DNA sequences encoding the human Factor VII polypeptides may also be prepared synthetically by established standard methods, e.g. the phosphoamidite method described by Beaucage and Caruthers, *Tetrahedron Letters* 22 (1981), 1859-1869, or the method described by Matthes et al., *EMBO Journal* 3 (1984), 801-805. According to the phosphoamidite method, oligonucleotides are synthesized, e.g. in an automatic DNA synthesizer, purified, annealed, ligated and cloned in suitable vectors.

The DNA sequences may also be prepared by polymerase chain reaction using specific primers, for instance as described in U.S. Pat. No. 4,683,202, Saiki et al., *Science* 239 (1988), 487-491, or Sambrook et al., supra.

The DNA sequences encoding the human Factor VII polypeptides are usually inserted into a recombinant vector which may be any vector, which may conveniently be subjected to recombinant DNA procedures, and the choice of vector will often depend on the host cell into which it is to be introduced. Thus, the vector may be an autonomously replicating vector, i.e. a vector, which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The vector is preferably an expression vector in which the DNA sequence encoding the human Factor VII polypeptides is operably linked to additional segments required for transcription of the DNA. In general, the expression vector is derived from plasmid or viral DNA, or may contain elements of both. The term, "operably linked" indicates that the segments are arranged so that they function in concert for their intended purposes, e.g. transcription initiates in a promoter and proceeds through the DNA sequence coding for the polypeptide.

The promoter may be any DNA sequence, which shows transcriptional activity in the host cell of choice and may be derived from genes encoding proteins either homologous or heterologous to the host cell.

Examples of suitable promoters for directing the transcription of the DNA encoding the human Factor VII polypeptide in mammalian cells are the SV40 promoter (Subramani et al., *Mol. Cell. Biol.* 1 (1981), 854-864), the MT-1 (metallothionein gene) promoter (Palmiter et al., *Science* 222 (1983), 809-814), the CMV promoter (Boshart et al., *Cell* 41:521-530, 1985) or the adenovirus 2 major late promoter (Kaufman and Sharp, *Mol. Cell. Biol,* 2:1304-1319, 1982).

An example of a suitable promoter for use in insect cells is the polyhedrin promoter (U.S. Pat. No. 4,745,051; Vasuvedan et al., *FEBS Lett.* 311, (1992) 7-11), the P10 promoter (J. M. Vlak et al., *J. Gen. Virology* 69, 1988, pp. 765-776), the *Autographa californica* polyhedrosis virus basic protein promoter (EP 397 485), the baculovirus immediate early gene 1 promoter (U.S. Pat. No. 5,155,037; U.S. Pat. No. 5,162,222), or the baculovirus 39K delayed-early gene promoter (U.S. Pat. No. 5,155,037; U.S. Pat. No. 5,162,222).

Examples of suitable promoters for use in yeast host cells include promoters from yeast glycolytic genes (Hitzeman et al., *J. Biol. Chem.* 255 (1980), 12073-12080; Alber and Kawasaki, *J. Mol. Appl. Gen.* 1 (1982), 419-434) or alcohol dehydrogenase genes (Young et al., in *Genetic Engineering of Microorganisms for Chemicals* (Hollaender et al, eds.), Plenum Press, New York, 1982), or the TPI1 (U.S. Pat. No. 4,599,311) or ADH2-4c (Russell et al., *Nature* 304 (1983), 652-654) promoters.

Examples of suitable promoters for use in filamentous fungus host cells are, for instance, the ADH3 promoter (McKnight et al., *The EMBO J.* 4 (1985), 2093-2099) or the tpiA promoter. Examples of other useful promoters are those derived from the gene encoding *A. oryzae* TAKA amylase, *Rhizomucor miehei* aspartic proteinase, *A. niger* neutral α-amylase, *A. niger* acid stable α-amylase, *A. niger* or *A. awamori* glucoamylase (gluA), *Rhizomucor miehei* lipase, *A. oryzae* alkaline protease, *A. oryzae* triose phosphate isomerase or *A. nidulans* acetamidase. Preferred are the TAKA-amylase and gluA promoters. Suitable promoters are mentioned in, e.g. EP 238 023 and EP 383 779.

The DNA sequences encoding the human Factor VII polypeptides may also, if necessary, be operably connected to a suitable terminator, such as the human growth hormone terminator (Palmiter et al., *Science* 222, 1983, pp. 809-814) or the TPI1 (Alber and Kawasaki, *J. Mol. Appl. Gen.* 1, 1982, pp. 419-434) or ADH3 (McKnight et al., *The EMBO J.* 4, 1985, pp. 2093-2099) terminators. The vector may also contain a set of RNA splice sites located downstream from the promoter and upstream from the insertion site for the Factor VII sequence itself. Preferred RNA splice sites may be obtained from adenovirus and/or immunoglobulin genes. Also contained in the expression vectors is a polyadenylation signal located downstream of the insertion site. Particularly preferred polyadenylation signals include the early or late polyadenylation signal from SV40 (Kaufman and Sharp, ibid.), the polyadenylation signal from the adenovirus 5 Elb region, the human growth hormone gene terminator (DeNoto et al. *Nuc. Acids Res.* 9:3719-3730, 1981) or the polyadenylation signal from the human Factor VII gene or the bovine Factor VII gene. The expression vectors may also include a noncoding viral leader sequence, such as the adenovirus 2 tripartite leader, located between the promoter and the RNA splice sites; and enhancer sequences, such as the SV40 enhancer.

The recombinant vector may further comprise a DNA sequence enabling the vector to replicate in the host cell in question. An example of such a sequence (when the host cell is a mammalian cell) is the SV40 origin of replication.

When the host cell is a yeast cell, suitable sequences enabling the vector to replicate are the yeast plasmid 2μ replication genes REP 1-3 and origin of replication.

The vector may also comprise a selectable marker, e.g. a gene the product of which complements a defect in the host cell, such as the gene coding for dihydrofolate reductase (DHFR) or the *Schizosaccharomyces pombe* TPI gene (described by P. R. Russell, *Gene* 40, 1985, pp. 125-130), or one which confers resistance to a drug, e.g. ampicillin, kanamycin, tetracyclin, chloramphenicol, neomycin, hygromycin or methotrexate. For filamentous fungi, selectable markers include amdS, pyrG, argB, niaD or sC.

To direct the human Factor VII polypeptides of the present invention into the secretory pathway of the host cells, a secretory signal sequence (also known as a leader sequence, prepro sequence or pre sequence) may be provided in the recombinant vector. The secretory signal sequence is joined to the DNA sequences encoding the human Factor VII polypeptides in the correct reading frame. Secretory signal sequences are commonly positioned 5' to the DNA sequence encoding the peptide. The secretory signal sequence may be that, normally associated with the protein or may be from a gene encoding another secreted protein.

For secretion from yeast cells, the secretory signal sequence may encode any signal peptide, which ensures efficient direction of the expressed human Factor VII polypeptides into the secretory pathway of the cell. The signal peptide may be naturally occurring signal peptide, or a functional part thereof, or it may be a synthetic peptide. Suitable signal peptides have been found to be the α-factor signal peptide (cf. U.S. Pat. No. 4,870,008), the signal peptide of mouse salivary amylase (cf. O. Hagenbuchle et al., *Nature* 289, 1981, pp. 643-646), a modified carboxypeptidase signal peptide (cf. L. A. Valls et al., *Cell* 48, 1987, pp. 887-897), the yeast BAR1 signal peptide (cf. WO 87/02670), or the yeast aspartic protease 3 (YAP3) signal peptide (cf. M. Egel-Mitani et al., *Yeast* 6, 1990, pp. 127-137).

For efficient secretion in yeast, a sequence encoding a leader peptide may also be inserted downstream of the signal sequence and upstream of the DNA sequence encoding the human Factor VII polypeptides. The function of the leader peptide is to allow the expressed peptide to be directed from the endoplasmic reticulum to the Golgi apparatus and further to a secretory vesicle for secretion into the culture medium (i.e. exportation of the human Factor VII polypeptides across the cell wall or at least through the cellular membrane into the periplasmic space of the yeast cell). The leader peptide may be the yeast alpha-factor leader (the use of which is described in e.g. U.S. Pat. No. 4,546,082, U.S. Pat. No. 4,870,008, EP 16 201, EP 123 294, EP 123 544 and EP 163 529). Alternatively, the leader peptide may be a synthetic leader peptide, which is to say a leader peptide not found in nature. Synthetic leader peptides may, for instance, be constructed as described in WO 89/02463 or WO 92/11378.

For use in filamentous fungi, the signal peptide may conveniently be derived from a gene encoding an *Aspergillus* sp. amylase or glucoamylase, a gene encoding a *Rhizomucor miehei* lipase or protease or a *Humicola lanuginosa* lipase. The signal peptide is preferably derived from a gene encoding *A. oryzae* TAKA amylase, *A. niger* neutral α-amylase, *A.*

*niger* acid-stable amylase, or *A. niger* glucoamylase. Suitable signal peptides are disclosed in, e.g. EP 238 023 and EP 215 594.

For use in insect cells, the signal peptide may conveniently be derived from an insect gene (cf. WO 90/05783), such as the lepidopteran *Manduca sexta* adipokinetic hormone precursor signal peptide (cf. U.S. Pat. No. 5,023,328).

The procedures used to ligate the DNA sequences coding for the human Factor VII polypeptides, the promoter and optionally the terminator and/or secretory signal sequence, respectively, and to insert them into suitable vectors containing the information necessary for replication, are well known to persons skilled in the art (cf., for instance, Sambrook et al., *Molecular Cloning: A Laboratory Manual*, Cold Spring Harbor, N.Y., 1989).

Methods of transfecting mammalian cells and expressing DNA sequences introduced in the cells are described in e.g. Kaufman and Sharp, *J. Mol. Biol.* 159 (1982), 601-621; Southern and Berg, *J. Mol. Appl. Genet.* 1 (1982), 327-341; Loyter et al., *Proc. Natl. Acad. Sci. USA* 79 (1982), 422-426; Wigler et al., *Cell* 14 (1978), 725; Corsaro and Pearson, *Somatic Cell Genetics* 7 (1981), 603, Graham and van der Eb, *Virology* 52 (1973), 456; and Neumann et al., *EMBO J.* 1 (1982), 841-845.

Selectable markers may be introduced into the cell on a separate plasmid at the same time as the gene of interest, or they may be introduced on the same plasmid. If on the same plasmid, the selectable marker and the gene of interest may be under the control of different promoters or the same promoter, the latter arrangement producing a dicistronic message. Constructs of this type are known in the art (for example, Levinson and Simonsen, U.S. Pat. No. 4,713,339). It may also be advantageous to add additional DNA, known as "carrier DNA," to the mixture that is introduced into the cells.

After the cells have taken up the DNA, they are grown in an appropriate growth medium, typically 1-2 days, to begin expressing the gene of interest. As used herein the term "appropriate growth medium" means a medium containing nutrients and other components required for the growth of cells and the expression of the human Factor VII polypeptides of interest. Media generally include a carbon source, a nitrogen source, essential amino acids, essential sugars, vitamins, salts, phospholipids, protein and growth factors. For production of gamma-carboxylated proteins, the medium will contain vitamin K, preferably at a concentration of about 0.1 µg/ml to about 5 µg/ml. Drug selection is then applied to select for the growth of cells that are expressing the selectable marker in a stable fashion. For cells that have been transfected with an amplifiable selectable marker the drug concentration may be increased to select for an increased copy number of the cloned sequences, thereby increasing expression levels. Clones of stably transfected cells are then screened for expression of the human Factor VII polypeptide of interest.

The host cell into which the DNA sequences encoding the human Factor VII polypeptides is introduced may be any cell, which is capable of producing the posttranslational modified human Factor VII polypeptides and includes yeast, fungi and higher eucaryotic cells.

Examples of mammalian cell lines for use in the present invention are the COS-1 (ATCC CRL 1650), baby hamster kidney (BHK) and 293 (ATCC CRL 1573; Graham et al., *J. Gen. Virol.* 36:59-72, 1977) cell lines. A preferred BHK cell line is the tk⁻ ts13 BHK cell line (Waechter and Baserga, *Proc. Natl. Acad. Sci. USA* 79:1106-1110, 1982, incorporated herein by reference), hereinafter referred to as BHK 570 cells. The BHK 570 cell line has been deposited with the American Type Culture Collection, P.O. Box 1549, Manassas, Va. 20108, under ATCC accession number CRL 10314. A tk⁻ ts13 BHK cell line is also available from the ATCC under accession number CRL 1632. In addition, a number of other cell lines may be used within the present invention, including Rat Hep I (Rat hepatoma; ATCC CRL 1600), Rat Hep II (Rat hepatoma; ATCC CRL 1548), TCMK (ATCC CCL 139), Human lung (ATCC HB 8065), NCTC 1469 (ATCC CCL 9.1), CHO (ATCC CCL 61) and DUKX cells (Urlaub and Chasin, *Proc. Natl. Acad. Sci. USA* 77:4216-4220, 1980).

Examples of suitable yeasts cells include cells of *Saccharomyces* spp. or *Schizosaccharomyces* spp., in particular strains of *Saccharomyces cerevisiae* or *Saccharomyces kluyveri*. Methods for transforming yeast cells with heterologous DNA and producing heterologous polypeptides there from are described, e.g. in U.S. Pat. Nos. 4,599,311, 4,931,373, 4,870,008, 5,037,743, and 4,845,075, all of which are hereby incorporated by reference. Transformed cells are selected by a phenotype determined by a selectable marker, commonly drug resistance or the ability to grow in the absence of a particular nutrient, e.g. leucine. A preferred vector for use in yeast is the POT1 vector disclosed in U.S. Pat. No. 4,931,373. The DNA sequences encoding the human Factor VII polypeptides may be preceded by a signal sequence and optionally a leader sequence, e.g. as described above. Further examples of suitable yeast cells are strains of *Kluyveromyces*, such as *K. lactis*, *Hansenula*, e.g. *H. polymorpha*, or *Pichia*, e.g. *P. pastoris* (cf. Gleeson et al., *J. Gen. Microbiol.* 132, 1986, pp. 3459-3465; U.S. Pat. No. 4,882,279).

Examples of other fungal cells are cells of filamentous fungi, e.g. *Aspergillus* spp., *Neurospora* spp., *Fusarium* spp. or *Trichoderma* spp., in particular strains of *A. oryzae*, *A. nidulans* or *A. niger*. The use of *Aspergillus* spp. for the expression of proteins is described in, e.g., EP 272 277, EP 238 023, EP 184 438 The transformation of *F. oxysporum* may, for instance, be carried out as described by Malardier et al., 1989, *Gene* 78: 147-156. The transformation of *Trichoderma* spp. may be performed for instance as described in EP 244 234.

When a filamentous fungus is used as the host cell, it may be transformed with the DNA construct of the invention, conveniently by integrating the DNA construct in the host chromosome to obtain a recombinant host cell. This integration is generally considered to be an advantage as the DNA sequence is more likely to be stably maintained in the cell. Integration of the DNA constructs into the host chromosome may be performed according to conventional methods, e.g. by homologous or heterologous recombination.

Transformation of insect cells and production of heterologous polypeptides therein may be performed as described in U.S. Pat. No. 4,745,051; U.S. Pat. No. 4,879,236; U.S. Pat. Nos. 5,155,037; 5,162,222; EP 397,485) all of which are incorporated herein by reference. The insect cell line used as the host may suitably be a *Lepidoptera* cell line, such as *Spodoptera frugiperda* cells or *Trichoplusia ni* cells (cf. U.S. Pat. No. 5,077,214). Culture conditions may suitably be as described in, for instance, WO 89/01029 or WO 89/01028, or any of the aforementioned references.

The transformed or transfected host cell described above is then cultured in a suitable nutrient medium under conditions permitting expression of the human Factor VII polypeptide after which all or part of the resulting peptide may be recovered from the culture. The medium used to culture the cells may be any conventional medium suitable for growing the host cells, such as minimal or complex media containing appropriate supplements. Suitable media are available from commercial suppliers or may be prepared according to published recipes (e.g. in catalogues of the American Type Culture Collection). The human Factor VII polypeptide produced by the cells may then be recovered from the culture medium by conventional procedures including separating the host cells from the medium by centrifugation or filtration, precipitating the proteinaqueous components of the supernatant or filtrate by means of a salt, e.g. ammonium sulphate, purification by a variety of chromatographic procedures, e.g. ion exchange chromatography, gelfiltration chromatography, affinity chromatography, or the like, dependent on the type of polypeptide in question.

For the preparation of recombinant human Factor VII polypeptides, a cloned wild-type Factor VII DNA sequence is used. This sequence may be modified to encode a desired Factor VII variant. The complete nucleotide and amino acid sequences for human Factor VII are known. See U.S. Pat. No. 4,784,950, which is incorporated herein by reference, where the cloning and expression of recombinant human Factor VII is described. The bovine Factor VII sequence is described in Takeya et al., *J. Biol. Chem.*, 263:14868-14872 (1988), which is incorporated by reference herein.

The amino acid sequence alterations may be accomplished by a variety of techniques. Modification of the DNA sequence may be by site-specific mutagenesis. Techniques for site-specific mutagenesis are well known in the art and are described by, for example, Zoller and Smith (*DNA* 3:479-488, 1984). Thus, using the nucleotide and amino acid sequences of Factor VII, one may introduce the alterations of choice.

DNA sequences for use within the present invention will typically encode a pre-pro peptide at the amino-terminus of the Factor VII protein to obtain proper post-translational processing (e.g. gamma-carboxylation of glutamic acid residues) and secretion from the host cell. The pre-pro peptide may be that of Factor VII or another vitamin K-dependent plasma protein, such as factor IX, factor X, prothrombin, protein C or protein S. As will be appreciated by those skilled in the art, additional modifications can be made in the amino acid sequence of Factor VII where those modifications do not significantly impair the ability of the protein to act as a coagulation factor. For example, Factor VII in the catalytic triad can also be modified in the activation cleavage site to inhibit the conversion of zymogen Factor VII into its activated two-chain form, as generally described in U.S. Pat. No. 5,288,629, incorporated herein by reference.

Within the present invention, transgenic animal technology may be employed to produce the human Factor VII polypeptide. It is preferred to produce the proteins within the mammary glands of a host female mammal. Expression in the mammary gland and subsequent secretion of the protein of interest into the milk overcomes many difficulties encountered in isolating proteins from other sources. Milk is readily collected, available in large quantities, and well characterized biochemically. Furthermore, the major milk proteins are present in milk at high concentrations (typically from about 1 to 15 g/l). From a commercial point of view, it is clearly preferable to use as the host a species that has a large milk yield. While smaller animals such as mice and rats can be used (and are preferred at the proof of principle stage), within the present invention it is preferred to use livestock mammals including, but not limited to, pigs, goats, sheep and cattle. Sheep are particularly preferred due to such factors as the previous history of transgenesis in this species, milk yield, cost and the ready availability of equipment for collecting sheep milk. See WIPO Publication WO 88/00239 for a comparison of factors influencing the choice of host species. It is generally desirable to select a breed of host animal that has been bred for dairy use, such as East Friesland sheep, or to introduce dairy stock by breeding of the transgenic line at a later date. In any event, animals of known, good health status should be used.

To obtain expression in the mammary gland, a transcription promoter from a milk protein gene is used. Milk protein genes include those genes encoding caseins (see U.S. Pat. No. 5,304,489, incorporated herein by reference), beta-lactoglobulin, alpha-lactalbumin, and whey acidic protein. The beta-lactoglobulin (BLG) promoter is preferred. In the case of the ovine beta-lactoglobulin gene, a region of at least the proximal 406 bp of 5' flanking sequence of the gene will generally be used, although larger portions of the 5' flanking sequence, up to about 5 kbp, are preferred, such as about 4.25 kbp DNA segment encompassing the 5' flanking promoter and non-coding portion of the beta-lactoglobulin gene. See Whitelaw et al., *Biochem J.* 286: 31-39 (1992). Similar fragments of promoter DNA from other species are also suitable.

Other regions of the beta-lactoglobulin gene may also be incorporated in constructs, as may genomic regions of the gene to be expressed. It is generally accepted in the art that constructs lacking introns, for example, express poorly in comparison with those that contain such DNA sequences (see Brinster et al., *Proc. Natl. Acad. Sci. USA* 85: 836-840 (1988); Palmiter et al., *Proc. Natl. Acad. Sci. USA* 88: 478-482 (1991); Whitelaw et al., *Transgenic Res.* 1: 3-13 (1991); WO 89/01343; and WO 91/02318, each of which is incorporated herein by reference). In this regard, it is generally preferred, where possible, to use genomic sequences containing all or some of the native introns of a gene encoding the protein or polypeptide of interest, thus the further inclusion of at least some introns from, e.g, the beta-lactoglobulin gene, is preferred. One such region is a DNA segment which provides for intron splicing and RNA polyadenylation from the 3' non-coding region of the ovine beta-lactoglobulin gene. When substituted for the natural 3' non-coding sequences of a gene, this ovine beta-lactoglobulin segment can both enhance and stabilize expression levels of the protein or polypeptide of interest. Within other embodiments, the region surrounding the initiation ATG of the sequence encoding the human Factor VII polypeptide is replaced with corresponding sequences from a milk specific protein gene. Such replacement provides a putative tissue-specific initiation environment to enhance expression. It is convenient to replace the entire pre-pro sequence of the human Factor VII polypeptide and 5' non-coding sequences with those of, for example, the BLG gene, although smaller regions may be replaced.

For expression of a human Factor VII polypeptide in transgenic animals, a DNA segment encoding the human Factor VII polypeptide is operably linked to additional DNA segments required for its expression to produce expression units. Such additional segments include the above-mentioned promoter, as well as sequences which provide for termination of transcription and polyadenylation of mRNA. The expression units will further include a DNA segment encoding a secretory signal sequence operably linked to the segment encoding the human Factor VII polypeptide. The secretory signal sequence may be a native secretory signal sequence of the human Factor VII polypeptide or may be that of another protein, such as a milk protein. See, for example, von Heinje, *Nuc. Acids Res.* 14: 4683-4690 (1986); and Meade et al., U.S. Pat. No. 4,873,316, which are incorporated herein by reference.

Construction of expression units for use in transgenic animals is conveniently carried out by inserting a sequence encoding the human Factor VII polypeptide into a plasmid or phage vector containing the additional DNA segments, although the expression unit may be constructed by essentially any sequence of ligations. It is particularly convenient to provide a vector containing a DNA segment encoding a milk protein and to replace the coding sequence for the milk protein with that of the human Factor VII polypeptide, thereby creating a gene fusion that includes the expression control sequences of the milk protein gene. In any event, cloning of the expression units in plasmids or other vectors facilitates the amplification of the human Factor VII polypeptide. Amplification is conveniently carried out in bacterial (e.g. E. coli) host cells, thus the vectors will typically include an origin of replication and a selectable marker functional in bacterial host cells.

The expression unit is then introduced into fertilized eggs (including early-stage embryos) of the chosen host species. Introduction of heterologous DNA can be accomplished by one of several routes, including microinjection (e.g. U.S. Pat. No. 4,873,191), retroviral infection (Jaenisch, *Science* 240: 1468-1474 (1988)) or site-directed integration using embryonic stem (ES) cells (reviewed by Bradley et al., *Bio/Technology* 10: 534-539 (1992)). The eggs are then implanted into the oviducts or uteri of pseudopregnant females and allowed to develop. Offspring carrying the introduced DNA in their germ line can pass the DNA on to their progeny in the normal, Mendelian fashion, allowing the development of transgenic herds.

General procedures for producing transgenic animals are known in the art. See, for example, Hogan et al., *Manipulating the Mouse Embryo: A Laboratory Manual*, Cold Spring Harbor Laboratory, 1986; Simons et al., *Bio/Technology* 6: 179-183 (1988); Wall et al., Biol. Reprod. 32: 645-651 (1985); Buhler et al., *Bio/Technology* 8: 140-143 (1990); Ebert et al., *Bio/Technology* 9: 835-838 (1991); Krimpenfort et al., *Bio/Technology* 9: 844-847 (1991); Wall et al., *J. Cell. Biochem.* 49: 113-120 (1992); U.S. Pat. Nos. 4,873,191 and 4,873,316; WIPO publications WO 88/00239, WO 90/05188, WO 92/11757; and GB 87/00458, which are incorporated herein by reference. Techniques for introducing foreign DNA sequences into mammals and their germ cells were originally developed in the mouse. See, e.g., Gordon et al., *Proc. Natl. Acad. Sci. USA* 77: 7380-7384 (1980); Gordon and Ruddle, *Science* 214: 1244-1246 (1981); Palmiter and Brinster, *Cell* 41: 343-345 (1985); and Brinster et al., *Proc. Natl. Acad. Sci. USA* 82: 4438-4442 (1985). These techniques were subsequently adapted for use with larger animals, including livestock species (see e.g., WIPO publications WO 88/00239, WO 90/05188, and WO 92/11757; and Simons et al., *Bio/Technology* 6: 179-183 (1988). To summarize, in the most efficient route used to date in the generation of transgenic mice or livestock, several hundred linear molecules of the DNA of interest are injected into one of the pro-nuclei of a fertilized egg according to established techniques. Injection of DNA into the cytoplasm of a zygote can also be employed. Production in transgenic plants may also be employed. Expression may be generalized or directed to a particular organ, such as a tuber. See, Hiatt, *Nature* 344:469-479 (1990); Edelbaum et al., *J. Interferon Res.* 12:449-453 (1992); Sijmons et al., *Bio/Technology* 8:217-221 (1990); and European Patent Office Publication EP 255,378.

Factor VII produced according to the present invention may be purified by affinity chromatography on an anti-Factor VII antibody column. It is preferred that the immunoadsorption column comprise a high-specificity monoclonal antibody. The use of calcium-dependent monoclonal antibodies, as described by Wakabayashi et al., *J. Biol. Chem.*, 261: 11097-11108, (1986) and Thim et al., *Biochem.* 27: 7785-7793, (1988), incorporated by reference herein, is particularly preferred. Additional purification may be achieved by conventional chemical purification means, such as high performance liquid chromatography. Other methods of purification, including barium citrate precipitation, are known in the art, and may be applied to the purification of the Factor VII described herein (see, generally, Scopes, R., *Protein Purification*, Springer-Verlag, New York, 1982). Substantially pure Factor VII of at least about 90 to 95% homogeneity is preferred, and 98 to 99% or more homogeneity most preferred, for pharmaceutical uses. Once purified, partially or to homogeneity as desired, the Factor VII may then be used therapeutically.

Conversion of single-chain Factor VII to active two-chain Factor VIIa may be achieved using factor XIIa as described by Hedner and Kisiel (1983, *J. Clin. Invest.* 71: 1836-1841), or with other proteases having trypsin-like specificity (Kisiel and Fujikawa, *Behring Inst. Mitt.* 73: 29-42, 1983). Alternatively Factor VII may be autoactivated by passing it through an ion-exchange chromatography column, such as mono Q®. (Pharmacia Fire Chemicals) or the like (Bjoern et al., 1986, *Research Disclosures* 269:564-565). The Factor VII molecules of the present invention and pharmaceutical compositions thereof are particularly useful for administration to humans to treat a variety of conditions involving intravascular coagulation.

The invention also provides suitable assays for selecting preferred Factor VIIa polypeptides and Factor VIIa derivatives according to the invention. These assays can be performed as a simple preliminary in vitro test.

Thus, Example 3 herein discloses a simple test (entitled "In Vitro Hydrolysis Assay") for the activity of Factor VIIa polypeptides of the invention. Based thereon, Factor VIIa polypeptides which are of particular interest are such polypeptides where the ratio between the activity of the variant and the activity of native human Factor VII shown in FIG. 1 is about 1.0 or higher, when tested in the "In Vitro Hydrolysis Assay" defined herein.

The activity of the polypeptides can also be measured using a physiological substrate such as factor X ("In Vitro Proteolysis Assay") (see Example 4), suitably at a concentration of 100-1000 nM, where the factor Xa generated is measured after the addition of a suitable chromogenic substrate (e.g. S-2765). In addition, the activity assay may be run at physiological temperature.

The ability of the procoagulant Factor VIIa polypeptides to generate thrombin can also be measured in an assay comprising all relevant coagulation factors and inhibitors at physiological concentrations (minus factor VIII when mimicking haemophilia A conditions) and activated platelets (as described on p. 543 in Monroe et al. (1997) *Brit. J. Haematol.* 99, 542-547 which is hereby incorporated as reference).

The procoagulant Factor VII polypeptides according to the present invention may be used to control bleeding disorders which have several causes such as clotting factor deficiencies (e.g. haemophilia A and B or deficiency of coagulation factors XI or VII) or clotting factor inhibitors, or they may be used to control excessive bleeding occurring in subjects with a normally functioning blood clotting cascade (no clotting factor deficiencies or inhibitors against any of the coagulation factors). The bleedings may be caused by a defective platelet function, thrombocytopenia or von Willebrand's disease. They may also be seen in subjects in whom an increased fibrinolytic activity has been induced by various stimuli.

In subjects who experience extensive tissue damage in association with surgery or vast trauma, the haemostatic mechanism may be overwhelmed by the demand of immediate haemostasis and they may develop bleedings in spite of a normal haemostatic mechanism. Achieving satisfactory haemostasis is also a problem when bleedings occur in organs such as the brain, inner ear region and eyes and may also be a problem in cases of diffuse bleedings (haemorrhagic gastritis and profuse uterine bleeding) when it is difficult to identify the source. The same problem may arise in the process of taking biopsies from various organs (liver, lung, tumour tissue, gastrointestinal tract) as well as in laparoscopic surgery. These situations share the difficulty of providing haemostasis by surgical techniques (sutures, clips, etc.). Acute and profuse bleedings may also occur in subjects on anticoagulant therapy in whom a defective haemostasis has been induced by the therapy given. Such subjects may need surgical interventions in case the anticoagulant effect has to be counteracted rapidly. Another situation that may cause problems in the case of unsatisfactory haemostasis is when subjects with a normal haemostatic mechanism are given anticoagulant therapy to prevent thromboembolic disease. Such therapy may include heparin, other forms of proteoglycans, warfarin or other forms of vitamin K-antagonists as well as aspirin and other platelet aggregation inhibitors.

A systemic activation of the coagulation cascade may lead to disseminated intravascular coagulation (DIC). However, such complications have not been seen in subjects treated with high doses of recombinant Factor VIIa because of a localised haemostatic process of the kind induced by the complex formation between Factor VIIa and TF exposed at the site of vessel wall injury. The procoagulant Factor VII polypeptides according to the invention may thus also be used in their activated form to control such excessive bleedings associated with a normal haemostatic mechanism.

For treatment in connection with deliberate interventions, the procoagulant Factor VII polypeptides of the invention will typically be administered within about 24 hours prior to performing the intervention, and for as much as 7 days or more thereafter. Administration as a coagulant can be by a variety of routes as described herein.

The dose of the Factor VII polypeptides ranges from about 0.05 mg to 500 mg/day, preferably from about 1 mg to 200 mg/day, and more preferably from about 10 mg to about 175 mg/day for a 70 kg subject as loading and maintenance doses, depending on the severity of the condition.

The pharmaceutical compositions are primarily intended for parenteral administration for prophylactic and/or therapeutic treatment. Preferably, the pharmaceutical compositions are administered parenterally, i.e., intravenously, subcutaneously, or intramuscularly, or it may be administered by continuous or pulsatile infusion. The compositions for parenteral administration comprise the Factor VII polypeptide of the invention in combination with, preferably dissolved in, a pharmaceutically acceptable carrier, preferably an aqueous carrier. A variety of aqueous carriers may be used, such as water, buffered water, 0.4% saline, 0.3% glycine and the like. The Factor VII polypeptides of the invention can also be formulated into liposome preparations for delivery or targeting to the sites of injury. Liposome preparations are generally described in, e.g., U.S. Pat. No. 4,837,028, U.S. Pat. No. 4,501,728, and U.S. Pat. No. 4,975,282. The compositions may be sterilised by conventional, well-known sterilisation techniques. The resulting aqueous solutions may be packaged for use or filtered under aseptic conditions and lyophilised, the lyophilised preparation being combined with a sterile aqueous solution prior to administration. The compositions may contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, etc.

The concentration of Factor VII polypeptide in these formulations can vary widely, i.e., from less than about 0.5% by weight, usually at or at least about 1% by weight to as much as 15 or 20% by weight and will be selected primarily by fluid volumes, viscosities, etc., in accordance with the particular mode of administration selected.

Thus, a typical pharmaceutical composition for intravenous infusion could be made up to contain 250 ml of sterile Ringer's solution and 10 mg of the Factor VII polypeptide. Actual methods for preparing parenterally administrable compositions will be known or apparent to those skilled in the art and are described in more detail in, for example, *Remington's Pharmaceutical Sciences,* 18th ed., Mack Publishing Company, Easton, Pa. (1990).

The compositions containing the Factor VII polypeptides of the present invention can be administered for prophylactic and/or therapeutic treatments. In therapeutic applications, compositions are administered to a subject already suffering from a disease, as described above, in an amount sufficient to cure, alleviate or partially arrest the disease and its complications. An amount adequate to accomplish this is defined as "therapeutically effective amount". As will be understood by the person skilled in the art amounts effective for this purpose will depend on the severity of the disease or injury as well as the weight and general state of the subject. In general, however, the effective amount will range from about 0.05 mg up to about 500 mg of the Factor VII polypeptide per day for a 70 kg subject, with dosages of from about 1.0 mg to about 200 mg of the Factor VII polypeptide per day being more commonly used.

It must be kept in mind that the materials of the present invention may generally be employed in serious disease or injury states, that is, life threatening or potentially life threatening situations. In such cases, in view of the minimisation of extraneous substances and general lack of immunogenicity of human Factor VII polypeptides in humans, it is possible and may be felt desirable by the treating physician to administer a substantial excess of these variant Factor VII compositions.

In prophylactic applications, compositions containing the Factor VII polypeptide of the invention are administered to a subject susceptible to or otherwise at risk of a disease state or injury to enhance the subject's own coagulative capability. Such an amount is defined to be a "prophylactically effective dose." In prophylactic applications, the precise amounts once again depend on the subject's state of health and weight, but the dose generally ranges from about 0.05 mg to about 500 mg per day for a 70-kilogram subject, more commonly from about 1.0 mg to about 200 mg per day for a 70-kilogram subject.

Single or multiple administrations of the compositions can be carried out with dose levels and patterns being selected by the treating physician. For ambulatory subjects requiring daily maintenance levels, the Factor VII polypeptides may be administered by continuous infusion using e.g. a portable pump system.

Local delivery of the Factor VII polypeptide of the present invention, such as, for example, topical application may be carried out, for example, by means of a spray, perfusion, double balloon catheters, stent, incorporated into vascular grafts or stents, hydrogels used to coat balloon catheters, or other well established methods. In any event, the pharmaceutical compositions should provide a quantity of Factor VII polypeptide sufficient to effectively treat the subject.

Inactivated Factor VII polypeptides of the present invention are able to bind to cell-surface tissue factor. For example, DEGR-Factor VIIa binds cell-surface tissue factor with an equivalent or higher affinity than wild-type Factor VIIa. DEGR-Factor VIIa, however, has no enzymatic activity, yet it binds to tissue factor and acts as a competitive antagonist for wild-type Factor VIIa, thereby inhibiting the subsequent steps in the extrinsic pathway of coagulation leading to the generation of thrombin.

Inactivated Factor VII polypeptides are particularly useful for administration to humans to treat a variety of conditions involving intravascular coagulation. For example, although deep vein thrombosis and pulmonary embolism can be treated with conventional anticoagulants, the inactivated Factor VII polypeptides described herein may be used to prevent the occurrence of thromboembolic complications in identified high risk patients, such as those undergoing surgery or those with congestive heart failure. In addition, inactivated Factor VII polypeptides may act as an antagonist for tissue factor-mediated induction of coagulation, thus blocking the production of thrombin and the subsequent deposition of fibrin. As such, inactivated Factor VII polypeptides may be useful for inhibiting tissue factor activity resulting in, for example, the inhibition of blood coagulation, thrombosis or platelet deposition.

The inactivated Factor VII polypeptides may be particularly useful in the treatment of intimal hyperplasia, restenosis due to acute vascular injury, deep venous thrombosis, arterial thrombosis, post surgical thrombosis, coronary artery bypass graft (CABG), percutaneous transdermal coronary angioplastry (PTCA), stroke, cancer, tumour metastasis, angiogenesis, ischemia/reperfusion, rheumatoid arthritis, thrombolysis, arteriosclerosis and restenosis following angioplastry, acute and chronic indications such as inflammation, septic chock, septicemia, hypotension, adult respiratory distress syndrome (ARDS), disseminated intravascular coagulopathy (DIC), pulmonary embolism, platelet deposition, myocardial infarction, or the prophylactic treatment of mammals with atherosclerotic vessels at risk for thrombosis. Acute vascular injuries are those which occur rapidly (i.e. over days to months), in contrast to chronic vascular injuries (e.g. atherosclerosis) which develop over a lifetime. Acute vascular injuries often result from surgical procedures such as vascular reconstruction, wherein the techniques of angioplasty, endarterectomy, atherectomy, vascular graft emplacement or the like are employed. Hyperplasia may also occur as a delayed response in response to, e.g., graft emplacement or organ transplantation. Since inactivated Factor VII polypeptides is more selective than heparin, generally binding only tissue factor which has been exposed at sites of injury, and because inactivated Factor VII polypeptides does not destroy other coagulation proteins, it will be more effective and less likely to cause bleeding complications than heparin when used prophylactically for the prevention of deep vein thrombosis.

Inactivated Factor VII polypeptides which maintain tissue factor binding inhibit platelet accumulation at the site of vascular injury by blocking the production of thrombin and the subsequent deposition of fibrin.

Due to the ability of DEGR-Factor VII to block thrombin generation and limit platelet deposition at sites of acute vascular injury, inactivated Factor VII polypeptides which maintain tissue factor binding activity but lack Factor VIIa enzymatic activity can be used to inhibit vascular restenosis.

Compositions comprising inactivated Factor VII polypeptides are particularly useful in methods for treating patients when formulated into pharmaceutical compositions, where they may be given to individuals suffering from a variety of disease states to treat coagulation-related conditions. Such inactivated Factor VII polypeptides, capable of binding tissue factor but having a substantially reduced ability to catalyze activation of other factors in the clotting cascade, may possess a longer plasma half-life and thus a correspondingly longer period of anticoagulative activity when compared to other anticoagulants. Among the medical indications for the subject compositions are those commonly treated with anticoagulants, such as, for example, deep vein thrombosis, pulmonary embolism, stroke, disseminated intravascular coagulation (DIC), fibrin deposition in lungs and kidneys associated with gram-negative endotoxemia, and myocardial infarction. The compositions can be used to inhibit vascular restenosis as occurs following mechanical vascular injury, such as injury caused by balloon angioplasty, endarterectomy, reductive atherectomy, stent placement, laser therapy or rotablation, or as occurs secondary to vascular grafts, stents, bypass grafts or organ transplants. The compositions can thus be used to inhibit platelet deposition and associated disorders. Thus, a method of inhibiting coagulation, vascular restenosis or platelet deposition, for example, comprises administering to a patient a composition comprising inactivated Factor VII polypeptides, such as that having at least one amino acid substitution in a catalytic triad of Ser344, Asp242 and His193, in an amount sufficient to effectively inhibit coagulation, vascular restenosis or platelet deposition. The methods also find use in the treatment of acute closure of a coronary artery in an individual (e.g. acute myocardial infarction), which comprises administering the inactivated Factor VII polypeptides, which includes Dansyl-Glu-Gly-Arg chloromethylketone Factor VII (DEGR-Factor VII) and Phe-Phe-Arg chloromethylketone Factor VII (FFR-Factor VII), in conjunction with tissue plasminogen activator or streptokinase, and can accelerate tPA induced thrombolysis. The inactivated Factor VII polypeptides is given prior to, in conjunction with, or shortly following administration of a thrombolytic agent, such as tissue plasminogen activator.

Compositions of inactivated Factor VII polypeptides will also have substantial utility in the prevention of cardiogenic emboli and in the treatment of thrombotic strokes. Because of its low potential for causing bleeding complications and its selectivity, Factor VII polypeptides can be given to stroke victims and may prevent the extension of the occluding arterial thrombus. The amount of Factor VII polypeptides administered will vary with each patient depending on the nature and severity of the stroke, but doses will generally be in the range of those suggested below.

Inactivated Factor VII polypeptides and compositions thereof can also be used to inhibit deleterious events associated with ischemic reperfusion. Severe ischemia to a tissue, organ or limb may be due to a decrease in blood flow and may be associated with trauma, surgical manipulation, or lowered blood pressure. One of the complications associated with severe ischemia is the up-regulation of tissue factor in the arterial system. This increased expression of tissue factor is believed to stimulate a procoagulant response, primarily in the capillary bed. Following reperfusion to the ischemic tissue, thrombi can be generated which may be either occlusive or non-occlusive. The generation of thrombi in the arterial bed, and the deposition of platelets along the thrombus, lead to the secondary generation of ischemia to the tissue. The generation of the thrombi and the presence of platelets can then cause the generation and release of multiple bioactive factors, including those generated from the coagulation pathway, such as thrombin and Factor X, as well as factors released from activated platelets. In turn, these factors may induce the generation of additional factors by the underlying endothelial and smooth muscle cells, or by adjacent mononuclear cells, such as TNF-alpha and IL-1. These factors, in turn, can then activate the endothelial cells leading to the up-regulation of various adhesion molecules associated with monocyte and neutrophil binding. The binding and transmigration of monocytes and neutrophils, the release of bioactive compounds by these cells, including the generation of free-oxygen radicals, can exacerbate the level of endothelial cell activation and damage. Ultimately, if the cascade of events goes unchecked, this can lead to systemic complications and the potential to stimulate multiple organ failure. By blocking tissue factor according to the present invention by administering a specific inhibitor for tissue factor/Factor VII binding (e.g., FFR-FVIIa), and thereby blocking the initiation of the extrinsic pathway of coagulation, the initiation of the cascade of events may be prevented, thereby eliminating, or minimizing the deleterious events associated with ischemia/reperfusion.

The dose of inactivated Factor VII polypeptides for prevention of deep vein thrombosis is in the range of about 50 µg to 500 mg/day, more typically 1 mg to 200 mg/day, and more preferably 10 to about 175 mg/day for a 70 kg patient, and administration should begin at least about 6 hours prior to surgery and continue at least until the patient becomes ambulatory. The dose of inactivated Factor VII polypeptides in the treatment for restenosis will vary with each patient but will generally be in the range of those suggested above.

Compositions comprising inactivated Factor VII polypeptides will typically be administered within about 24 hours prior to performing an intervention, and for as much as 7 days or more thereafter. Administration can be by a variety of routes as further described herein. The compositions comprising inactivated Factor VII polypeptides can also be administered systemically or locally for the placement of vascular grafts (e.g., by coating synthetic or modified natural arterial vascular grafts), at sites of anastomosis, surgical endarterectomy (typically carotid artery endarterectomy), bypass grafts, and the like.

In the treatment of established deep vein thrombosis and/or pulmonary embolism, the dose of Factor VII polypeptides ranges from about 50 µg to 500 mg/day, more typically 1 mg to 200 mg/day, and more preferably 10 mg to about 175 mg/day for a 70 kg patient as loading and maintenance doses, depending on the weight of the patient and the severity of the condition. Because of the lower likelihood of bleeding complications from infusions of inactivated Factor VII polypeptides, inactivated Factor VII polypeptides can replace or lower the dose of heparin during or after surgery in conjunction with thrombectomies or embolectomies.

In cases of acute bacteremia, endotoxemia or DIC, the patient is given a loading dose of a Factor VII polypeptide of at least about 50 µg to 500 mg/day, more typically 1 mg to 200 mg/day, and more preferably 10 mg to about 175 mg/day for a 70 kg patient, with maintenance doses thereafter in the range of 50 µg to 500 mg/day, typically 1 mg to 200 mg/day for a 70 kg patient.

Preferably, the Factor VII polypeptide has a half-life ($t_{1/2}$) which is enhanced relative to the half-life of the unconjugated Factor VII from which it was derived. Preferably, the half-life of the Factor VII polypeptide is enhanced by at least 1.5-fold to 2-fold, more preferably by about 2-fold to 3-fold, even more preferably by about 5-fold to 10-fold, optimally about 100-fold, usually about 6-fold relative to the half-life of the unmodified parent Factor VII.

General methods of attaching polyethylene glycol to proteins are disclosed within U.S. Pat. No. 4,179,337 issued Dec. 18, 1979 (incorporated herein by reference to disclose methods of attaching polyethylene glycol to proteins). Further, other methods of attaching polyethylene glycol are disclosed within U.S. Pat. No. 5,122,614 issued Jun. 16, 1992, also incorporated herein by reference to disclose methods of attaching polyethylene glycol to proteins. Maleimido-PEG is perhaps the most useful reagent for cysteine-PEGylation, but other chemistries are available for specific cysteine modification.

The present invention is further illustrated by the following examples which, however, are not to be construed as limiting the scope of protection. The features disclosed in the foregoing description and in the following examples may, both separately and in any combination thereof, be material for realizing the invention in diverse forms thereof.

EXAMPLES

Example 1

Construction of DNA encoding FVII-(S43N), FVII-(K62E), FVII-(Q64E), FVII-(I69F), FVII-(K62E/I69A), FVII-(Q64E/I69A), FVII-(Q62E/Q64E/I69A), FVII-(K62E/I69F), FVII-(Q64E/I69F), FVII-(K62E/Q64E/I69F), FVII-(S43C), FVII-(I69C), FVII-(Q64C), FVII-(M306C), FVII-(R277C), FVII-(I69N/F71T), FVII-(F71N/L73T), FVII-(R277N), and FVII-(D309N/L311T):

DNA constructs encoding FVII-(S43N), FVII-(K62E), FVII-(Q64E), FVII-(I69F), FVII-(K62E/I69A), FVII-(Q64E/I69A), FVII-(Q62E/Q64E/I69A), FVII-(K62E/I69F), FVII-(Q64E/I69F), FVII-(K62E/Q64E/I69F), FVII-(S43C), FVII-(I69C), FVII-(Q64C), FVII-(M306C), FVII-(R277C), FVII-(I69N/F71T), FVII-(F71N/L73T), FVII-(R277N), and FVII-(D309N/L311T) were prepared by site-directed mutagenesis using a supercoiled, double stranded DNA vector with insert of human FVII and two synthetic primers containing the desired mutation. The following primers were used:

```
For FVII-(S43N):
                                          (SEQ ID NO: 2)
5'-GGACGAAGCTGTTCTGGATTAACTACAGTGATGGGGACCAG-3'

(SEQ ID NO: 3)
5'-CTGGTCCCCATCACTGTAGTTAATCCAGAACAGCTTCGTCC-3'

For FVII-(K62E):
                                          (SEQ ID NO: 4)
5'-GGGGGCTCCTGCGAGGACCAGCTCCAG-3'

(SEQ ID NO: 5)
5'-CTGGAGCTGGTCCTCGCAGGAGCCCCC-3'

For FVII-(Q64E):
                                          (SEQ ID NO: 6)
5'-GGGCTCCTGCAAGGACGAGCTCCAGTCCTATATCTGC-3'

(SEQ ID NO: 7)
5'-GCAGATATAGGACTGGAGCTCGTCCTTGCAGGAGCCC-3'

For FVII-(I69F):
                                          (SEQ ID NO: 8)
5'-CCAGCTCCAGTCCTATTTCTGCTTCTGCCTCCC-3'

(SEQ ID NO: 9)
5'-GGGAGGCAGAAGCAGAAATAGGACTGGAGCTGG-3'

For FVII-(K62E/I69A):
                                          (SEQ ID NO: 10)
5'-GGGGGCTCCTGCGAGGACCAGCTCCAGTCCTATGCCTGCTTCTGCC
TC-3'
```

-continued (SEQ ID NO: 11)
5'-GAGGCAGAAGCAGGCATAGGACTGGAGCTGGTCCTCGCAGGAGCCC
CC-3'

For FVII-(Q64E/I69A):
(SEQ ID NO: 12)
5'-GGGCTCCTGCAAGGACGAGCTCCAGTCCTATGCCTGCTTCTGCCTC
C-3'

(SEQ ID NO: 13)
5'-GGAGGCAGAAGCAGGCATAGGACTGGAGCTCGTCCTTGCAGGAGCC
C-3'

For FVII-(K62E/Q64E/I69A):
(SEQ ID NO: 14)
5'-GGGGGCTCCTGCGAGGACGAGCTCCAGTCCTATGCCTGCTTCTGCC
TCC-3'

(SEQ ID NO: 15)
5'-GGAGGCAGAAGCAGGCATAGGACTGGAGCTCGTCCTCGCAGGAGCC
CCC-3'

For FVII-(S43C):
(SEQ ID NO: 16)
5'-GGACGAAGCTGTTCTGGATTTGCTACAGTGATGGGGAC-3'

(SEQ ID NO: 17)
5'-GTCCCCATCACTGTAGCAAATCCAGAACAGCTTCGTCC-3'

For FVII-(I69C)
(SEQ ID NO: 18)
5'-CCAGCTCCAGTCCTATTGCTGCTTCTGCCTCCCTG-3'

(SEQ ID NO: 19)
5'-CAGGGAGGCAGAAGCAGCAATAGGACTGGAGCTGG-3'

For FVII-(Q64C)
(SEQ ID NO: 20)
5'-GGGCTCCTGCAAGGACTGCCTCCAGTCCTATATCTG-3'

(SEQ ID NO: 21)
5'-CAGATATAGGACTGGAGGCAGTCCTTGCAGGAGCCC-3'

For FVII-(R277C)
(SEQ ID NO: 22)
5'-GGACGCTGGCCTTCGTGTGCTTCTCATTGGTCAGCG-3'

(SEQ ID NO: 23)
5'-CGCTGACCAATGAGAAGCACACGAAGGCCAGCGTCC-3'

For FVII-(M306C)
(SEQ ID NO: 24)
5'-CAACGTGCCCCGGCTGTGCACCCAGGACTGCCTGC-3'

(SEQ ID NO: 25)
5'-GCAGGCAGTCCTGGGTGCACAGCCGGGGCACGTTG-3'

FVII-(I69N/F71T):
(SEQ ID NO: 26)
5'-CCAGCTCCAGTCCTATAACTGCACCTGCCTCCCTGCCTTCG-3'

(SEQ ID NO: 27)
5'-CGAAGGCAGGGAGGCAGGTGCAGTTATAGGACTGGAGCTGG-3'

FVII-(F71N/L73T):
(SEQ ID NO: 28)
5'-CCAGTCCTATATCTGCAACTGCACCCCTGCCTTCGAGGGCCG-3'

(SEQ ID NO: 29)
5'-CGGCCCTCGAAGGCAGGGGTGCAGTTGCAGATATAGGACTGG-3'

FVII-(R277N)
(SEQ ID NO: 30)
5'-GGACGCTGGCCTTCGTGAACTTCTCATTGGTCAGCGG-3'

(SEQ ID NO: 31)
5'-CCGCTGACCAATGAGAAGTTCACGAAGGCCAGCGTCC-3'

FVII-(D309N/L311T)
(SEQ ID NO: 32)
5'-CGGCTGATGACCCAGAACTGCACCCAGCAGTCACGGAAGG-3'

(SEQ ID NO: 33)
5'-CCTTCCGTGACTGCTGGGTGCAGTTCTGGGTCATCAGCCG-3'

The oligonucleotide primers, each complementary to opposite strands of the vector insert, were extended during temperature cycling by means of Pfu DNA polymerase. On incorporation of the primers, a mutated plasmid containing staggered nicks was generated. Following temperature cycling, the product was treated with DpnI which is specific for methylated and hemimethylated DNA to digest the parental DNA template and to select for mutation-containing synthesized DNA.

Procedures for preparing a DNA construct using polymerase chain reaction using specific primers are well known to persons skilled in the art (cf. PCR Protocols, 1990, Academic ress, San Diego, Calif., USA).

Example 2

Preparation of FVII-(S43N), FVII-(K62E), FVII-(Q64E), FVII-(I69F), FVII-(K62E/I69A), FVII-(Q64E/I69A), FVII-(Q62E/Q64E/I69A), FVII-(K62E/I69F), FVII-(Q64E/I69F), FVII-(K62E/Q64E/I69F), FVII-(S43C), FVII-(I69C), FVII-(Q64C), FVII-(M306C), FVII-(R277C), FVII-(I69N/F71T), FVII-(F71N/L73T), FVII-(R277N), and FVII-(D309N/L311T).

BHK cells were transfected essentially as previously described (Thim et al. (1988) *Biochemistry* 27, 7785-7793; Persson and Nielsen (1996) *FEBS Lett.* 385, 241-243) to obtain expression of the variant FVII polypeptide. The Factor VII polypeptide was purified as follows:

Conditioned medium was loaded onto a 50-ml column of Q Sepharose Fast Flow (Pharmacia Biotech) after addition of 5 mM EDTA, and 10 mM Tris, adjustment of pH to 8.0 and adjustment of the conductivity to 10-11 mS/cm by adding water. Elution of the protein was accomplished by a gradient from 10 mM Tris, 50 mM NaCl, pH 8.0 to 10 mM Tris, 50 mM NaCl, 25 mM $CaCl_2$, pH 8.0. The fractions containing the variant FVII polypeptide were pooled, and applied to a 25-ml column containing the monoclonal antibody F1A2 (Novo Nordisk, Bagsværd, Denmark) coupled to CNBr-activated Sepharose 4B (Pharmacia Biotech). The column was equilibrated with 50 mM Hepes, pH 7.5, containing 10 mM $CaCl_2$, and 100 mM NaCl. After washing with equilibration buffer and equilibration buffer containing 2 M NaCl, bound material was eluted with equilibration buffer containing 10 mM EDTA instead of $CaCl_2$. Before use or storage, excess $CaCl_2$ over EDTA was added or the variant FVII polypeptide was transferred to a $Ca^{2+}$-containing buffer. The yield of each step was followed by factor VII ELISA measurements and the purified protein was analysed by SDS-PAGE.

Example 3

In Vitro Hydrolysis Assay

Native (wild-type) Factor VIIa and Factor VIIa variant (both hereafter referred to as "Factor VIIa") are assayed in parallel to directly compare their specific activities. The assay is carried out in a microtiter plate (MaxiSorp, Nunc, Denmark). The chromogenic substrate D-Ile-Pro-Arg-p-nitroanilide (S-2288, Chromogenix, Sweden), final concentration 1 mM, is added to Factor VIIa (final concentration 100 nM) in 50 mM Hepes, pH 7.4, containing 0.1 M NaCl, 5 mM $CaCl_2$ and 1 mg/ml bovine serum albumin. The absorbance at 405 nm is measured continuously in a SpectraMax™ 340 plate reader (Molecular Devices, USA). The absorbance developed during a 20-minute incubation, after subtraction of the absorbance in a blank well containing no enzyme, is used to calculate the ratio between the activities of variant and wild-type Factor VIIa:

Ratio=($A_{405\,nm}$ Factor VIIa variant)/($A_{405\,nm}$ Factor VIIa wild-type).

Example 4

In Vitro Proteolysis Assay

Native (wild-type) Factor VIIa and Factor VIIa variant (both hereafter referred to as "Factor VIIa") are assayed in parallel to directly compare their specific activities. The assay is carried out in a microtiter plate (MaxiSorp, Nunc, Denmark). Factor VIIa (10 nM) and Factor X (0.8 microM) in 100 microL 50 mM Hepes, pH 7.4, containing 0.1 M NaCl, 5 mM $CaCl_2$ and 1 mg/ml bovine serum albumin, are incubated for 15 min. Factor X cleavage is then stopped by the addition of 50 microL 50 mM Hepes, pH 7.4, containing 0.1 M NaCl, 20 mM EDTA and 1 mg/ml bovine serum albumin. The amount of Factor Xa generated is measured by addition of the chromogenic substrate Z-D-Arg-Gly-Arg-p-nitroanilide (S-2765, Chromogenix, Sweden), final concentration 0.5 mM. The absorbance at 405 nm is measured continuously in a SpectraMax™ 340 plate reader (Molecular Devices, USA). The absorbance developed during 10 minutes, after subtraction of the absorbance in a blank well containing no FVIIa, is used to calculate the ratio between the proteolytic activities of variant and wild-type Factor VIIa:

Ratio=($A_{405\,nm}$ Factor VIIa variant)/($A_{405\,nm}$ Factor VIIa wild-type).

Example 5

TF Binding Affinity Assay—Biosensor Assay

FVII polypeptides are tested on the Biacore instrument by passing a standard solution of the FVII polypeptide over a chip with immobilized TF. This is followed by different concentrations of sTF in 10 mM hepes pH 7.4 containing 150 mM NaCl, 10 mM $CaCl_2$ and 0.0003% polysorbate 20. Kd's are calculated from the sensorgrams using the integrated Biacore evaluation software.

The invention claimed is:

1. An isolated Factor VII variant polypeptide comprising an additional N-glycosylation site N-Xaa-S/T compared to the sequence of wild-type Factor VII (SEQ ID NO:1), wherein said additional glycosylation site is an amino acid substitution at amino acid I69 of SEQ ID NO:1, wherein Xaa is any amino acid except P, and wherein said variant polypeptide exhibits decreased Tissue Factor binding affinity compared to wild-type Factor VII.

2. The isolated Factor VII variant polypeptide of claim 1, wherein the isolated Factor VII variant polypeptide is FVII-I69N.

3. The isolated Factor VII variant polypeptide of claim 1, wherein the dissociation constant ($K_d$) of said isolated Factor VII polypeptide for Tissue Factor binding is higher than 5 nM.

4. The isolated Factor VII variant polypeptide of claim 3, wherein the dissociation constant ($K_d$) of said isolated Factor VII polypeptide for Tissue Factor binding is higher than 50 nM.

5. A composition comprising the isolated Factor VII variant polypeptide of claim 1 and a pharmaceutically acceptable carrier.

6. A method for treating bleeding episodes or bleeding disorders in a subject in need thereof, comprising: administering to the subject in need thereof a therapeutically effective amount of the isolated Factor VII variant polypeptide of claim 1.

7. A method for treating bleeding episodes or bleeding disorders or for the enhancement of normal haemostatic system in a subject in need thereof, comprising:
administering to the subject in need thereof a prophylactically effective amount of the isolated Factor VII variant polypeptide of claim 1.

8. The isolated Factor VII variant polypeptide of claim 1, wherein said additional glycosylation site further comprise an amino acid substitution at amino acid Q64 of SEQ ID NO:1.

9. The isolated Factor VII variant polypeptide of claim 1, wherein the N-glycosylation site is introduced at amino acid I69 of SEQ ID NO: 1.

10. The isolated Factor VII variant polypeptide of claim 1, wherein said additional glycosylation site further comprise an amino acid substitution at amino acid F71 of SEQ ID NO:1.

11. The isolated Factor VII variant polypeptide of claim 1, wherein said additional glycosylation site further comprise an amino acid substitution at amino acid E77 of SEQ ID NO:1.

12. The isolated Factor VII variant polypeptide of claim 1, wherein said additional glycosylation site further comprise an amino acid substitution at amino acid G78 of SEQ ID NO:1.

13. The isolated Factor VII variant polypeptide of claim 1, wherein said additional glycosylation site further comprise an amino acid substitution at amino acid Q88 of SEQ ID NO:1.

14. The isolated Factor VII variant polypeptide of claim 1, wherein said additional glycosylation site further comprise an amino acid substitution at amino acid F275 of SEQ ID NO:1.

15. The isolated Factor VII variant polypeptide of claim 1, wherein said additional glycosylation site further comprise an amino acid substitution at amino acid M306 of SEQ ID NO:1.

16. The isolated Factor VII variant polypeptide of claim 1, wherein said additional glycosylation site further comprise an amino acid substitution at amino acid T307 of SEQ ID NO:1.

17. The isolated Factor VII variant polypeptide of claim 1, wherein said additional glycosylation site further comprise an amino acid substitution at amino acid D309 of SEQ ID NO:1.

18. The isolated Factor VII variant polypeptide of claim 1, wherein the isolated Factor VII variant polypeptide is FVII-(I69N/F71T).

19. The isolated Factor VII variant polypeptide of claim 1, wherein the isolated Factor VII variant polypeptide is FVII-(F71N/L73T).

20. The isolated Factor VII variant polypeptide of claim 1, wherein the isolated Factor VII variant polypeptide is FVII-(D309N/L311T).

* * * * *